US011738050B2

(12) United States Patent
LeBeau et al.

(10) Patent No.: US 11,738,050 B2
(45) Date of Patent: Aug. 29, 2023

(54) COMPOUNDS BINDING TO FIBROBLAST ACTIVATION PROTEIN ALPHA

(71) Applicant: REGENTS OF THE UNIVERSITY OF MINNESOTA, Minneapolis, MN (US)

(72) Inventors: Aaron M. LeBeau, Lino Lakes, MN (US); Hallie M. Hintz, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 559 days.

(21) Appl. No.: 16/778,977

(22) Filed: Jan. 31, 2020

(65) Prior Publication Data

US 2020/0246383 A1 Aug. 6, 2020

Related U.S. Application Data

(60) Provisional application No. 62/799,872, filed on Feb. 1, 2019.

(51) Int. Cl.
| | | |
|---|---|---|
| *C07K 16/30* | (2006.01) | |
| *C07K 16/40* | (2006.01) | |
| *A61K 47/68* | (2017.01) | |
| *A61K 35/17* | (2015.01) | |
| *A61N 5/10* | (2006.01) | |
| *A61P 35/00* | (2006.01) | |

(52) U.S. Cl.
CPC .......... *A61K 35/17* (2013.01); *A61K 47/6803* (2017.08); *A61N 5/1049* (2013.01); *A61P 35/00* (2018.01); *C07K 16/30* (2013.01); *C07K 16/40* (2013.01); *A61N 2005/1052* (2013.01)

(58) Field of Classification Search
CPC .... C07K 16/40; C07K 16/30; C07K 2317/77; A61N 5/1049
See application file for complete search history.

(56) References Cited

U.S. PATENT DOCUMENTS

| | | | |
|---|---|---|---|
| 4,741,900 A | 5/1988 | Alvarez et al. | |
| 5,223,409 A | 6/1993 | Ladner et al. | |
| 5,849,500 A | 12/1998 | Breitling et al. | |
| 6,455,677 B1 | 9/2002 | Park et al. | |
| 8,568,727 B2 | 10/2013 | Adolf et al. | |
| 8,999,342 B2 | 4/2015 | Renner et al. | |
| 9,695,249 B2 | 7/2017 | Sevillano et al. | |

FOREIGN PATENT DOCUMENTS

| | | | |
|---|---|---|---|
| CN | 103627676 A | * 5/2014 | ............... C12N 5/20 |
| WO | 90/02809 | 3/1990 | |
| WO | 91/17271 | 11/1991 | |
| WO | 92/01047 | 1/1992 | |
| WO | 92/09690 | 6/1992 | |
| WO | 92/15679 | 9/1992 | |
| WO | 92/18619 | 10/1992 | |
| WO | 92/20791 | 11/1992 | |
| WO | 93/01288 | 1/1993 | |
| WO | 2019/084388 | 5/2019 | |

OTHER PUBLICATIONS

Holm et al. Functional mapping and single chain construction of the anticytokeratin 8 monoclonal antibody TS1. Mol. Immunol., 44, 1075-1084, 2007. (Year: 2007).*
Shepelyakovskaya et al. Effect of the format of the antibodies on their specificity. Mol. Immunol., 49, 433-440, 2011. (Year: 2011).*
Kraeber-Bodere et al., Tumor immunotargeting using innovative radionuclides. Int J Mol Sci 16, 3932-3954 (2015).
Ausubel et al. (eds.), Current Protocols in Molecular Biology, vol. 1, Green Publishing Associates, Inc., and John Wiley & Sons, Inc., N.Y.; (1994).
Davis, Basic Methods in Molecular Biology, 1st Edition; (Jan. 1, 1986).
Kabat, Sequences of Proteins of Immunological Interest, Fifth Edition, U.S. Department of Health and Human Services, NIH Publication No. 91-3242. 1991. Cover page, table of contents.
Ziani et al., Alteration of the Antitumor Immune Response by Cancer-Associated Fibroblasts. Front Immunol 9, 414 (2018).
Yang et al., FAP Promotes Immunosuppression by Cancer-Associated Fibroblasts in the Tumor Microenvironment via STAT3-CCL2 Signaling. Cancer Res 76, 4124-4135 (2016).
Xi et al., Tumor-stroma ratio (TSR) in non-small cell lung cancer (NSCLC) patients after lung resection is a prognostic factor for survival. J Thorac Dis 9, 4017-4026 (2017).
Welt et al., Antibody targeting in metastatic colon cancer: a phase I study of monoclonal antibody F19 against a cell-surface protein of reactive tumor stromal fibroblasts. J Clin Oncol 12, 1193-1203 (1994).
Wang et al., Targeting fibroblast activation protein in tumor stroma with chimeric antigen receptor T cells can inhibit tumor growth and augment host immunity without severe toxicity. Cancer Immunol Res 2, 154-166 (2014).
Wade et al., Profiling Prostate Cancer Therapeutic Resistance. Int J Mol Sci 19, (2018).
Valkenburg et al., Targeting the tumour stroma to improve cancer therapy. Nat Rev Clin Oncol 15, 366-381 (2018).
Tuxhorn et al., Stromal cells promote angiogenesis and growth of human prostate tumors in a differential reactive stroma (DRS) xenograft model. Cancer Res 62, 3298-3307 (2002).

(Continued)

*Primary Examiner* — Elly-Gerald Stoica
(74) *Attorney, Agent, or Firm* — Mueting Raasch Group

(57) ABSTRACT

This disclosure describes a compound that binds to fibroblast activation protein alpha (FAP), compositions including the compound, and methods of using the compound, and compositions. In some embodiments, the compound is a monoclonal antibody that binds FAP. The compound may be used, for example, as a research tool, in clinical imaging, as a diagnostic agent, or as a therapeutic agent.

9 Claims, 28 Drawing Sheets

(7 of 28 Drawing Sheet(s) Filed in Color)

Specification includes a Sequence Listing.

(56) References Cited

OTHER PUBLICATIONS

Tuxhorn et al., Reactive stroma in human prostate cancer: induction of myofibroblast phenotype and extracellular matrix remodeling. Clin Cancer Res 8, 2912-2923 (2002).
Tsuchiya et al., The diversity of H3 loops determines the antigen-binding tendencies of antibody CDR loops. Protein Sci 25, 815-825 (2016).
Traunecker et al., Janusin: new molecular design for bispecific reagents. Int J Cancer Suppl 7, 51-52 (1992).
Traunecker et al., Bispecific single chain molecules (Janusins) target cytotoxic lymphocytes on HIV infected cells. EMBO J 10, 3655-3659 (1991).
Tao et al., Cancer associated fibroblasts: An essential role in the tumor microenvironment. Oncol Lett 14, 2611-2620 (2017).
Takeda et al., Construction of chimaeric processed immunoglobulin genes containing mouse variable and human constant region sequences. Nature 314, 452-454 (1985).
Suetsugu et al., Imaging the recruitment of cancer-associated fibroblasts by liver-metastatic colon cancer. J Cell Biochem 112, 949-953 (2011).
Songsivilai et al., Bispecific antibody: a tool for diagnosis and treatment of disease. Clin Exp Immunol 79, 315-321 (1990).
Snyder et al., Expression of a Recombinant High Affinity IgG Fc Receptor by Engineered NK Cells as a Docking Platform for Therapeutic mAbs to Target Cancer Cells. Front Immunol 9, 2873 (2018).
Smith et al., Phage Display. Chem Rev 97, 391-410 (1997).
Singer et al., Optimal humanization of 1B4, an anti-CD18 murine monoclonal antibody, is achieved by correct choice of human V-region framework sequences. J Immunol 150, 2844-2857 (1993).
Sela-Culang et al., The structural basis of antibody-antigen recognition. Front Immunol 4, 302 (2013).
Scott et al., A Phase I dose-escalation study of sibrotuzumab in patients with advanced or metastatic fibroblast activation protein-positive cancer. Clin Cancer Res 9, 1639-1647 (2003).
Schuberth et al., Treatment of malignant pleural mesothelioma by fibroblast activation protein-specific re-directed T cells. J Transl Med 11, 187 (2013).
Schmittgen et al., Analyzing real-time PCR data by the comparative C(T) method. Nat Protoc 3, 1101-1108 (2008).
Scanlan et al., Molecular cloning of fibroblast activation protein alpha, a member of the serine protease family selectively expressed in stromal fibroblasts of epithelial cancers. Proc Natl Acad Sci U S A 91, 5657-5661 (1994).
Ruger et al., In vivo near-infrared fluorescence imaging of FAP-expressing tumors with activatable FAP-targeted, single-chain Fv-immunoliposomes. J Control Release 186, 1-10 (2014).
Ronnov-Jessen et al., Cellular changes involved in conversion of normal to malignant breast: importance of the stromal reaction. Physiol Rev 76, 69-125 (1996).
Rezvani et al., Engineering Natural Killer Cells for Cancer Immunotherapy. Mol Ther 25, 1769-1781 (2017).
Pineiro-Sanchez et al., Identification of the 170-kDa melanoma membrane-bound gelatinase (seprase) as a serine integral membrane protease. J Biol Chem 272, 7595-7601 (1997).
Pietras et al., Functions of paracrine PDGF signaling in the proangiogenic tumor stroma revealed by pharmacological targeting. PLoS Med 5, e19 (2008).
Peng et al., Biological characteristics and genetic heterogeneity between carcinoma-associated fibroblasts and their paired normal fibroblasts in human breast cancer. PLoS One 8, e60321 (2013).
Park et al., Pre-clinical mouse models of human prostate cancer and their utility in drug discovery. Curr Protoc Pharmacol Chapter 14, Unit 14 15 (2010).
Ostermann et al., Effective immunoconjugate therapy in cancer models targeting a serine protease of tumor fibroblasts. Clin Cancer Res 14, 4584-4592 (2008).
Orlandi et al., Cloning immunoglobulin variable domains for expression by the polymerase chain reaction. Proc Natl Acad Sci U S A 86, 3833-3837 (1989).
Olumi et al., Carcinoma-associated fibroblasts direct tumor progression of initiated human prostatic epithelium. Cancer Res 59, 5002-5011 (1999).
Olaso et al., Tumor-dependent activation of rodent hepatic stellate cells during experimental melanoma metastasis. Hepatology 26, 634-642 (1997).
Narra et al., Phase II trial of single agent Val-boroPro (Talabostat) inhibiting Fibroblast Activation Protein in patients with metastatic colorectal cancer. Cancer Biol Ther 6, 1691-1699 (2007).
Nair et al., A cancer stem cell model as the point of origin of cancer-associated fibroblasts in tumor microenvironment. Sci Rep 7, 6838 (2017).
Morvan et al., NK cells and cancer: you can teach innate cells new tricks. Nat Rev Cancer 16, 7-19 (2016).
Mersmann et al., Human antibody derivatives against the fibroblast activation protein for tumor stroma targeting of carcinomas. Int J Cancer 92, 240-248 (2001).
Lu et al., The extracellular matrix: a dynamic niche in cancer progression. J Cell Biol 196, 395-406 (2012).
Loktev et al., A Tumor-Imaging Method Targeting Cancer-Associated Fibroblasts. J Nucl Med 59, 1423-1429 (2018).
Lo et al., Photodynamic molecular beacon triggered by fibroblast activation protein on cancer-associated fibroblasts for diagnosis and treatment of epithelial cancers. J Med Chem 52, 358-368 (2009).
Lo et al., Fibroblast activation protein augments progression and metastasis of pancreatic ductal adenocarcinoma. JCI Insight 2, (2017).
Liu et al., Fibroblast activation protein overexpression and clinical implications in solid tumors: a meta-analysis. PLoS One 10, e0116683 (2015).
Li et al., Human iPSC-Derived Natural Killer Cells Engineered with Chimeric Antigen Receptors Enhance Anti-tumor Activity. Cell Stem Cell 23, 181-192 e185 (2018).
Li et al., Activatable near-infrared fluorescent probe for in vivo imaging of fibroblast activation protein-alpha. Bioconjug Chem 23, 1704-1711 (2012).
Lebeau et al., Targeting the cancer stroma with a fibroblast activation protein-activated promelittin protoxin. Mol Cancer Ther 8, 1378-1386 (2009).
Kuroda et al., Systematic classification of CDR-L3 in antibodies: implications of the light chain subtypes and the VL-VH interface. Proteins 75, 139-146 (2009).
Kuhn et al., Recombinant antibodies for diagnostics and therapy against pathogens and toxins generated by phage display. Proteomics Clin Appl 10, 922-948 (2016).
Yu, "Analyzing Antibody Sequence for Recombinant Antibody Expression" GenScript Presentation dated May 20, 2015; 35 pages. Accessed online on Jul. 14, 2021 at genscript.com/gsfiles/techfiles/Analyzing_antibody_sequence_for_recombinant_antibody_expression.pdf.
Kraman et al., Suppression of antitumor immunity by stromal cells expressing fibroblast activation protein-alpha. Science 330, 827-830 (2010).
Kostelny et al., Formation of a bispecific antibody by the use of leucine zippers. J Immunol 148, 1547-1553 (1992).
Kojima et al., Autocrine TGF-beta and stromal cell-derived factor-1 (SDF-1) signaling drives the evolution of tumor-promoting mammary stromal myofibroblasts. Proc Natl Acad Sci U S A 107, 20009-20014 (2010).
Koczorowska et al., Fibroblast activation protein-alpha, a stromal cell surface protease, shapes key features of cancer associated fibroblasts through proteome and degradome alterations. Mol Oncol 10, 40-58 (2016).
Kim et al., Rapid identification of recombinant Fabs that bind to membrane proteins. Methods 55, 303-309 (2011).
Kessenbrock et al., Matrix metalloproteinases: regulators of the tumor microenvironment. Cell 141, 52-67 (2010).
Jones et al., Replacing the complementarity-determining regions in a human antibody with those from a mouse. Nature 321, 522-525 (1986).

(56) References Cited

OTHER PUBLICATIONS

Holliger et al., "Diabodies": small bivalent and bispecific antibody fragments. Proc Natl Acad Sci U S A 90, 6444-6448 (1993).
Hofheinz et al., Stromal antigen targeting by a humanised monoclonal antibody: an early phase II trial of sibrotuzumab in patients with metastatic colorectal cancer. Onkologie 26, 44-48 (2003).
Hintz et al., Development of a Cross-Reactive Monoclonal Antibody for Detecting the Tumor Stroma. Bioconjug Chem 30, 1466-1476 (2019).
Henry et al., Clinical implications of fibroblast activation protein in patients with colon cancer. Clin Cancer Res 13, 1736-1741 (2007).
Hanahan et al., Accessories to the crime: functions of cells recruited to the tumor microenvironment. Cancer Cell 21, 309-322 (2012).
Grupp et al., A novel model to study renal myofibroblast formation in vitro. Kidney Int 59, 543-553 (2001).
Gottschalk et al., A vaccine that co-targets tumor cells and cancer associated fibroblasts results in enhanced antitumor activity by inducing antigen spreading. PLoS One 8, e82658 (2013).
Gonzalez-Zubeldia et al., Co-migration of colon cancer cells and CAFs induced by TGFbeta(1) enhances liver metastasis. Cell Tissue Res 359, 829-839 (2015).
Glienke et al., Advantages and applications of CAR-expressing natural killer cells. Front Pharmacol 6, 21 (2015).
Garin-Chesa et al., Cell surface glycoprotein of reactive stromal fibroblasts as a potential antibody target in human epithelial cancers. Proc Natl Acad Sci U S A 87, 7235-7239 (1990).
Folkman et al., Induction of angiogenesis during the transition from hyperplasia to neoplasia. Nature 339, 58-61 (1989).
Fischer et al., Radioimmunotherapy of fibroblast activation protein positive tumors by rapidly internalizing antibodies. Clin Cancer Res 18, 6208-6218 (2012).
Fang et al., A multi-antigen vaccine in combination with an immunotoxin targeting tumor-associated fibroblast for treating murine melanoma. Mol Ther Oncolytics 3, 16007 (2016).
Erdogan et al., Cancer-associated fibroblasts promote directional cancer cell migration by aligning fibronectin. J Cell Biol 216, 3799-3816 (2017).
Dvorak, Tumors: wounds that do not heal-redux. Cancer Immunol Res 3, 1-11 (2015).
Duda et al., Malignant cells facilitate lung metastasis by bringing their own soil. Proc Natl Acad Sci U S A 107, 21677-21682 (2010).
De Veirman et al., Cancer associated fibroblasts and tumor growth: focus on multiple myeloma. Cancers (Basel) 6, 1363-1381 (2014).
Cohen et al., Fibroblast activation protein and its relationship to clinical outcome in pancreatic adenocarcinoma. Pancreas 37, 154-158 (2008).
Chothia et al., Canonical structures for the hypervariable regions of immunoglobulins. J Mol Biol 196, 901-917 (1987).
Cheng et al., Promotion of tumor growth by murine fibroblast activation protein, a serine protease, in an animal model. Cancer Res 62, 4767-4772 (2002).
Chan et al., Targeting nuclear receptors in cancer-associated fibroblasts as concurrent therapy to inhibit development of chemoresistant tumors. Oncogene 37, 160-173 (2018).
Bussard et al., Tumor-associated stromal cells as key contributors to the tumor microenvironment. Breast Cancer Res 18, 84 (2016).
Brunker et al., RG7386, a Novel Tetravalent FAP-DR5 Antibody, Effectively Triggers FAP-Dependent, Avidity-Driven DR5 Hyperclustering and Tumor Cell Apoptosis. Mol Cancer Ther 15, 946-957 (2016).
Brennen et al., Rationale behind targeting fibroblast activation protein-expressing carcinoma-associated fibroblasts as a novel chemotherapeutic strategy. Mol Cancer Ther 11, 257-266 (2012).
Barron et al., The reactive stroma microenvironment and prostate cancer progression. Endocr Relat Cancer 19, R187-204 (2012).
Balkwill et al., Smoldering and polarized inflammation in the initiation and promotion of malignant disease. Cancer Cell 7, 211-217 (2005).
Ayala et al., Reactive stroma as a predictor of biochemical-free recurrence in prostate cancer. Clin Cancer Res 9, 4792-4801 (2003).
Ao et al., Identification of Cancer-Associated Fibroblasts in Circulating Blood from Patients with Metastatic Breast Cancer. Cancer Res 75, 4681-4687 (2015).
Andersen et al., Integrative metabolic and transcriptomic profiling of prostate cancer tissue containing reactive stroma. Sci Rep 8, 14269 (2018).
Akashi et al., Basement membrane matrix modifies cytokine interactions between lung cancer cells and fibroblasts. Pathobiology 72, 250-259 (2005).
Lebeau et al., Targeting uPAR with Antagonistic Recombinant Human Antibodies in Aggressive Breast Cancer. Cancer Res, 2070-81 (2013).
McDevitt et al., Feed-forward alpha particle radiotherapy ablates androgen receptor-addicted prostate cancer. Nature Comm, 9:1629 (2018).
Thorek et al., Internalization of secreted antigen-targeted antibodies by the neonatal Fc receptor for precision imaging of the androgen receptor. Sci Transl Med, 367ra167 (2016).
Jing et al., Identification of an ADAM17 cleavage region in human CD16 (FcgammaRIII) and the engineering of a non-cleavable version of the receptor in NK cells. PLoS One 10, e0121788 (2015).
Lajoie et al., ADAM17-mediated shedding of FcgammaRIIIA on human NK cells: identification of the cleavage site and relationship with activation. J Immunol 192, 741-751 (2014).
Nimmerjahn et al., Fcgamma receptors as regulators of immune responses. Nat Rev Immunol 8, 34-47 (2008).
Kiyoshi et al., Structural basis for binding of human IgG1 to its high-affinity human receptor FcgammaRI. Nat Commun 6, 6866 (2015).
Bruhns et al., Specificity and affinity of human Fcgamma receptors and their polymorphic variants for human IgG subclasses. Blood 113, 3716-3725 (2009).
Alderson et al., Clinical cancer therapy by NK cells via antibody-dependent cell-mediated cytotoxicity. J Biomed Biotechnol 2011, 379123 (2011).
Wang et al., NK Cell-Mediated Antibody-Dependent Cellular Cytotoxicity in Cancer Immunotherapy. Front Immunol 6, 368 (2015).
Mishra et al., Anti-ADAM17 monoclonal antibody MEDI3622 increases IFNgamma production by human NK cells in the presence of antibody-bound tumor cells. Cancer Immunol Immunother 67, 1407-1416 (2018).
Lai et al., Alterations in expression and function of signal-transducing proteins in tumor-associated T and natural killer cells in patients with ovarian carcinoma. Clin Cancer Res 2, 161-173 (1996).
Hintz et al., Development of a Cross-Reactive Monoclonal Antibody for Detecting the Tumor Stroma. Supporting Information. Bioconjug Chem 30, S1-S3. 3 pages (2019).

* cited by examiner

FIG. 2E
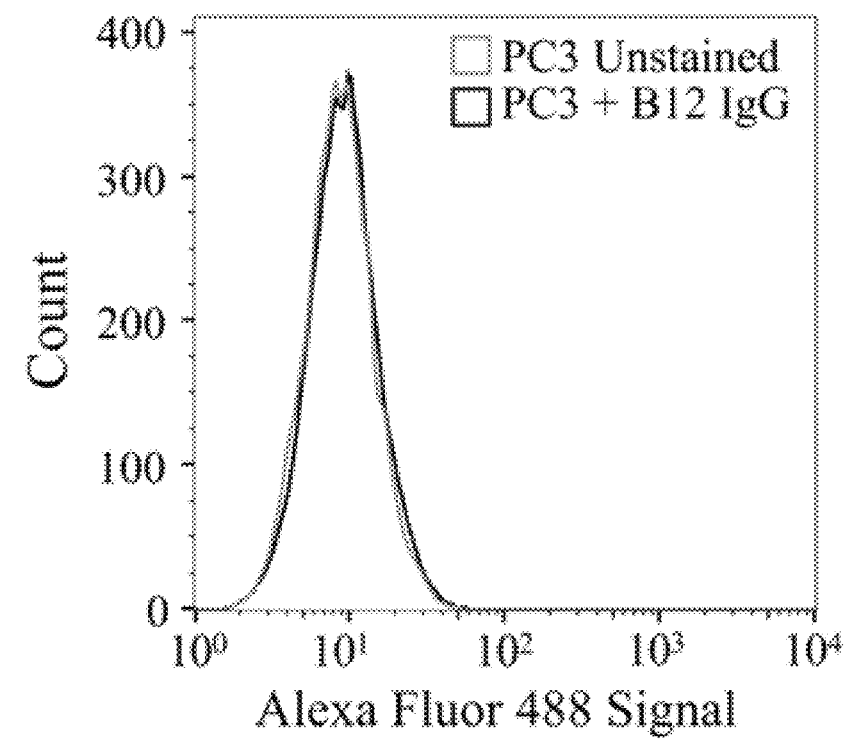
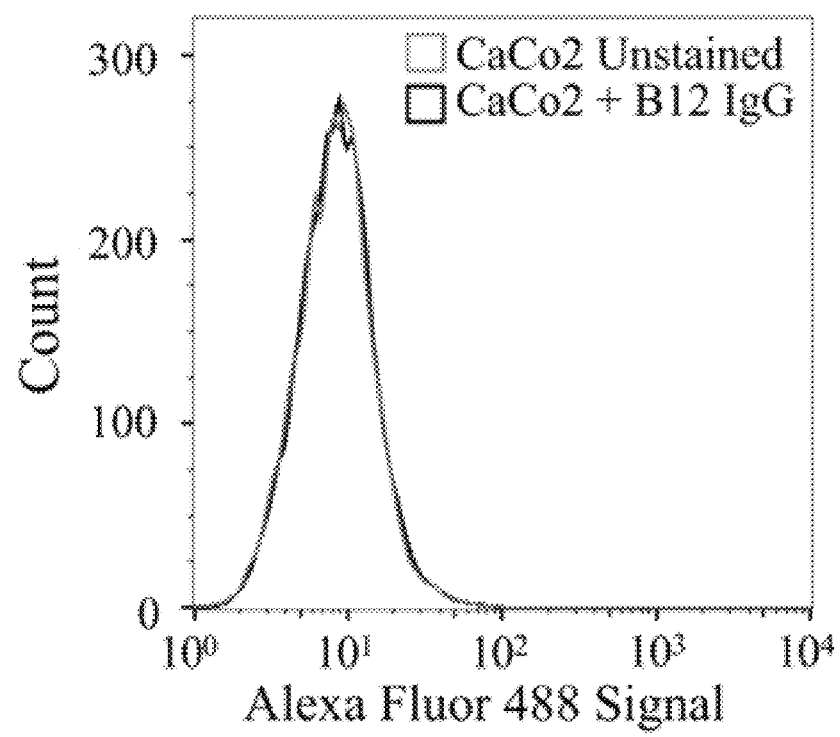

FIG. 10A

| | | | |
|---|---|---|---|
| Consensus | YYC-Q--S-P-TFG- | | |
| B12 Light Chain Sequence | YYCLQYASYPWTFGG | 15 |
| ESC11 Light Chain | YYCQQFQS-PYTFGQ | 14 |
| ESC14 Light Chain | YYCMQALQTPPTFGQ | 15 |
| F19 Light Chain | YYCXXYFSYPLTFGX | 15 |
| MFP5 Light Chain | YYCQWSFNPPTFGG | 15 |

FIG. 10B

| | | | | |
|---|---|---|---|---|
| Consensus | YCAR----A------FDYWGQGTLVTVSS----- | | | |
| B12 Heavy Chain Sequence | YCAR---D-------YFDYWGQGTTLTVSS----- | 20 |
| ESC11 Heavy Chain | YCARGARWQARPATIDGVAFDIWGQGTMVTVSS----- | 34 |
| ESC14 Heavy Chain | YCAR---DWSRSGY--YLPDYWSQGTLVTSS----- | 26 |
| F19 Heavy Chain | YCAR---RRIAYGYD--EQHAMDYWXQTLVTVSS----- | 30 |
| MFP5 Heavy Chain | FCAR---TLTA----PFAFWGQGTLVTVSAAKTTAPSVYPLAP | 38 |

FIG. 11B
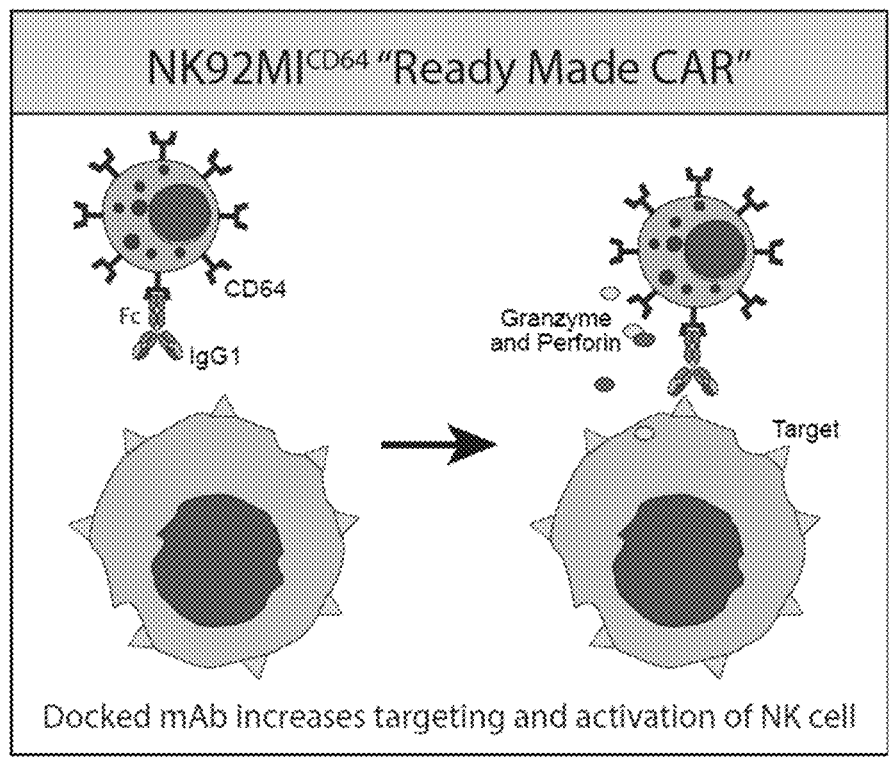
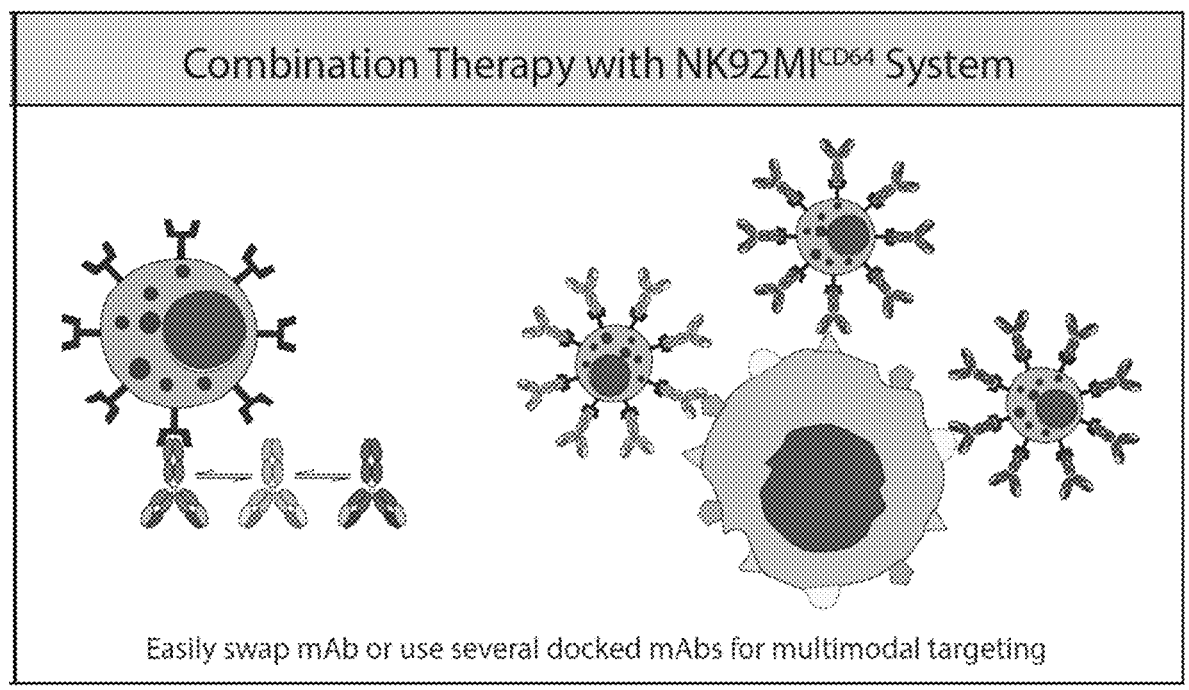

COMPOUNDS BINDING TO FIBROBLAST ACTIVATION PROTEIN ALPHA

CONTINUING APPLICATION DATA

This application claims the benefit of U.S. Provisional Application Ser. No. 62/799,872, filed Feb. 1, 2019, which is incorporated by reference herein.

SEQUENCE LISTING

This application contains a Sequence Listing electronically submitted to the United States Patent and Trademark Office via EFS-Web as an ASCII text file entitled "SeqListing-110-000612_ST25.txt" having a size of 4 kilobytes and created on Jan. 29, 2020. Due to the electronic filing of the Sequence Listing, the electronically submitted Sequence Listing serves as both the paper copy required by 37 CFR § 1.821(c) and the CRF required by § 1.821(e). The information contained in the Sequence Listing is incorporated by reference herein.

BACKGROUND

Solid tumors include malignant cells and a heterogeneous mixture of supporting stromal cells that are essential for tumor growth beyond a few millimeters. Stromal transformation in the tumor microenvironment occurs during the early stages of carcinogenesis and has been likened to processes in normal wound healing. Tumor growth is associated with adaptations in the supporting stroma, including neoangiogenesis; the recruitment of fibroblasts and immune cells; the release of peptide-signaling molecules and proteases; and the extensive remodeling of the extracellular matrix. High stromal composition is a characteristic of many solid tumors, including prostate, breast, colon, and lung, with tumor-stroma ratios ranging from 20 percent (%) to at least 50% of the tumor mass. Even higher ratios, greater than 90%, are seen in carcinomas with desmoplastic reactions.

Cancer-associated fibroblasts (CAFs) are the major cell type in the stromal compartment and play a significant role in tumorigenesis and invasion. The exact origin of these transformed reactive fibroblasts is still unknown, but several cell types are suspected including fibroblasts, adipocytes, cancer stem cells, bone marrow mesenchymal stem cells, and endothelial cells that have undergone endothelial mesenchymal transition. Malignant cells directly contribute to formation of the reactive stroma through mechanical stress and secretion of TGF-β, growth factors, and chemokines. Cross-talk between cancer cells and CAFs creates a paracrine feedback loop that stimulates tumor growth, promotes inflammation and immunosuppression, and drives tumor invasion. Furthermore, CAFs are involved in several mechanisms of therapeutic resistance and immune evasion which augments progression and metastasis of the disease.

The membrane-bound serine protease fibroblast activation protein alpha (FAP) is highly expressed on CAFs in 90% of epithelial tumors, and its expression is associated with aggressive phenotypes. FAP expression has also been detected in some soft tissue and bone sarcomas. The protease has dipeptidyl peptidase, gelatinase, and collagenase activity. FAP activity contributes to tumorigenesis through extracellular matrix degradation and growth factor activation, and FAP-expressing cells have been shown to mediate anti-tumor immunity in the tumor microenvironment. In nonmalignant tissue, FAP is expressed by reactive fibroblasts in wound healing, and in diseased tissue such as rheumatoid arthritis, lung fibrosis, and liver cirrhosis.

SUMMARY OF THE INVENTION

Fibroblast activation protein alpha (FAP) expression in the tumor microenvironment makes it a promising candidate for therapeutic targeting and molecular imaging, but the diagnostic or therapeutic potential of existing FAP antibodies has been limited. This disclosure describes a compound that binds to FAP and methods of using the compound including as a diagnostic or therapeutic agent. In some embodiments, the compound is a monoclonal antibody for FAP.

In one aspect, this disclosure describes a composition that includes a compound that binds to FAP. In some embodiments, the compound includes an amino acid sequence that includes SEQ ID NO:3, SEQ ID NO:4, and SEQ ID NO:5; and an amino acid sequence that includes SEQ ID NO:6, SEQ ID NO:7, and SEQ ID NO:8. In some embodiments the compound includes an amino acid sequence that includes SEQ ID NO:2 and an amino acid sequence that includes SEQ ID NO: 1.

In some embodiments the compound includes an antibody including, for example, a monoclonal antibody. In some embodiments the compound includes a humanized monoclonal antibody. In some embodiments the compound includes a single-chain variable fragment (scFv). In some embodiments the compound includes B12 IgG.

In some embodiments, the compound includes a labeled compound. In some embodiments, the compound includes a compound conjugated to a reporter molecule. Exemplary reporter molecules include an enzyme, a fluorescent dye, an infrared dye, a chemiluminescent reporter, or a hapten.

In some embodiments, the composition includes a cell-based immunotherapeutic. Exemplary cell-based immunotherapeutics include a chimeric antigen receptor (CAR) T cell and/or a CAR natural killer (NK) cell.

In some embodiments, the composition includes a pharmaceutical composition.

In a further aspect, this disclosure describes a method of using a composition that includes a compound that binds to FAP, as described herein. In some embodiments, the method may be used in the treatment of a tumor or in the diagnosis of a tumor.

In some embodiments, the composition may be used as a diagnostic agent. For example, the method may include visualizing the margin of a tumor.

In some embodiments, the composition may be used in a method that includes detecting a FAP-positive tumor. An exemplary method of detecting a FAP-positive tumor is positron emission tomography/computed tomography (PET/CT) imaging. In some embodiments, the composition may be used in a method that includes identifying a cancer-associated fibroblast (CAF).

In some embodiments, the composition may be used as a therapeutic agent. For example, the method may include using the composition in an antibody-targeted therapy, a cell-based immunotherapeutic, or to identify a cancer-associated fibroblast (CAF). An exemplary antibody-targeted therapy is radioimmunotherapy.

In some embodiments, including when the method includes detecting the compound, the composition may include the compound conjugated to a reporter molecule. Exemplary reporter molecules include an enzyme, a fluorescent dye, an infrared dye, a chemiluminescent reporter, or a hapten.

In a further aspect, this disclosure describes a monoclonal antibody that includes an amino acid sequence including a light chain variable region, the light chain variable region CDR1 sequence including SEQ ID NO:3, the light chain variable region CDR2 sequence including SEQ ID NO:4, and the light chain variable region CDR3 sequence including SEQ ID NO:5; or an amino acid sequence including a heavy chain variable region, the heavy chain variable region CDR1 sequence including SEQ ID NO:6, the heavy chain variable region CDR2 sequence including SEQ ID NO:7, and the heavy chain variable region CDR3 sequence including SEQ ID NO:8; or both. In some embodiments the monoclonal antibody includes a light chain variable region including the amino acid sequence of SEQ ID NO:1; or a heavy chain variable region including the amino acid sequence of SEQ ID NO:2; or both.

In some embodiments, the monoclonal antibody includes B12 IgG.

In yet another aspect, this disclosure describes methods of using the monoclonal antibody including, for example, to image a cell expressing FAP or as an antibody-targeted therapy.

The term "antibody" as used herein refers to a molecule that contains at least one antigen binding site that immunospecifically binds to a particular antigen target of interest. The term "antibody" thus includes but is not limited to a full length antibody and/or its variants, a fragment thereof, peptibodies and variants thereof, multispecific antibodies (for example, bispecific antibodies) formed from at least two intact antibodies, human antibodies, humanized antibodies, and antibody mimetics that mimic the structure and/or function of an antibody or a specified fragment or portion thereof, including single chain antibodies, single-domain antibodies, and fragments thereof. Binding of an antibody to a target can cause a variety of effects, such as but not limited to where such binding modulates, decreases, increases, antagonizes, agonizes, mitigates, alleviates, blocks, inhibits, abrogates and/or interferes with at least one target activity or binding, or with receptor activity or binding, in vitro, in situ, and/or in vivo. An antibody of the present disclosure thus encompasses antibody fragments capable of binding to a biological molecule (such as an antigen or receptor) or portions thereof, including but not limited to Fab, Fab' and F(ab')2, pFc', Fd, a single domain antibody (sdAb), a variable fragment (Fv), a single-chain variable fragment (scFv) or a disulfide-linked Fv (sdFv); a diabody or a bivalent diabody; a linear antibody; a single-chain antibody molecule; and a multispecific antibody formed from antibody fragments. The antibody may be of any type (for example, IgG, IgE, IgM, IgD, IgA and IgY), class (for example, IgG1, IgG2, IgG3, IgG4, IgA1 and IgA2), or subclass.

The term "monoclonal antibody" as used herein refers to an antibody obtained from a population of substantially homogeneous antibodies, that is, the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which typically include different antibodies directed against different determinants (epitopes), each monoclonal antibody is directed against a single determinant on the antigen. The monoclonal antibody may be produced recombinantly including, for example, by cells stably or transiently transfected with the heavy and light chain genes encoding the monoclonal antibody. The modifier "monoclonal" indicates the character of the antibody as being obtained from a substantially homogeneous population of antibodies, wherein the antibody is an antibody as defined above; "monoclonal" is not to be construed as requiring engineering of the antibody by any particular method.

As used herein, "isolated" refers to material removed from its original environment (for example, the natural environment if it is naturally occurring), and thus is altered "by the hand of man" from its natural state.

As used herein, "room temperature" is 18° C. to 28° C. or, more preferably, 20° C. to 26° C. In some embodiments, "room temperature" is 25° C.

As used herein "sequence identity" between two polypeptides is determined by comparing the amino acid sequence of one polypeptide to the sequence of a second polypeptide. When discussed herein, whether any particular polypeptide is at least 40 percent (%), at least 45%, at least 50%, at least 55%, at least 60%, at least 65%, at least 70%, at least 75%, at least 80%, at least 85%, at least 90%, at least 95%, at least 96%, at least 97%, at least 98%, or at least 99% identical to another polypeptide may be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman 1981 *Advances in Applied Mathematics* 2:482-489, to find the best segment of homology between two sequences. When using BESTFIT or any other sequence alignment program to determine whether a particular sequence is, for example, 95% identical to a reference sequence according to the present invention, the parameters are set such that the percentage of identity is calculated over the full length of the reference polypeptide sequence and that gaps in homology of up to 5% of the total number of amino acids in the reference sequence are allowed.

"Binding affinity" or "affinity binding" refers to the strength of the sum total of noncovalent interactions between a single binding site of a molecule (for example, an antibody) and its binding partner (for example, an antigen or antigenic epitope). The affinity of a molecule X for its partner Y is represented by the dissociation constant ($K_D$), which can generally be determined by using methods known in the art, for example, using the BIACORE biosensor, commercially available from BIACORE (GE Healthcare Worldwide, Chicago, Ill.). In some embodiments, antibodies of the present disclosure may be described in terms of their binding affinity for FAP. In some embodiments, antibodies of the present disclosure include antibodies that interact with an antigen wherein the dissociation constant ($K_D$) is less than or equal to $5\times10^{-6}$ M, less than or equal to $1\times10^{-6}$ M, less than or equal to $5\times10^{-7}$ M, less than or equal to $1\times10^{-7}$ M, less than or equal to $5\times10^{-8}$ M, less than or equal to $1\times10^{-8}$ M, less than or equal to $5\times10^{-9}$ M, less than or equal to $1\times10^{-9}$ M, less than or equal to $5\times10^{-10}$ M, less than or equal to $1\times10^{-10}$ M, less than or equal to $5\times10^{-11}$ M, less than or equal to $1\times10^{-11}$ M, less than or equal to $5\times10^{-12}$ M, less than or equal to $1\times10^{-12}$ M, less than or equal to $5\times10^{-13}$ M, less than or equal to $1\times10^{-13}$ M, less than or equal to $5\times10^{-14}$ M, less than or equal to $1\times10^{-14}$ M, less than or equal to $5\times10^{-15}$ M, or less than or equal to $1\times10^{-15}$ M.

As used herein, the term "subject" includes, but is not limited to, humans and non-human vertebrates. In some embodiments, a subject is a mammal, particularly a human. A subject may be an individual. A subject may be an "individual," "patient," or "host." Non-human vertebrates include livestock animals, companion animals, and laboratory animals. Non-human subjects also include non-human primates as well as rodents, such as, but not limited to, a rat or a mouse. Non-human subjects also include, without limitation, chickens, horses, cows, pigs, goats, dogs, cats, guinea pigs, hamsters, mink, and rabbits.

As used herein "in vitro" is in cell culture and "in vivo" is within the body of a subject.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

All headings are for the convenience of the reader and should not be used to limit the meaning of the text that follows the heading, unless so specified.

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A. mRNA levels of human FAP (hFAP) were analyzed using quantitative RT-PCR in cells of a transduced human FAP$^+$ CWR-R1-Enzalutamide Resistant/luciferase$^+$ cell line (R1-EnzR$^{FAP}$) and a parental human FAP$^{neg}$ CWR-R1-Enzalutamide Resistant/luciferase$^+$ cell line (R1-EnzR). mRNA fold change is normalized to R1-EnzR. ***$p<0.001$. FIG. 1B. Western blot with a commercial antibody was used to detect hFAP protein expression in R1-EnzR$^{FAP}$ and R1-EnzR cells. FIG. 1C. Human FAP membrane expression in R1-EnzR$^{FAP}$ cells was investigated using flow cytometry. Transduced (blue line) and parental (purple line) cells were stained with a commercial PE conjugated monoclonal antibody. Unstained cells (green line) were used as a negative control.

FIG. 2A-FIG. 2E show in vitro characterization of the anti-FAP monoclonal antibody B12 immunoglobulin G (IgG). FIG. 2A. B12 IgG specificity for human fibroblast activation protein alpha (hFAP) (circle), mouse fibroblast activation protein alpha (mFAP) (square), and the homologous protease human dipeptidyl peptidase IV (hDPP-IV) (triangle) was determined by enzyme-linked immunosorbent assay (ELISA). B12 IgG was serial-diluted from 500 nM to 0.1 nM and added to protein coated wells. B12 IgG binding was detected by a peroxidase conjugated human IgG monoclonal antibody. FIG. 2B. Surface plasmon resonance was used to calculate the binding affinity of B12 IgG for hFAP ($K_D$=3.39 nM) and mFAP ($K_D$=1.86 nM). FIG. 2C. B12 IgG binding to membrane-bound FAP was analyzed by flow cytometry. R1-EnzR$^{FAP}$ (orange line) and R1-EnzR (red line) cells were stained with Alexa Fluor 488 conjugated B12 IgG. Unstained cells (blue line) were used as a negative control. FIG. 2D. mRNA levels of hDPP-IV were investigated by quantitative RT-PCR in prostate (R1-EnzR, R1-EnzR$^{FAP}$, PC3) and colon (Caco2) cancer cells. mRNA fold change is normalized to R1-EnzR. **p 0.01. FIG. 2E. Flow cytometry confirmed that B12 IgG does not bind to hDPP-IV-expressing cells. PC3 and Caco2 cells were stained with Alexa Fluor 488 conjugated B12 IgG (black lines) and compared to an unstained control (gray lines).

FIG. 3A. B12 IgG externally stains R1-EnzR$^{FAP}$ cells. Fixed cells were incubated for 1 hour with B12 IgG and imaged using murine anti-human IgG Alexa Fluor 488 as a detection agent. FIG. 3B. R1-EnzR$^{FAP}$ cells internalize B12 IgG. Cells were fixed and permeabilized after incubation for 1 hour with B12 IgG. Green punctate structures were observed within R1-EnzR$^{FAP}$ cells when imaged using murine anti-human IgG Alexa Fluor 488 as a detection agent. Parental R1-EnzR cells were used as a specificity control in both FIG. 3A and FIG. 3B.

FIG. 4A. Localization of IRD-800CW conjugated B12 IgG in mice bearing either a R1-EnzR$^{FAP}$ or R1-EnzR tumor xenograft. IRDye-800CW conjugated to a non-specific human IgG1 antibody was used as an isotype control. Tumor and secondary organs were imaged ex vivo at 144 hours. Key: 1. Tumor 2. Liver 3. Stomach 4. Intestines 5. Kidneys 6. Pancreas 7. Spleen 8. Heart 9. Lungs 10. Prostate 11. Testis. FIG. 4B. Fluorescence (near-infrared) signal measured by placing region-of-interest at center of R1-EnzR$^{FAP}$ or R1-EnzR tumor xenografts treated with IRDye-800CW conjugated B12 IgG or isotype control. Signal intensity of R1-EnzR$^{FAP}$ (square) and R1-EnzR (circle) tumor xenografts is expressed as total signal with the background signal subtracted. Statistics compare B12 signal to the isotype control for each xenograft. p 0.01, *p 0.001.

FIG. 5A. Localization of IRD-800CW-conjugated B12 IgG in a mouse bearing a R1-EnzR$^{FAP}$ metastatic tumor xenograft. Metastases were identified by bioluminescent imaging (BLI). FIG. 5B. Micro-computed tomography (μCT) was used to determine bone surface thickness of the front limbs of the R1-EnzR$^{FAP}$ mouse. The front limbs of a mouse without metastases were used as a negative control. Additional results are shown in FIG. 9.

FIG. 6A. mRNA levels of hFAP (black) and mFAP (gray) in tumor xenografts were analyzed using quantitative RT-PCR. mRNA fold change is normalized to murine liver tissue. ***p 0.001. FIG. 6B-FIG. 6D. Representative images of immunohistochemistry (IHC) staining with a secondary anti-human IgG monoclonal antibody. IHC staining was used to detect IRDye-800CW conjugated B12 IgG penetration ex vivo in (FIG. 6B) R1-EnzR$^{FAP}$ and (FIG. 6C) R1-EnzR tumor tissues. No IHC staining was observed in (FIG. 6D) R1-EnzRFAP and (FIG. 6E) R1-EnzR tumor tissues treated with the IRDye-800CW conjugated isotype control. FIG. 6F. Representative liver tissue from the R1-EnzRFAP xenograft mice served as a negative control. Scale bar, 50 μm.

FIG. 8A. 384 clones were tested for hFAP selectivity by ELISA. ScFv expressed in cell supernatant was added to protein coated plates. ScFv binding was detected using a peroxidase conjugated HA-tag monoclonal antibody. 35 clones with a high ELISA signal were identified. FIG. 8B. ScFv expressed in cell supernatant was serial diluted from 1-0.05 (relative concentration) and added to protein coated plates. The amount of scFv bound to hFAP was determined by ELISA. 21 clones demonstrated saturating signals. FIG. 8C. 12 scFv clones with unique sequences were tested for hDPP-IV selectivity by ELISA. scFv expressed in cell supernatant was added to protein coated plates. The threshold for binding signal was set at 0.1 (blue dashed line) and 4 scFv clones showed a low ELISA signal. FIG. 8D. The 4 scFvs were cloned, expressed, purified, and labeled with Alexa Fluor 488. Clone B12 was the only clone with selectivity for FAP-expressing cells but not the parental FAP negative cells when analyzed by flow cytometry. Transduced (blue and orange) and parental (red) cell lines were stained with 0 nM or 500 nM of scFv. Unstained R1-EnzR$^{FAP}$ cells (blue) were used as a negative control.

FIG. 10A-FIG. 10B show sequence alignments of portions of anti-FAP antibodies B12 IgG, ESC11, ESC14, F19, and MFP5. FIG. 10A. Sequence alignments of portions of the light chains of the anti-FAP antibodies. FIG. 10B. Sequence alignments of portions of the heavy chains of the anti-FAP antibodies.

FIG. 11B shows schematics of the NK92MI$^{CD64}$ docking platform and its use.

FIG. 13A. NK92MI$^{CD64}$ cells were preincubated in serum free media for 2 hours. NK92MI$^{CD64}$ were incubated with hPrCSC-44 (FAP+) target cells, loaded with fluorescence enhancing ligand, BATDA, at an E:T ratio of 20:1 (1.6×10$^5$ cells: 8×10$^3$ cells) and anti-FAP mAb at the indicated concentrations at 37° C. for 2 hours. After co-incubation, cytotoxicity was determined by the Dissociation-Enhanced Lanthanide Fluorescent Immunoassay (DELFIA) EuTDA cell cytotoxicity assay (PerkinElmer, Inc., Waltham, Mass.). Data are represented as percent (%) specific release and the mean±SEM of three independent experiments is shown. FIG. 13B. NK92MI$^{CD64}$ cells were preincubated in serum free media for 2 hours. NK92MI$^{CD64}$ cells were incubated with DU145, a FAP negative cell line, at an E:T ratio of 20:1 (1.6×10$^5$ cells: 8×10$^3$ cells) and anti-FAP mAb (5 ug/mL) at 37° C. for 2 hours. After co-incubation, cytotoxicity was determined by the DELFIA EuTDA cell cytotoxicity assay (PerkinElmer, Inc., Waltham, Mass.). Data are represented as % specific release and the mean±SEM of three independent experiments is shown.

FIG. 15A. NK92MI$^{CD64}$ cells were preincubated with or without anti-FAP mAb (5 ug/mL) in serum free media for 2 hours at 37° C. Effector cells were washed and incubated with hPrCSC-44 (FAP+) target cells, loaded with BATDA ligand, at the indicated E:T ratios for 2 hours at 37° C. After co-incubation, cytotoxicity was determined by the DELFIA EuTDA cell cytotoxicity assay (PerkinElmer, Inc., Waltham, Mass.). Data are represented as % specific release and the mean±SEM of three independent experiments is shown. Statistical significance is indicated as  p<0.01, * p<0.001. FIG. 15B. By switching the targeting mAb to an isotype control, the cytotoxic effect drops to baseline levels. The experiment was repeated as previously described except the NK92MI$^{CD64}$ cells were preincubated with or without a human IgG isotype control mAb (5 ug/mL) in serum free media for at 37° C. for 2 hours. Data are represented as % specific release and the mean±SEM of three independent experiments is shown.

DETAILED DESCRIPTION OF ILLUSTRATIVE EMBODIMENTS

Figure 1A:
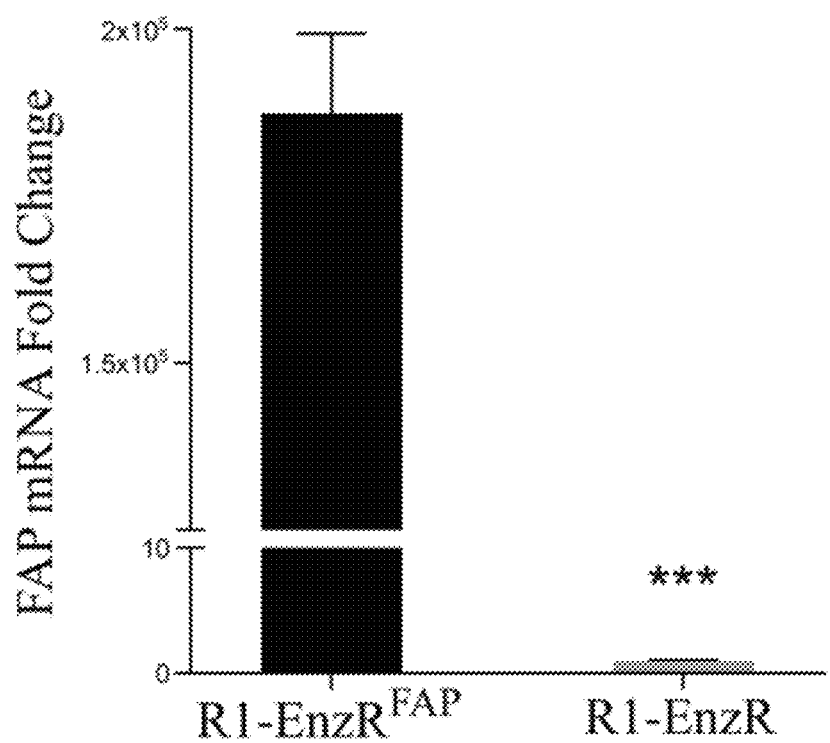
FIG. 1A-FIG. 1C show validation of FAP expression in a newly generated FAP-expressing cell line.

This disclosure describes a compound that binds to fibroblast activation protein alpha (FAP), compositions including the compound, and methods of using the compound and compositions.

Compound

In one aspect, this disclosure describes a compound that binds to FAP. In some embodiments, the FAP includes human FAP, mouse FAP, or both. In some embodiments, the compound may preferably include an antibody. In some embodiments, the compound may preferably include a monoclonal antibody. In some embodiments, the compound may include B12 IgG or a fragment thereof. B12 IgG, a monoclonal antibody, is, as characterized in Example 1, able to selectively bind both recombinant human and murine FAP in vitro.

In some embodiments, wherein the compound that binds to FAP includes an antibody (including, for example, B12 IgG), the antibody may be an isolated antibody. In some embodiments, the antibodies may be isolated or purified by conventional immunoglobulin purification procedures, such as protein A- or G-Sepharose, hydroxylapatite chromatography, gel electrophoresis, dialysis, or affinity chromatography.

In some embodiments, the compound that binds to FAP may be a humanized antibody. An antibody that binds to FAP may be humanized by any suitable method. Techniques for producing humanized monoclonal antibodies may be found, for example, in Jones et al. 1986 Nature 321:522 and Singer et al. 1993 J. Immunol. 150:2844. For example, humanization of the antibody may include changes to the antibody to reduce the immunogenicity of the antibody when used in humans.

Commercial services are available to undertake humanization of an antibody including, for example, Creative Biolabs, Shirley, N.Y.; Fusion Antibodies, Belfast, Northern Ireland; Proteogenix, Schiltigheim, France; Absolute Antibody Ltd, Oxford, UK; GenScript, Piscataway, N.J.; and Precision Antibody, Columbia, Md.

In some embodiments, a humanized antibody that binds to FAP may include at least a portion of an immunoglobulin constant region (Fc) of a human immunoglobulin. The constant region of a humanized monoclonal antibody may belong to any isotype. It may be, for example, the constant region of human IgG. A humanized antibody that binds to FAP may include, in some embodiments, a human immunoglobulin (recipient antibody) in which residues from one or more complementary determining regions (CDRs) of the recipient antibody are replaced by residues from one or more CDRs of a non-human species antibody (donor antibody), such as mouse, rat, or rabbit antibody, that binds to FAP. In some embodiments, Fv framework residues of a human immunoglobulin may be replaced by corresponding non-human residues from an antibody that binds to FAP.

In some embodiments, the compound that binds to FAP includes a chimeric antibody, that is, an antibody in which different portions are derived from different animal species. A chimeric antibody may be obtained by, for example, splicing the genes from a mouse antibody molecule with appropriate antigen specificity together with genes from a human antibody molecule of appropriate biological specificity. See, for example, Takeda et al. 1985 Nature 314:544.

In some embodiments, the compound that binds to FAP binds to a FAP polypeptide. In some embodiments, the FAP polypeptide is human FAP (Gene ID: 2191) or a fragment thereof. In some embodiments, the FAP polypeptide is mouse FAP (Gene ID: 14089) or a fragment thereof. In some embodiments, the compound recognizes a non-reduced FAP polypeptide.

In some embodiments, a compound that binds to FAP may include a derivative of an antibody that is modified or conjugated by the covalent attachment of any type of molecule to the antibody. Such antibody derivatives include, for example, antibodies that have been modified by glycosylation, acetylation, pegylation, phosphorylation, amidation, derivatization by known protecting/blocking groups, proteolytic cleavage, toxins, or linkage to a cellular ligand or other protein. Any of numerous chemical modifications may be carried out by known techniques, including, but not limited to, specific chemical cleavage, acetylation, formylation, and metabolic synthesis of tunicamycin. Additionally, the derivatives may contain one or more non-classical amino acids.

A compound that binds to FAP may be coupled directly or indirectly to a detectable marker by techniques well known in the art. A detectable marker is an agent detectable, for example, by spectroscopic, photochemical, biochemical, immunochemical, or chemical means. Useful detectable markers include, but are not limited to, fluorescent dyes, chemiluminescent compounds, radioisotopes, electron-dense reagents, enzymes, coenzymes, colored particles, biotin, or dioxigenin. A detectable marker often generates a measurable signal, such as radioactivity, fluorescent light, color, or enzyme activity. Antibodies conjugated to detectable agents may be used for diagnostic or therapeutic purposes. Examples of detectable agents include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody or indirectly, through an intermediate such as, for example, a linker known in the art, using techniques known in the art. See, for example, U.S. Pat. No. 4,741,900, describing the conjugation of metal ions to antibodies for diagnostic use. Examples of suitable enzymes include horseradish peroxidase, alkaline phosphatase, beta-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a luminescent material includes luminol; examples of bioluminescent materials include luciferin, and aequorin; and examples of suitable radioactive material include iodine ($^{121}$I, $^{123}$I, $^{125}$I, $^{131}$I), carbon ($^{14}$C), sulfur ($^{35}$S), tritium (3H), indium ($^{111}$In, $^{112}$In, $^{113m}$In, $^{115m}$In), technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, and $^{97}$Ru. Techniques for conjugating such therapeutic moieties to antibodies are well-known.

An intact antibody molecule has two heavy (H) chain variable regions (abbreviated herein as $V_H$) and two light (L) chain variable regions (abbreviated herein as $V_L$). The $V_H$ and $V_L$ regions can be further subdivided into regions of hypervariability, termed "complementarity determining regions" ("CDRs"), interspersed with regions that are more conserved, termed "framework regions" ("FRs"). The extent of the FRs and CDRs has been precisely defined (see, Kabat et al. (1991) Sequences of Proteins of Immunological Interest, Fifth Edition, U.S. Department of Health and Human Services, NIH Publication No. 91-3242, and Chothia et al. 1987 *J. Mol. Biol.* 196: 901-917). Each $V_H$ and $V_L$ is composed of three CDRs and four FRs, arranged from amino-terminus to carboxy-terminus in the following order: FR1, CDR1, FR2, CDR2, FR3, CDR3, FR4.

In some embodiments, a compound that binds to FAP includes a monoclonal antibody having the same heavy chain as B12 IgG. In some embodiments, a compound that binds to FAP includes a monoclonal antibody having the same light chain as B12 IgG. Additionally or alternatively, in some embodiments, a compound that binds to FAP includes a monoclonal antibody having the same heavy chain and the same light chain B12 IgG. In some embodiments, a monoclonal antibody can contain one, two, three, four, five, six, or more amino acid substitutions in the heavy and/or the light chains identified above wherein the amino acid substitutions do not substantially affect binding of the antibody to FAP.

In some embodiments, a compound that binds to FAP includes B12 IgG. In some embodiments, a compound that binds to FAP includes an antibody that binds to the same FAP epitope as B12 IgG.

In some embodiments, a compound that binds to FAP includes a monoclonal antibody having the same $V_H$ domain as B12 IgG. In some embodiments, a compound that binds to FAP includes a monoclonal antibody having the same $V_L$ domain as B12 IgG. In some embodiments, a compound that binds to FAP includes a monoclonal antibody having the same $V_H$ domain and the same $V_L$ domain as a B12 IgG. In some embodiments, a monoclonal antibody can contain one, two, three, four, five, six, or more amino acid substitutions in the $V_H$ domains and/or the $V_L$ domains identified above which do not substantially affect binding of the antibody to FAP.

Table 1 shows the sequences of the $V_H$ domain of B12 IgG and $V_L$ domain of B12 IgG (with the CDRs of each domain in bold) and the CDRs of the light chain (CDR L1, CDR L2, and CDR L3) and the heavy chain (CDR H1, CDR H2, and CDR H3) of B12 IgG.

In some embodiments, a compound that binds to FAP includes an amino acid sequence at least 75%, at least 80%, at least 85%, at least 90%, at least 95%, at least 96%, at least 97%, at least 98%, or at least 99% identical to the amino acid sequence of the $V_H$ domain of B12 IgG (SEQ ID NO:2). Additionally or alternatively, in some embodiments, a compound that binds to FAP includes an amino acid sequence at least 75%, at least 80%, at least 85%, at least 90%, at least 95%, at least 96%, at least 97%, at least 98%, or at least 99% identical to the amino acid sequence of the $V_L$ domain of B12 IgG (SEQ ID NO:1).

In some embodiments, a compound that binds to FAP includes at least one CDR of B12 IgG. In some embodiments, a compound that binds to FAP includes at least two CDRs of the $V_H$ domain of B12 IgG. In some embodiments, a compound that binds to FAP includes at least three CDRs of the $V_H$ domain of a B12 IgG. Additionally or alternatively, in some embodiments a compound that binds to FAP includes at least one CDR of the $V_L$ domain of B12 IgG. In some embodiments, a compound that binds to FAP includes at least two CDRs of the $V_L$ domain of B12 IgG. In some embodiments, a compound that binds to FAP includes at least three CDRs of the $V_L$ domain of B12 IgG. In some embodiments, a compound that binds to FAP includes one, two, three, four, five, six, or more amino acid substitutions in one or more CDRs identified above which do not substantially affect binding of the compound to FAP.

In some embodiments, where a compound that binds to FAP includes a monoclonal antibody, the monoclonal antibody can contain one, two, three, four, five, six, or more amino acid substitutions in one or more framework regions (FRs). In some embodiments, the substitutions or substitutions in the framework regions (FRs) do not substantially affect binding of the antibody to FAP.

In some embodiments, a compound that binds to FAP includes an amino acid sequence that is at least 75%, at least 80%, at least 85%, at least 90%, at least 95%, at least 96%, at least 97%, at least 98%, or at least 99% identical to an amino acid sequence of at least one CDR, at least two CDRs, or at least three CDRs of the $V_H$ domain of B12 IgG (SEQ ID NO:6, SEQ ID NO:7, and SEQ ID NO:8), as shown in Table 1.

In some embodiments, a compound that binds to FAP includes an amino acid sequence that is at least 75%, at least 80%, at least 85%, at least 90%, at least 95%, at least 96%, at least 97%, at least 98%, or at least 99% identical to an amino acid sequence of at least one CDR, at least two CDRs, or at least three CDRs of the $V_L$ domain of B12 IgG (SEQ ID NO:3, SEQ ID NO:4, and SEQ ID NO:5), as shown in Table 1.

In embodiments where the compound that binds to FAP is an antibody, the antibody may be an antibody from any suitable species. In some embodiments, the antibody may be a human antibody. In some embodiments, the antibody may be a mouse antibody. In some embodiments, the antibody may be a rat antibody. In some embodiments, the antibody may be a rabbit antibody.

In some embodiments, the antibody is an IgG antibody. In some embodiments, the antibody may be an antibody or an IgG subclass including, for example, IgG1, IgG2, IgG3 or IgG4. In some embodiments, the antibody may be a mouse IgG of one of the following sub-classes: IgG1, IgG2A, IgG2B, IgG2C and IgG3. In some embodiments, the antibody may be a rat IgG of one of the following sub-classes: IgG1, IgG2A, IgG2B, or IgG2C.

In some embodiments, the antibody may include a kappa light chain. In some embodiments, the antibody may include a lambda light chain.

In some embodiments, a compound that binds to FAP includes variants of B12 IgG; a fragment of B12 IgG; peptibodies and variants of B12 IgG; multispecific antibodies (for example, bispecific antibodies) formed from at least two intact antibodies at least one of which is B12 IgG; humanized B12 IgG; and antibody mimetics that mimic the structure and/or function of B12 IgG or a specified fragment or portion thereof, including single chain antibodies, single-domain antibodies, and fragments thereof.

In some embodiments, a compound that binds to FAP includes a bispecific or a bifunctional antibody. A bispecific or bifunctional antibody is an artificial hybrid antibody having two different heavy/light chain pairs and two different binding sites. A bispecific antibody may be produced by a variety of methods including fusion of hybridomas or linking of F(ab') fragments. See, for example, Songsivilai et al. 1990 *Clin. Exp. Immunol.* 79:315; Kostelny et al. 1992 *J. Immunol.* 148:1547. In addition, bispecific antibodies may be formed as "diabodies" (Holliger et al. 1993 *PNAS* USA 90:6444) or "Janusins" (Traunecker et al. 1991 *EMBO J.* 10:3655; Traunecker et al. 1992 *Int. J Cancer Suppl.* 7:51).

In another aspect, this disclosure describes an isolated polynucleotide molecule. In some embodiments, the isolated polynucleotide molecule includes a nucleotide sequence encoding the compound that binds to FAP. In some embodiments, the isolated polynucleotide molecule includes a nucleotide sequence that has at least 75%, at least 80%, at least 85%, at least 90%, at least 95%, at least 96%, at least 97%, at least 98%, or at least 99% sequence identity to nucleotide sequence encoding an antibody described herein. In some embodiments, the isolated polynucleotide molecule includes polynucleotides that hybridize under high stringency to a nucleotide sequence encoding an antibody or a complement thereof. As used herein "stringent conditions" refer to the ability of a first polynucleotide molecule to hybridize, and remain bound to, a second, filter-bound polynucleotide molecule in 0.5 M $NaHPO_4$, 7% sodium dodecyl sulfate (SDS), and 1 mM EDTA at 65° C., followed by washing in 0.2×SSC/0.1% SDS at 42° C. (see Ausubel et al. (eds.), Current Protocols in Molecular Biology, Vol. 1, Green Publishing Associates, Inc., and John Wiley & Sons, Inc., N.Y. (1989), at p. 2.10.3). In some embodiments, the isolated polynucleotide molecule includes polynucleotides that encode one or more of the CDRs or the heavy and/or light chains of a B12 IgG. General techniques for cloning and sequencing immunoglobulin variable domains and constant regions are well known. See, for example, Orlandi et al. 1989 *Proc. Nat'l Acad. Sci. USA* 86:3833.

In another aspect, this disclosure describes recombinant vectors including an isolated polynucleotide of the present invention. The vector may be, for example, in the form of a plasmid, a viral particle, or a phage. The appropriate DNA sequence may be inserted into a vector by a variety of procedures. In general, the DNA sequence is inserted into an appropriate restriction endonuclease site(s) in a vector by procedures known in the art. Such procedures are deemed to be within the scope of those skilled in the art. Large numbers of suitable vectors and promoters are known to those of skill in the art and are commercially available. The following vectors are provided by way of example. Bacterial vectors include, for example, pQE70, pQE60, pQE-9, pBS, pD10, phagescript, psiX174, pbluescript SK, pbsks, pNH8A, pNH16a, pNH18A, pNH46A, ptrc99a, pKK223-3, pKK233-3, pDR540, and pRIT5. Eukaryotic vectors include, for example, pWLNEO, pSV2CAT, pOG44, pXT1, pSG, pSVK3, pBPV, pMSG, and pSVL. However, any other plasmid or vector may be used.

In a further aspect, this disclosure also includes a host cell containing at least one of the above-described vectors. The host cell may be a higher eukaryotic cell, such as a mammalian or insect cell, or a lower eukaryotic cell, such as a yeast cell. Or, the host cell may be a prokaryotic cell, such as a bacterial cell, or a plant cell. Introduction of a vector construct into the host cell may be effected by any suitable techniques, such as, for example, calcium phosphate transfection, DEAE-Dextran mediated transfection, or electroporation. (Davis et al., Basic Methods in Molecular Biology (1986)).

Also included in the present invention are phage display libraries expressing one or more hypervariable regions from an antibody of the present invention including, for example B12 IgG, and clones obtained from such a phage display library. Phage display libraries may be prepared, for example, using the Pн.D.-7 Phage Display Peptide Library Kit (Catalog #E8100S) or the Pн.D.-12 Phage Display Peptide Library Kit (Catalog #E8110S) available from New England Biolabs Inc., Ipswich, Mass. See, for example, Smith et al. 1997 *Chem Rev.* 97:391-410.

Recombinant Antibodies

A monoclonal antibody of the present disclosure may be produced by any suitable recombinant technique including, for example, by phage display or by combinatorial methods. See, for example, U.S. Pat. No. 5,223,409; WO 92/18619; WO 91/17271; WO 92/20791; WO 92/15679; WO 93/01288; WO 92/01047; WO 92/09690; or WO 90/02809.

Example 1 describes the development of a cross-reactive chimeric monoclonal antibody to detect the activated stroma in solid tumors. The antibody was developed using a naïve murine scFv antibody phage display library. When the (murine) scFv produced by clone B12 were engineered into a full-length human IgG construct, B12 IgG, the resulting antibody was found to selectively bind both recombinant human and murine FAP in vitro. Based on these findings, B12 IgG was evaluated as a near-infrared (NIR) optical imaging probe in vivo using preclinical prostate cancer murine models. B12 IgG detects FAP, a serine protease highly expressed on cancer-associated fibroblasts (CAFs) in 90% of epithelial tumors. Prostate cancer was selected as a model because CAFs contribute significantly to the survival and growth of the disease. CAFs are found in prostatic intraepithelial neoplasia which is considered to be precancerous disease, and CAFs have been shown to play an essential role in early prostate cancer tumorigenesis. As the cancer evolves, the abetting stromal microenvironment contributes to immune evasion and therapeutic resistance. Prostate cancer tumors have a high stromal composition compared to other solid tumors, and the presence of a highly reactive stroma enriched with CAFs directly correlates with cancer progression, metastasis, and poor clinical outcome.

Example 1 also shows that the imaging properties of B12 IgG in vivo were favorable for detection of hFAP expressed on the surface of cancer cells in a tumor xenograft model. B12 IgG demonstrated high tumor uptake and retention in the positive control xenografts (R1-EnzR$^{FAP}$ which were lentivirally transduced to express hFAP) by NIR imaging. Detection of B12 IgG bound to FAP at 144 hours by immunohistochemistry (IHC) staining of R1-EnzR$^{FAP}$ xenografts further validated the selectivity and retention properties of the antibody. A fluorescence signal was also detected by NIR imaging in the parental xenografts. Detection of mFAP mRNA expression in both xenografts by quantitative RT-PCR further validated the presence of murine origin stromal cells within the tumor xenografts. These results suggest that human prostate cancer xenografts recruit murine FAP$^+$-stromal cells to the tumor site.

TABLE 1

| | | |
|---|---|---|
| $V_L$ domain of B12 IgG | DIVITQSPSSLSASLGERVSLTCR ASQEISGYLSWLQQKPDGTIKLIY AASTLDSGVPKRFSGSRSGSDYSL TISSLESEDFADYYCLQYASYPWT FGGGTKLEIKR | SEQ ID NO: 1 |
| B12 IgG light chain CDR1 | RASQEISGYLS | SEQ ID NO: 3 |
| B12 IgG light chain CDR2 | AASTLDS | SEQ ID NO: 4 |
| B12 IgG light chain CDR3 | LQYASYPWT | SEQ ID NO: 5 |
| $V_H$ domain of B12 IgG | EVMLVESGGGLVQPGGSLKLSCAA SGFTFSSYGMSWVRQTPDKRLELV ATINSNGGSTYYPDSVKGRFTISR DNAKNTLYLQMSSLKSEDTAMYYC ARDYFDYWGQGTTLTVSS | SEQ ID NO: 2 |
| B12 IgG heavy chain CDR1 | GFTFSSYGMS | SEQ ID NO: 6 |
| B12 IgG heavy chain CDR2 | TINSNGGSTYYPDSVKG | SEQ ID NO: 7 |
| B12 IgG heavy chain CDR3 | DYFDY | SEQ ID NO: 8 |

Figure 7:
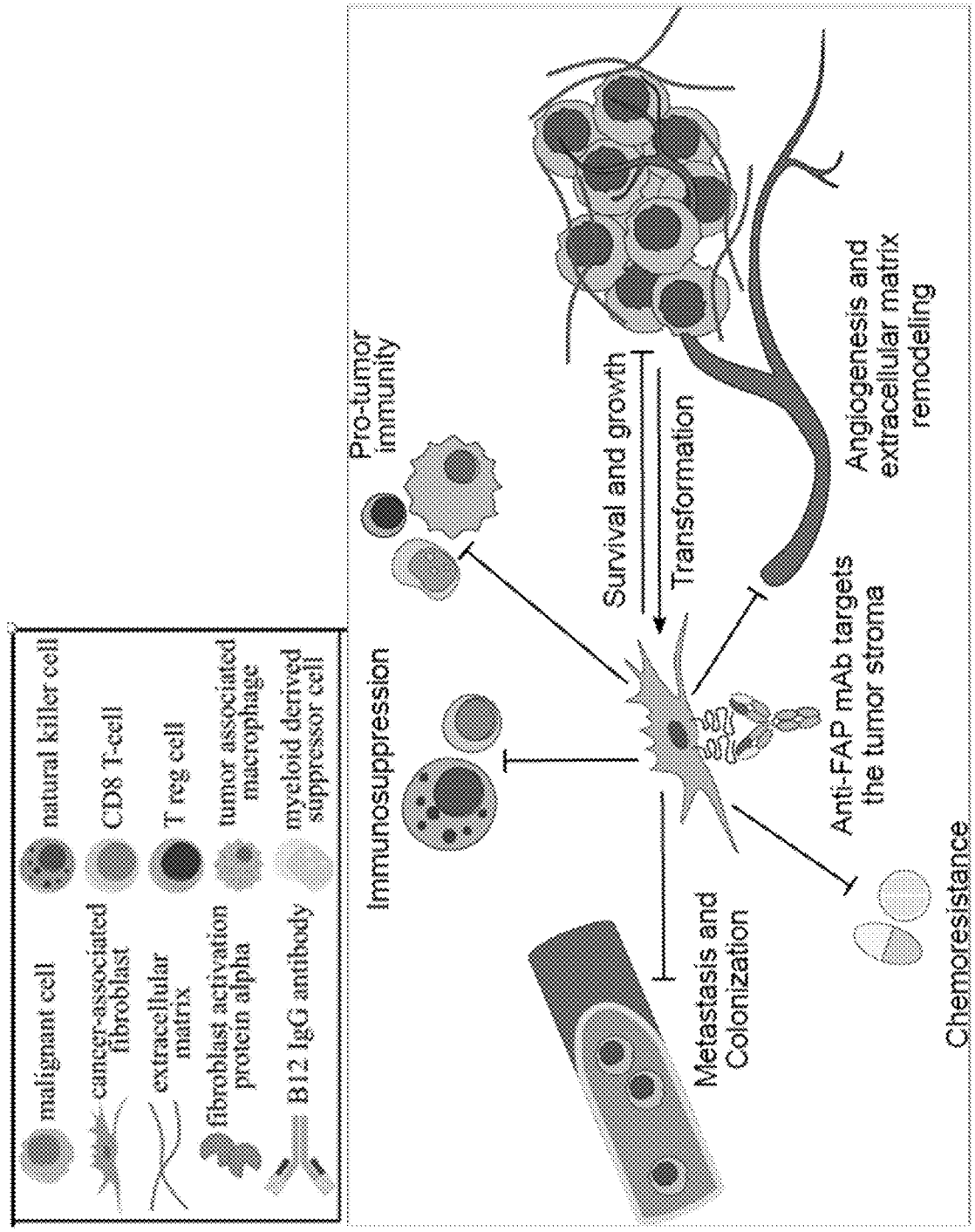
FIG. 7 shows a schematic of anticipated effects of the anti-FAP monoclonal antibody B12 IgG in a tumor microenvironment.

Because CAF enriched reactive stroma is detected in the early stages of tumorigenesis, FAP imaging could play a key role in diagnosis and staging of the disease. Visualizing tumor margins using non-invasive imaging will aid in the development of a tailored therapeutic regimen and may even be able to detect early sites of metastasis. Several studies have detected CAFs in groups of circulating tumor cells and in early metastatic lesion formation. Since FAP-expressing CAFs are recruited to metastases, FAP imaging could be used to evaluate patient response to therapy and manage ongoing care. FIG. 7 shows a schematic of anticipated effects of the anti-FAP monoclonal antibody B12 IgG in a tumor microenvironment.

Prior Anti-FAP Antibodies and Small Molecules

Other FAP-targeted therapies using antibodies or small molecules were known at the time of the invention. (See, e.g., Wang et al. 2014 *Cancer Immunol. Res.* 2, 154-166; Welt et al. 1994 *J. Clin. Oncol.* 12, 1193-1203; Loktev et al. 2018 *J. Nucl. Med.* 59, 1423-1429; Li et al. 2012 *Bioconjugate Chem.* 23, 1704-1711; Lo et al. 2009 *J. Med. Chem.* 52, 358-368; Ruger et al. 2014 *J. Control. Release.* 186, 1-10; Fischer et al. 2012 *Clin. Cancer Res.* 18, 6208-6218; Narra et al. 2007. *Cancer Biol. Ther.* 6, 1691-1699; LeBeau et al. 2009 *Mol. Cancer Ther.* 8, 1378-1386; Ostermann et al. 2008 *Clin. Cancer Res.* 14, 4584-4592.)

Fluorescence-activatable liposome bearing FAP antibody fragments (Ruger et al. 2014 *J. Control. Release.* 186, 1-10), FAP-activated fluorescent probes (Li et al. 2012 *Bioconjugate Chem.* 23, 1704-1711; Lo et al. 2009 *J. Med. Chem.* 52, 358-368), and radiolabeled small molecule FAP inhibitors (Loktev et al. 2018 *J. Nucl. Med.* 59, 1423-1429) for diagnostic imaging had also been generated at the time of the invention.

Each of these other antibodies and small molecules have drawbacks as a therapeutic, however.

For example, the FAP antibody fragments developed by Ruger et al., the FAP-activated fluorescent probes of Li et al., and the radiolabeled small molecule FAP inhibitors of Loktev et al. were developed specifically for imaging FAP and the tumor microenvironment, not as a therapeutic. Like the FAP-activated fluorescent probes of Li et al., the FAP antibody fragments of Ruger et al. require FAP activity to active the fluorescent probes used for imaging. When small molecule FAP inhibitors were tested as therapeutics, no clinical response was seen. (Narra et al. 2007 *Cancer Biology & Therapy* 6:11, 1691-1699.) Moreover, such fragments and small molecules do not have the therapeutic potential of an antibody.

The existing anti-FAP antibodies also exhibited drawbacks. For example, the first generation monoclonal FAP antibody, F19, and its humanized form (sibrotuzumab) were eventually withdrawn from clinical trials when no therapeutic benefit was observed. F19 also failed to demonstrate internalization properties (that is, internalization by FAP-expressing cells) and cross-reactivity with mFAP. (See Welt et al. 1994 *J. Clin. Oncol.* 12, 1193-1203; Mersmann et al. 2001, *Int. J. Cancer* 15, 240-248; Scott et al. 2003. *Clin. Cancer Res.* 9, 1639-1647; Hofheinz et al. 2003 *Onkologie.* 26, 44-48; U.S. Pat. No. 6,455,677).

F19 and other previously developed antibodies that do not cross-react with mFAP (see, e.g., Schuberth et al. 2013 *J. Transl. Med.* 11, 187) cannot be used for testing in preclinical syngeneic murine models. Cross-reactivity with the mouse homolog is used to evaluate new imaging and therapeutic agents in preclinical models, especially when targeting mouse-origin tumor stroma. Cross-reactivity with the mouse homolog is also important in determining off-target effects caused by antigen-dependent accumulation in host tissue.

Other antibodies that have been developed only recognize mFAP (and not hFAP). (See, e.g., Wang et al. 2014. *Cancer Immunol. Res.* 2, 154-166.) Such antibodies have limited clinical applications and can only be used for proof-of-concept models.

Another anti-FAP monoclonal antibody, FAP5 (see Ostermann et al. 2008 *Clin. Cancer Res.* 14, 4584-4592; U.S. Pat. No. 8,568,727) was shown to be cross-reactive with mouse and human FAP; however, when the antibody was used in CAR T cell mouse experiments, the therapy triggered recognition of multipotent bone marrow stromal cells and cachexia. FAP5 was determined to be targeting FAP-expressing cells in the bone and causing the toxicity. Other research groups using other anti-FAP antibodies did not see toxicity in similar studies suggesting that the side effects of FAP5 were due to an off-tumor effect of the antibody. It is also unknown if FAP5 is internalized by FAP-expressing cells.

Additional anti-FAP antibodies, ESC11 and ESC14 (see Fischer et al. 2012 *Clin. Cancer Res.* 18, 6208-6218; U.S. Pat. No. 8,999,342) were developed for radioimmunotherapy. These antibodies were tested in a FAP-expressing melanoma xenograft model. This approach leads to an overestimation of in vivo targeting potential and exaggerated efficacy-to-tolerability ratios not confirmed in subsequent clinical studies. Moreover, these antibodies have not been shown to localize to a metastatic tumor in an in vivo model In contrast to a FAP-expressing melanoma xenograft model, testing of antibody binding to endogenous murine origin stroma, as described in Example 1, provides a more realistic evaluation of the potency and selectivity of the antibody. Moreover, an antibody that recognizes human and murine FAP is preferred over antibodies that only recognize mouse FAP (which cannot be developed as a therapeutic or diagnostic agent for humans) and over antibodies that only recognize human FAP (which cannot be used to test for off-tumor effects in murine models).

B12 IgG

As further described in Example 1, B12 IgG is a potent and selective antibody for human FAP and murine FAP. This cross-reactivity with the mouse homolog allows the imaging and therapeutic potential of B12 IgG to be evaluated in preclinical models, especially targeting of the mouse-origin tumor stroma. Cross-reactivity with the mouse homolog may also be important in evaluating off-target effects and in accurately assessing antibody distribution in syngeneic murine models of localized and advanced disease.

As further described in Example 1, confocal microscopy analysis showed that B12 IgG is internalized through a FAP-dependent mechanism. Antibody internalization is an important mechanism that may be exploited for the development of antibody-drug conjugate or radioimmunotherapy agents; concentrating chemotherapies or radio isotopes in tumor cells has been shown to increase therapeutic response in patients.

Also described in Example 1, B12 IgG was able to detect FAP in in vivo models of metastatic tumors.

Compositions

In some embodiments, this disclosure describes a composition including a compound that binds to FAP as described herein.

In some embodiments, the composition may also include, for example, buffering agents to help to maintain the pH in an acceptable range or preservatives to retard microbial growth. A composition may also include, for example, carriers, excipients, stabilizers, chelators, salts, or antimicrobial agents. Acceptable carriers, excipients, stabilizers, chelators, salts, preservatives, buffering agents, or antimicrobial agents, include, but are not limited to, buffers such as phosphate, citrate, and other organic acids; antioxidants including ascorbic acid and methionine; preservatives, such as sodium azide, octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol; polypeptides; proteins, such as serum albumin, gelatin, or non-specific immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (for example, Zinc (Zn)-protein complexes); and/or non-ionic surfactants such as TWEEN, PLURONICS, or polyethylene glycol (PEG).

In some embodiments, the composition is a pharmaceutical composition and includes the monoclonal antibody and a pharmaceutically acceptable carrier, diluent or excipient. In the preparation of the pharmaceutical compositions comprising the antibodies described in the teachings herein, a variety of vehicles and excipients may be used, as will be apparent to the skilled artisan.

The pharmaceutical compositions will generally comprise a pharmaceutically acceptable carrier and a pharmacologically effective amount of an antibody, or mixture of antibodies.

The pharmaceutical composition may be formulated as a powder, a granule, a solution, a suspension, an aerosol, a solid, a pill, a tablet, a capsule, a gel, a topical cream, a suppository, a transdermal patch, and/or another formulation known in the art.

For the purposes described herein, pharmaceutically acceptable salts of an antibody are intended to include any art-recognized pharmaceutically acceptable salts including organic and inorganic acids and/or bases. Examples of salts include but are not limited to sodium, potassium, lithium, ammonium, calcium, as well as primary, secondary, and tertiary amines, esters of lower hydrocarbons, such as methyl, ethyl, and propyl. Other salts include but are not limited to organic acids, such as acetic acid, propionic acid, pyruvic acid, maleic acid, succinic acid, tartaric acid, citric acid, benzoic acid, cinnamic acid, salicylic acid, etc.

As used herein, "pharmaceutically acceptable carrier" comprises any standard pharmaceutically accepted carriers known to those of ordinary skill in the art in formulating pharmaceutical compositions. For example, the antibody may be prepared as a formulation in a pharmaceutically acceptable diluent, including for example, saline, phosphate buffer saline (PBS), aqueous ethanol, or solutions of glucose, mannitol, dextran, propylene glycol, oils (for example, vegetable oils, animal oils, synthetic oils, etc.), microcrystalline cellulose, carboxymethyl cellulose, hydroxylpropyl methyl cellulose, magnesium stearate, calcium phosphate, gelatin, polysorbate 80 or as a solid formulation in an appropriate excipient.

A pharmaceutical composition will often further comprise one or more buffers (for example, neutral buffered saline or phosphate buffered saline), carbohydrates (for example, glucose, sucrose or dextrans), mannitol, proteins, polypeptides or amino acids such as glycine, antioxidants (for example, ascorbic acid, sodium metabisulfite, butylated hydroxytoluene, butylated hydroxyanisole, etc.), bacteriostats, chelating agents such as EDTA or glutathione, adjuvants (for example, aluminium hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

Any suitable carrier known to those of ordinary skill in the art may be employed in a composition including at least one of the antibodies describes herein. Antibody compositions may be formulated for any appropriate manner of administration, including for example, oral, nasal, mucosal, intravenous, intraperitoneal, intradermal, subcutaneous, and intramuscular administration.

Administration and Treatment

A composition of the present disclosure may be formulated in pharmaceutical preparations in a variety of forms adapted to the chosen route of administration. One of skill will understand that the composition will vary depending on mode of administration and dosage unit. For example, for parenteral administration, isotonic saline may be used. For topical administration a cream, including a carrier such as dimethylsulfoxide (DMSO), or other agents typically found in topical creams that do not block or inhibit activity of the peptide, may be used. Other suitable carriers include, but are not limited to alcohol, phosphate buffered saline, and other balanced salt solutions. The compounds of this invention may be administered in a variety of ways, including, but not limited to, intravenous, topical, oral, subcutaneous, intraperitoneal, and intramuscular delivery. In some aspects, the compounds of the present invention may be formulated for controlled or sustained release. In some aspects, a formulation for controlled or sustained release is suitable for subcutaneous implantation. In some aspects, a formulation for controlled or sustained release includes a patch. A compound may be formulated for enteral administration, for example, formulated as a capsule or tablet.

Administration may be as a single dose or in multiple doses. In some embodiments, the dose is an effective amount as determined by the standard methods, including, but not limited to, those described herein. Those skilled in the art of clinical trials will be able to optimize dosages of particular compounds through standard studies. Additionally, proper dosages of the compositions may be determined without undue experimentation using standard dose-response protocols. Administration includes, but is not limited to, any of the dosages and dosing schedules, dosing intervals, and/or dosing patterns described in the examples included herewith.

A composition including an antibody according to the present disclosure may be administered by any suitable means including, but not limited to, for example, oral, rectal, nasal, topical (including transdermal, aerosol, buccal and/or sublingual), vaginal, parenteral (including subcutaneous, intramuscular, and/or intravenous), intradermal, intravesical, intra-joint, intra-arteriole, intraventricular, intracranial, intraperitoneal, intranasal, by inhalation, or intralesional (for example, by injection into or around a tumor).

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that may be employed will be known to those of skill in the art. Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the FDA. Such preparations may be pyrogen-free.

Many suitable formulations are known, including polymeric or protein microparticles encapsulating drug to be released, ointments, gels, or solutions which may be used topically or locally to administer drug, and even patches, which provide controlled release over a prolonged period of time. These may also take the form of implants. Such an implant may be implanted within the tumor.

The compounds of the present invention may also be provided in a lyophilized form. Such compositions may include a buffer, for example, bicarbonate, for reconstitution prior to administration, or the buffer may be included in the lyophilized composition for reconstitution with, for example, water. The lyophilized composition may further comprise a suitable vasoconstrictor, for example, epinephrine. The lyophilized composition may be provided in a syringe, optionally packaged in combination with the buffer for reconstitution, such that the reconstituted composition may be immediately administered to a patient.

As used herein "treating" or "treatment" may include therapeutic and/or prophylactic treatments. "Treating a disorder," as used herein, is not intended to be an absolute term. Treatment may lead to an improved prognosis or a reduction in the frequency or severity of symptoms. A "therapeutically effective" concentration or amount as used herein is an amount that provides some improvement or benefit to the subject. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis. Likewise, the term "preventing," as used herein, is not intended as an absolute term. Instead, prevention refers to delay of onset, reduced frequency of symptoms, or reduced severity of symptoms associated with a disorder. Prevention therefore refers to a broad range of prophylactic measures that will be understood by those in the art. In some circumstances, the frequency and severity of symptoms is reduced to non-pathological levels. In some circumstances, the symptoms of an individual receiving the compositions of the invention are only 90%, 80%, 70%, 60%, 50%, 40%, 30%, 20%, 10%, 5%, or 1% as frequent or severe as symptoms experienced by an untreated individual with the disorder.

Therapeutically effective concentrations and amounts may be determined for each application herein empirically by testing the compounds in known in vitro and in vivo systems, such as those described herein, dosages for humans or other animals may then be extrapolated therefrom.

It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions and methods.

Toxicity and therapeutic efficacy of the compositions may be determined by standard pharmaceutical procedures in cell cultures or experimental animals, for example, for determining the $LD_{50}$ (the dose lethal to 50% of the population) and the $ED_{50}$ (the dose therapeutically effective in 50% of the population). The dose ratio between toxic and therapeutic effects is the therapeutic index and it may be expressed as the ratio between $LD_{50}$ and $ED_{50}$. Compositions that exhibit high therapeutic indices may be preferred. The data obtained from cell culture assays and animal studies may be used in formulating a range of dosage for use in humans. The dosage of such compositions may preferably lie within a range of circulating concentrations that include the $ED_{50}$ with little or no toxicity. The dosage may vary within this range depending upon the dosage form employed and the route of administration utilized. The exact formulation, route of administration and dosage may be chosen by the individual physician in view of the patient's condition.

A composition as described herein may be administered at once or may be divided into a number of smaller doses to be administered at intervals of time. For example, compositions may be administered repeatedly, for example, at least 2, 3, 4, 5, 6, 7, 8, or more times, or may be administered by continuous infusion. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions and methods.

In some therapeutic embodiments, an "effective amount" of an agent is an amount that results in a reduction of at least one pathological parameter. Thus, for example, in some aspects of the present disclosure, an effective amount is an amount that is effective to achieve a reduction of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% compared to the expected reduction in the parameter in an individual not treated with the agent.

In some aspects of the methods of the present disclosure, a method further includes the administration of one or more additional therapeutic agents. One or more additional therapeutic agents may be administered before, after, and/or coincident to the administration of a monoclonal antibody as described herein. An additional therapeutic agent may include, for example, chemotherapy, radiation therapy, etc. Additional therapeutic agents may be administered separately or as part of a mixture or cocktail. In some aspects of the present disclosure, the administration of an antibody may allow for the effectiveness of a lower dosage of other therapeutic modalities when compared to the administration of the other therapeutic modalities alone, providing relief from the toxicity observed with the administration of higher doses of the other modalities.

In some aspects of the methods of the present disclosure, the administration of a composition as described herein and the at least one additional therapeutic agent demonstrate therapeutic synergy. In some aspects of the methods of the present disclosure, a measurement of response to treatment observed after administering both an antibody as described herein and the additional therapeutic agent is improved over the same measurement of response to treatment observed after administering either the antibody or the additional therapeutic agent alone.

Methods of Using

A compound that binds to FAP as described herein or a composition including such a compound may be used for any suitable application including, for example, as a research tool, in clinical imaging, as a diagnostic agent, as a therapeutic agent, etc. A person having ordinary skill in the art will recognize that these exemplary applications are not mutually exclusive.

In some embodiments, a compound that binds to FAP as described herein may be used as an in vitro and/or in vivo research tool. Uses for such research tools include, for example, Western blot, ELISA, flow cytometry, immunohistochemistry (IHC), and/or animal imaging.

In some embodiments, the compound may be labeled. For example, the compound may be conjugated to a reporter molecule. A reporter molecule may include, for example, an enzyme, a fluorescent dye, an infrared dye, a chemiluminescent reporter, a hapten, etc. Additionally or alternatively, the compound may be detected by use of an additional molecule that is conjugated to a reporter molecule and binds to the compound.

In some embodiments, the compound may be used to label a cell (e.g., a mammalian cell), and the labeled cell may be directly or indirectly imaged via secondary methods.

In some embodiments, a compound that binds to FAP as described herein may be used as a clinical imaging probe. A person having skill in the art can imagine a variety of uses that include an image of a cell expressing FAP. In an exemplary embodiment, FAP imaging could be used to evaluate effectiveness of treatment and manage ongoing care.

In some embodiments, a compound that binds to FAP as described herein could be used in immuno-specific phenotype tumor imaging including, for example, immuno-positron emission tomography (immuno-PET) or PET imaging. (See, e.g., Kraeber-Bodéré et al. 2015, *Int J Mol Sci.* 16(2):3932-3954; Thorek et al. 2016 *Sci. Transl. Med.* 8:367ra167.)

For example, the results of Example 1 show that B12 IgG is sensitive enough to detect small osseous metastatic lesions a few millimeters in size using NIR imaging and potentially other imaging modalities. The positioning of CAFs in the tumor microenvironment make this cell population a desirable target for imaging. The tumor stroma is well vascularized which allows for larger molecules, such as monoclonal antibodies, to access the stromal compartment. In addition, CAFs are genetically stable and retain expression of target antigens more consistently than malignant cells. The ability to target $FAP^+$-CAFs with an imaging probe in the tumor microenvironment may be useful in a number of clinical applications. (See, e.g., Brennen et al. 2012 *Mol. Cancer Ther.* 11, 257-266.) Moreover, because B12 IgG targets the tumor stroma, and not cancer-specific antigens, it can be used as an imaging agent in non-prostate cancers.

Figure 17:
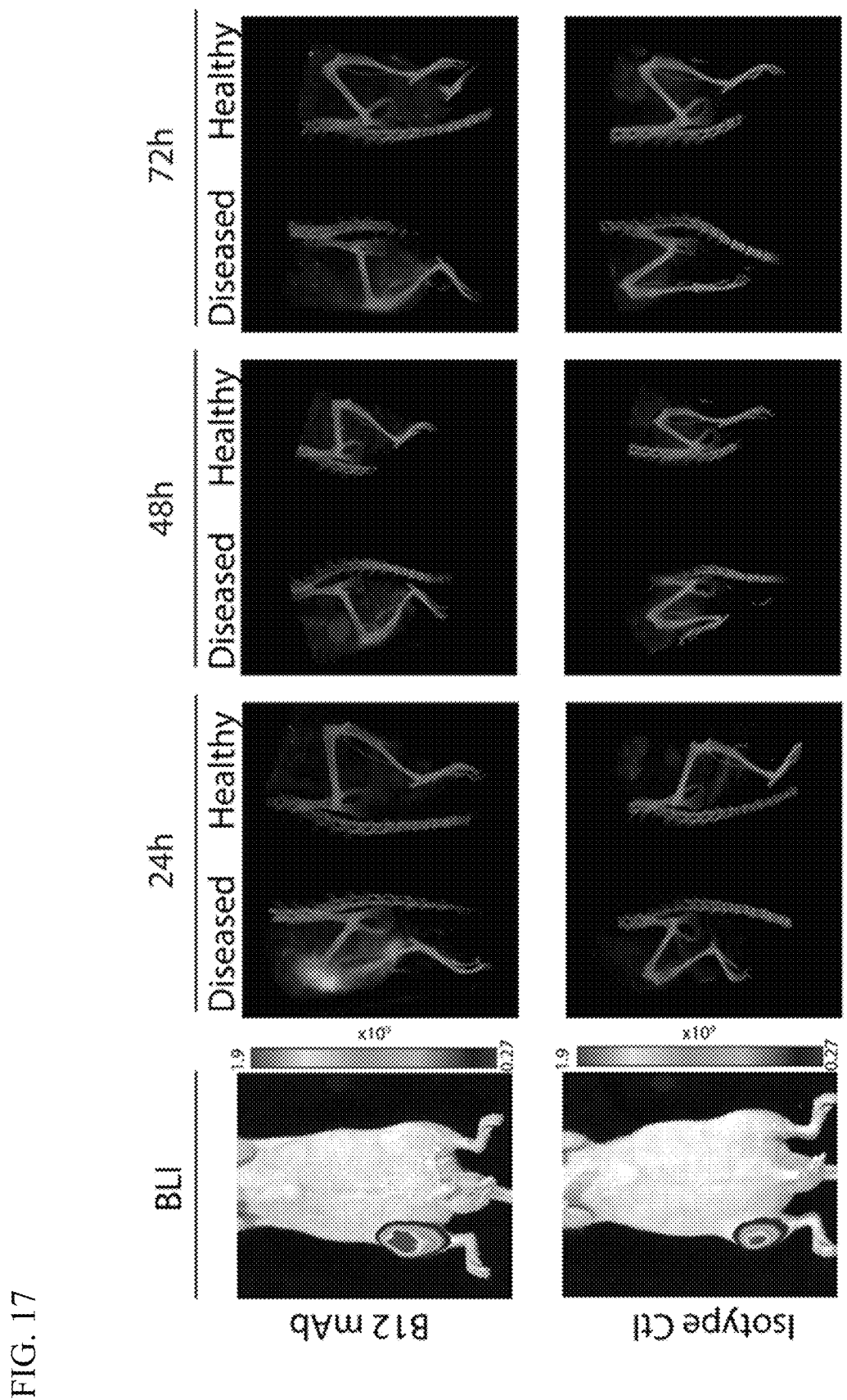
FIG. 17 shows PET/CT images of representative mice bearing CWR-R1-EnzR$^{FAP}$ intra-tibial tumors. Mice received 4.2 MBq of either [$^{89}$Zr]Zr-B12 IgG or [$^{89}$Zr]Zr-IgG via tail vein and were then imaged at 24 hours, 48 hours, and 72 hours.
Figure 18:
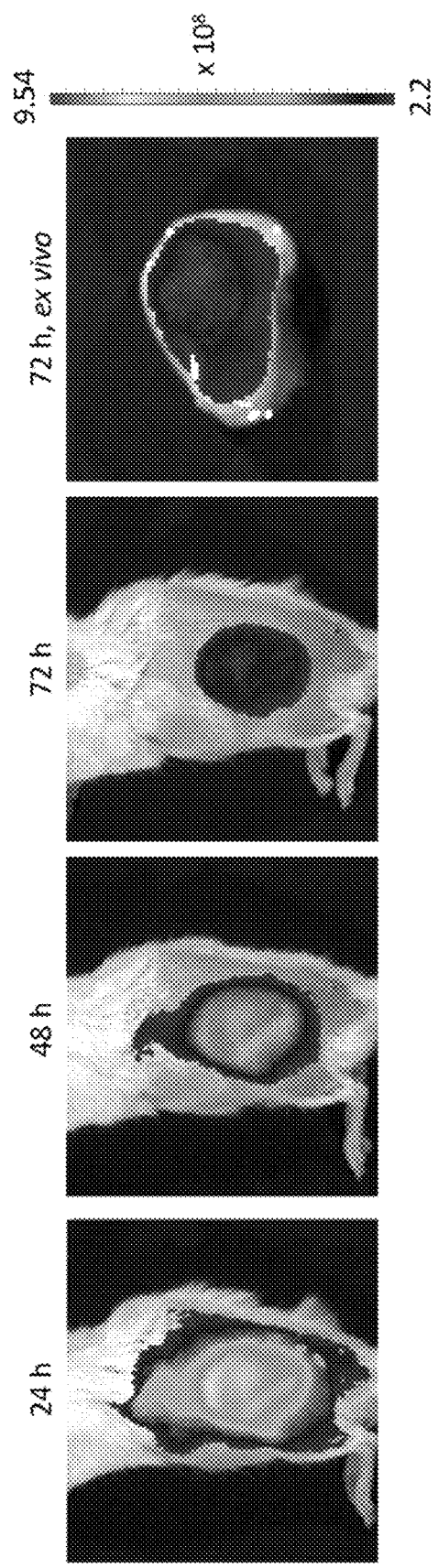
FIG. 18 shows anti-FAP mAb (B12 IgG) localizes to cancer-associated fibroblasts (CAFs) in a xenograft mouse model. Localization of IRDye-800CW conjugated anti-FAP mAb in representative mice bearing FAP-positive cancer associated fibroblast and prostate cancer subcutaneous xenografts. Tumors were imaged ex vivo at 72 hours.

Additionally, Example 2 shows the anti-FAP mAb B12 IgG conjugated to IRDye-800CW can be used to identify the location of tumors in FAP positive-cancer associated fibroblast and prostate cancer subcutaneous xenografts (FIG. 17) and the anti-FAP mAb B12 IgG can selectively detect FAP-positive metastatic prostate cancer tumors by PET/CT imaging after systemic treatment with the mAb (FIG. 18).

In some embodiments, a compound that binds to FAP as described herein may be used as a diagnostic agent.

For example, a compound that binds to FAP as described herein may be used to identify the presence or absence of FAP in a sample from a subject. In some embodiments, identifying the presence of FAP may include identifying an amount and/or a distribution of FAP in a sample from a subject.

Because FAP-enriched reactive stroma develops in early stages of cancer, FAP imaging may play a key role in diagnosis and staging of disease. Visualizing tumor margins using non-invasive imaging may help in developing a treatment plan. Since FAP-expressing cells are recruited to metastatic lesions, a compound that binds to FAP may even be able to detect early sites of metastasis.

In some embodiments, a compound that binds to FAP as described herein may be used as a therapeutic agent.

In some embodiments, a compound that binds to FAP as described herein may preferably target CAFs. As noted above, when small molecule FAP inhibitors were tested as therapeutics, no clinical response was seen. (Narra et al. 2007 Cancer Biology & Therapy 6:11, 1691-1699.) Without wishing to be bound by theory, it is believed that inhibiting FAP activity alone does not have an effect compared to targeting CAFs and disrupting the tumor support system.

In some embodiments, a compound that binds to FAP as described herein may be used in an antibody-targeted therapy. Examples of such therapies may include, for example, an antibody-drug conjugate (ADC), radioimmunotherapy (RIT), immunotherapy for antibody dependent cell mediated cytotoxicity (ADCC), etc. Without wishing to be bound by theory, the ability of B12 IgG to be internalized is believed to make it a promising candidate for use in radioimmunotherapy or as an antibody-drug conjugate.

In some embodiments, a compound that binds to FAP as described herein may be used in a therapy that includes antibody dependent cell mediated cytotoxicity (ADCC). For example, the results of Example 2 show B12 IgG can mediate ADCC (FIG. 13).

For example, in exemplary embodiments, when the compound is used radioimmunotherapy (RIT), RIT may include short-range radiation from β-particles (See, e.g., Kraeber-Bodéré et al. 2015, Int J Mol Sci. 16(2):3932-3954; LeBeau et al. 2013 Cancer Res. 73(7):2070-81) or α-particles See, e.g., Kraeber-Bodéré et al. 2015, Int J Mol Sci. 16(2):3932-3954; McDevitt et al. 2018 Nature Comm. 9:1629).

Figure 11A:
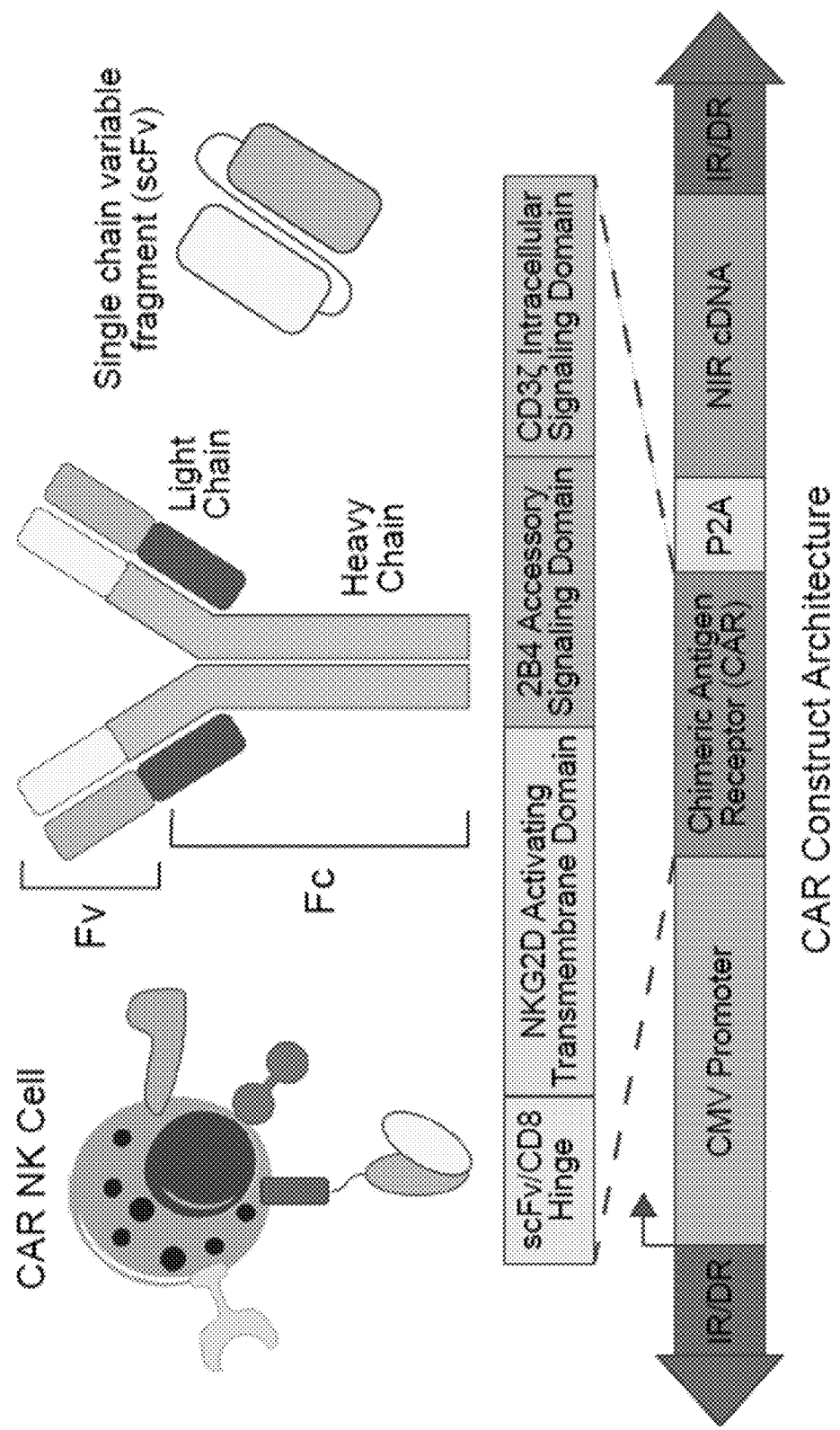
FIG. 11A shows a schematic of an exemplary chimeric antigen receptor (CAR) construct that could be used in a CAR NK cell.

Additionally or alternatively, the compound may be used in a cell-based immunotherapeutic. A cell-based immunotherapeutic may include, for example, a chimeric antigen receptor (CAR) T cell, a CAR natural killer (NK) cell, or a "ready-made CAR" such as an NK92 cell that stably expresses CD64 or an NK92 cell that stably expresses CD16A. In some embodiments, a construct encoding the CAR may include a sequence including a compound that binds to FAP, as described herein, a transmembrane domain, and an intracellular signaling domain to form a FAP-CAR construct. A schematic of an exemplary FAP-CAR for use in an NK cell is shown in FIG. 11. The FAP-CAR construct may be transduced into an NK cell or a T cell. In some embodiments, the NK cell or T cell may be a primary cell. In some embodiments, the NK cell or T cell may originate from a patient to be treated. In some embodiments, the NK cell or T cell may be purified from a healthy donor including, for example, from peripheral blood, an induced pluripotent stem cell (iPSC), or cord blood. In some embodiments, the NK cell may originate from a NK cell line. In some embodiments, the T cell may originate from a T cell line.

Without wishing to be bound by theory, introduction of FAP-CAR NK cells or FAP-CAR T cells into the tumor stroma is expected to disrupt the tumor microenvironment, resulting in attenuation of tumor growth and reduction in tumor-mediated immunosuppression due to increased cell activation, FAP-CAR NK cell-mediated killing or FAP-CAR T cell-mediated killing of FAP+ cancer-associated fibroblasts (CAFs), and/or increased cytokine production.

For example, the results of Example 2 show NK92 cells that stably express CD64 (FcγRI) and can bind to a compound that binds to FAP as described herein and can mediate ADCC (FIG. 13). Moreover, Example 2 further shows that NK92 cells that stably express CD64 bound to αFAP function as a "ready made CAR" and demonstrate selective anti-tumor activity (FIG. 15) and a combination therapy that uses αFAP and αTROP2 in combination with NK92 cells that stably express CD64 shows potent anti-tumor activity (FIG. 16).

In some embodiments, a compound that binds to FAP as described herein could be included in a combination therapy regimen. See, e.g., Brennen et al. 2012 Mol. Cancer Ther. 11, 257-266; Brunker et al. 2016 Mol. Cancer Ther. 15, 946-957; Gottschalk et al. 2013. PLoS One. 8, e82658; Fang et al. 2016 Mol. Ther. Oncolytics. 3, 16007; Chan et al. 2018 Oncogene. 37, 160-173. Exemplary combination therapies may include the compound and, for example, a chemotherapeutic drug or radioimmunotherapy, or both.

This disclosure further described a kit including a compound that binds to FAP as described herein. For example, a kit may include a composition that includes B12 IgG or a fragment thereof. The compound in the kit may be labeled with one or more detectable markers, as described herein.

A kit may include one or more containers filled with one or more of the monoclonal antibodies of the invention. Additionally, the kit may include other reagents such as buffers and solutions needed to practice the invention are also included. Optionally associated with such container(s) may be a notice or printed instructions. As used herein, the phrase "packaging material" refers to one or more physical structures used to house the contents of the kit. The packaging material is constructed by well-known methods, preferably to provide a sterile, contaminant-free environment. As used herein, the term "package" refers to a solid matrix or material such as glass, plastic, paper, foil, and the like, capable of holding within fixed limits a polypeptide.

Exemplary Composition Embodiments

1. A composition comprising a compound that binds to fibroblast activation protein alpha (FAP), wherein the compound comprises an amino acid sequence that is at least 75%, at least 80%, at least 85%, at least 90%, at least 95%, at least 96%, at least 97%, at least 98%, or at least 99% identical to an amino acid sequence of at least one of SEQ ID NO:3, SEQ ID NO:4, and SEQ ID NO:5; and an amino acid sequence that is at least 75%, at least 80%, at least 85%, at least 90%, at least 95%, at least 96%, at least 97%, at least 98%, or at least 99% identical to an amino acid sequence of at least one of SEQ ID NO:6, SEQ ID NO:7, and SEQ ID NO:8.

2. The composition of Embodiment 1, wherein the compound comprises an amino acid sequence that is at least 75% identical to the amino acid sequence of SEQ ID NO:3, an amino acid sequence that is at least 75% identical to the amino acid sequence of SEQ ID NO:4, an amino acid sequence that is at least 75% identical to the amino acid sequence of SEQ ID NO:5, an amino acid sequence that is at least 75% identical to the amino acid sequence of SEQ ID NO:6, an amino acid sequence that is at least 75% identical to the amino acid sequence of SEQ ID NO:7, and an amino acid sequence that is at least 75% identical to the amino acid sequence of SEQ ID NO:8.

3. The composition of any one of the preceding Embodiments, wherein the compound comprises an amino acid sequence at least 75%, at least 80%, at least 85%, at least 90%, at least 95%, at least 96%, at least 97%, at least 98%, or at least 99% identical to the amino acid sequence of SEQ ID NO:2; or an amino acid sequence at least 75%, at least 80%, at least 85%, at least 90%, at least 95%, at least 96%, at least 97%, at least 98%, or at least 99% identical to the amino acid sequence of SEQ ID NO:1, or
  both.
4. The composition of any one of the preceding Embodiments, wherein the compound comprises an antibody.
5. The composition of any one of the preceding Embodiments, wherein the compound comprises a monoclonal antibody.
6. The composition of any one of the preceding Embodiments, wherein the compound comprises B12IgG.
7. The composition of any one of Embodiments 1 to 6, wherein the compound binds to the same FAP epitope as B12 IgG.
8. The composition of any one of the preceding Embodiments, wherein the compound comprises a labeled compound.
9. The composition of any one of the preceding Embodiments, wherein the composition comprises a compound conjugated to a reporter molecule.
10. The composition of Embodiment 9, wherein the reporter molecule comprises one or more of an enzyme, a fluorescent dye, an infrared dye, a chemiluminescent reporter, or a hapten.
11. The composition of any one of the preceding Embodiments, wherein the composition comprises a cell-based immunotherapeutic.
12. The composition of Embodiment 11, wherein the cell-based immunotherapeutic comprises a chimeric antigen receptor (CAR) T cell and/or a CAR natural killer (NK) cell.
13. The composition of any one Embodiments 1 to 4, wherein the compound comprises a single-chain variable fragment (scFv).
14. The composition of any one of the preceding Embodiments, wherein the composition comprises a pharmaceutical composition.

Exemplary Methods of Using
1. A method of using the composition of any one of the preceding Embodiments.
2. The method of Embodiment 1, wherein the method comprises using the composition as a diagnostic agent.
3. The method of Embodiment 1, wherein the method comprises using the composition to image a cell expressing FAP.
4. The method of Embodiment 2 or 3, wherein the method comprises visualizing the margin of a tumor.
5. The method of any one of the preceding Embodiments, wherein the method comprises a FAP-positive tumor by positron emission tomography/computed tomography (PET/CT) imaging.
6. The method of Embodiment 1, wherein the method comprises using the composition as a therapeutic agent.
7. The method of Embodiment 6, wherein the method comprises using the composition in an antibody-targeted therapy.
8. The method of Embodiment 7, wherein the antibody-targeted therapy comprises radioimmunotherapy or a an antibody-drug conjugate.
9. The method of Embodiment 6, wherein the method comprises using the composition in a cell-based immunotherapeutic.
10. The method of any one of the preceding Embodiments, wherein the method comprises using the composition to identify a cancer-associated fibroblast (CAF).
11. The method of any one of the preceding Embodiments, wherein the method comprises detecting the compound, and wherein the composition comprises the compound conjugated to a reporter molecule.
12. The method of Embodiment 11, wherein the reporter molecule comprises one or more of an enzyme, a fluorescent dye, an infrared dye, a chemiluminescent reporter, or a hapten.
13. The method of any one of the Embodiments 1 to 12 for use in the treatment of a tumor.
14. The method of any one of the Embodiments 1 to 12 for use in the diagnosis of a tumor.

Exemplary Antibody Embodiments
1. A monoclonal antibody comprising
  an amino acid sequence that is at least 75%, at least 80%, at least 85%, at least 90%, at least 95%, at least 96%, at least 97%, at least 98%, or at least 99% identical to an amino acid sequence of at least one of SEQ ID NO:3, SEQ ID NO:4, and SEQ ID NO:5; and
  an amino acid sequence that is at least 75%, at least 80%, at least 85%, at least 90%, at least 95%, at least 96%, at least 97%, at least 98%, or at least 99% identical to an amino acid sequence of at least one of SEQ ID NO:6, SEQ ID NO:7, and SEQ ID NO:8.
2. The monoclonal antibody of Embodiment 1, wherein the monoclonal antibody comprises
  an amino acid sequence that is at least 75% identical to the amino acid sequence of SEQ ID NO:3, an amino acid sequence that is at least 75% identical to the amino acid sequence of SEQ ID NO:4, an amino acid sequence that is at least 75% identical to the amino acid sequence of SEQ ID NO:5, an amino acid sequence that is at least 75% identical to the amino acid sequence of SEQ ID NO:6, an amino acid sequence that is at least 75% identical to the amino acid sequence of SEQ ID NO:7, and an amino acid sequence that is at least 75% identical to the amino acid sequence of SEQ ID NO:8.
3. The monoclonal antibody of any one of the preceding Embodiments, wherein the monoclonal antibody comprises
  an amino acid sequence at least 75%, at least 80%, at least 85%, at least 90%, at least 95%, at least 96%, at least 97%, at least 98%, or at least 99% identical to the amino acid sequence of SEQ ID NO:2; or
  an amino acid sequence at least 75%, at least 80%, at least 85%, at least 90%, at least 95%, at least 96%, at least 97%, at least 98%, or at least 99% identical to the amino acid sequence of SEQ ID NO:1, or
  both.
4. A monoclonal antibody comprising
  an amino acid sequence comprising a light chain variable region, wherein the light chain variable region CDR1 sequence comprises SEQ ID NO:3, the light chain variable region CDR2 sequence comprises SEQ ID NO:4, and the light chain variable region CDR3 sequence comprises SEQ ID NO:5; or
  an amino acid sequence comprising a heavy chain variable region, wherein the heavy chain variable region CDR1 sequence comprises SEQ ID NO:6, wherein the heavy chain variable region CDR2 sequence comprises SEQ ID NO:7, and wherein the heavy chain variable region CDR3 sequence comprises SEQ ID NO:8; or
  both.
5. The monoclonal antibody of Embodiment 4, wherein the monoclonal antibody comprises
  a light chain variable region comprising the amino acid sequence of SEQ ID NO: 1; or a heavy chain variable region comprising the amino acid sequence of SEQ ID NO:2; or
both.
6. The monoclonal antibody of any one of the preceding Embodiments, wherein the monoclonal antibody comprises B12 IgG.
7. The monoclonal antibody of any one of Embodiments 1 to 3, wherein the monoclonal antibody binds to the same FAP epitope as B12 IgG.

The present invention is illustrated by the following examples. It is to be understood that the particular examples, materials, amounts, and procedures are to be interpreted broadly in accordance with the scope and spirit of the invention as set forth herein.

EXAMPLES

Example 1

Figure 8A:
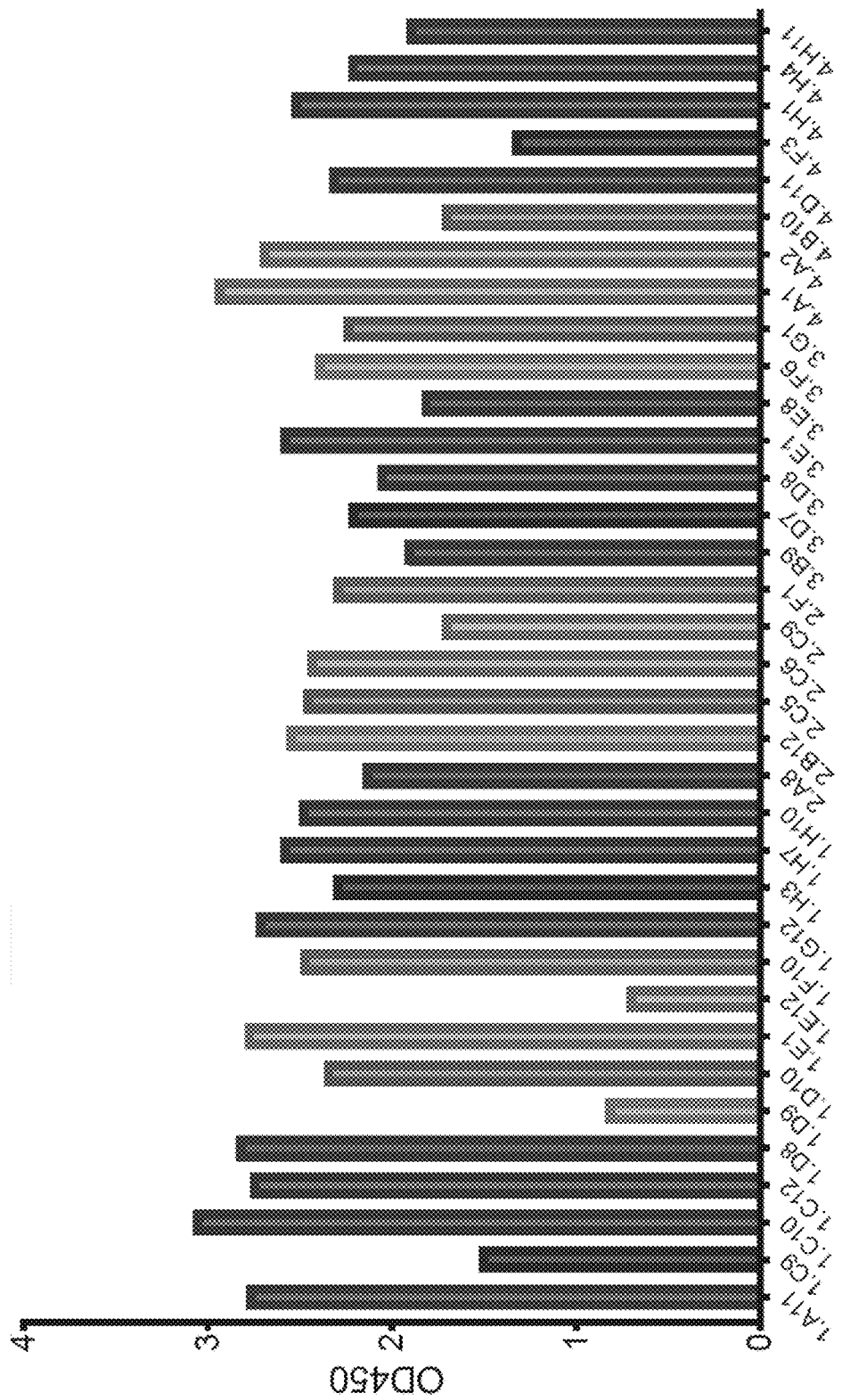
FIG. 8A-FIG. 8D shows in vitro characterization of single-chain variable (scFv) antibody fragments leading to the selection of B12 scFv.
Figure 8B:
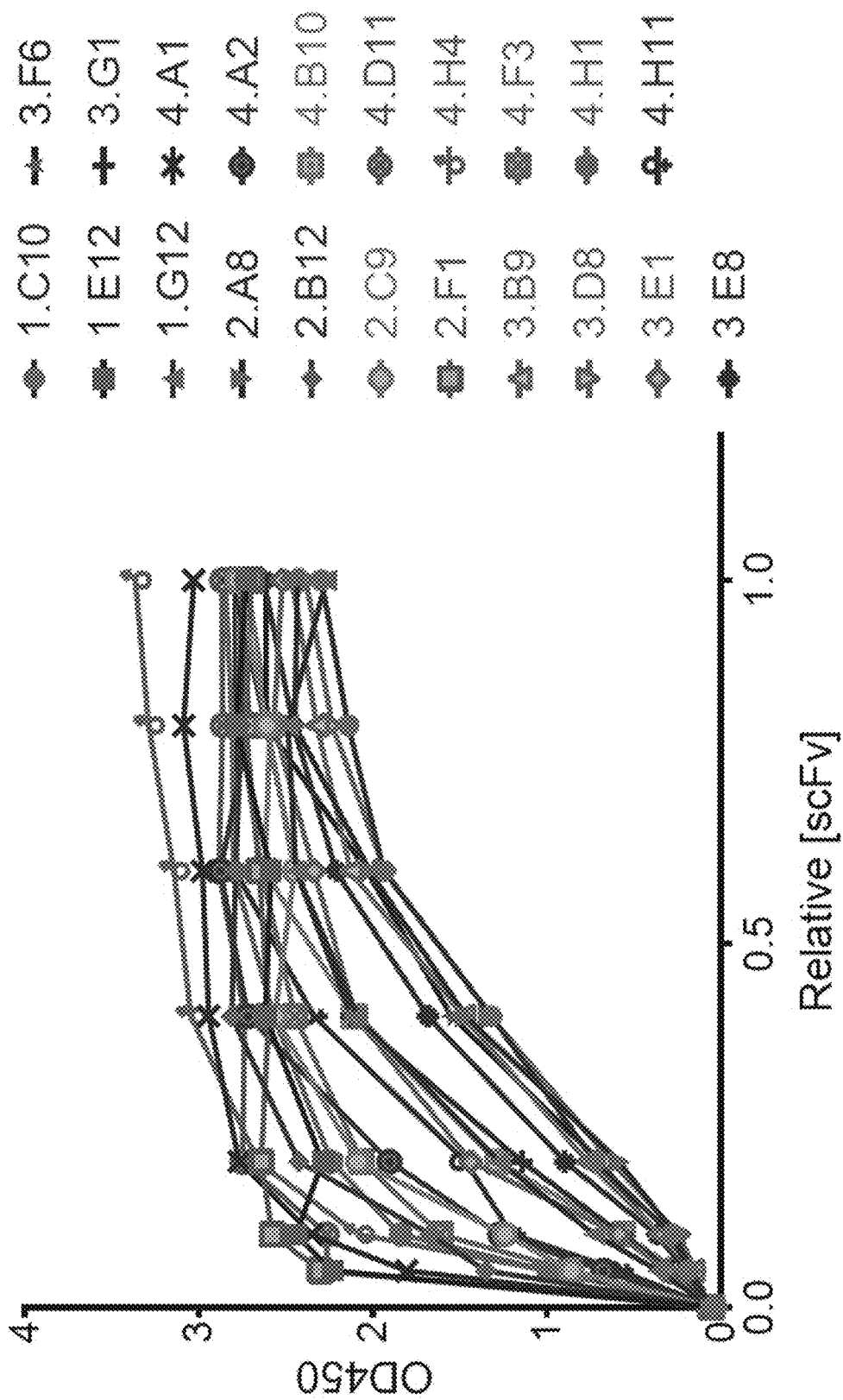
Figure 8C:
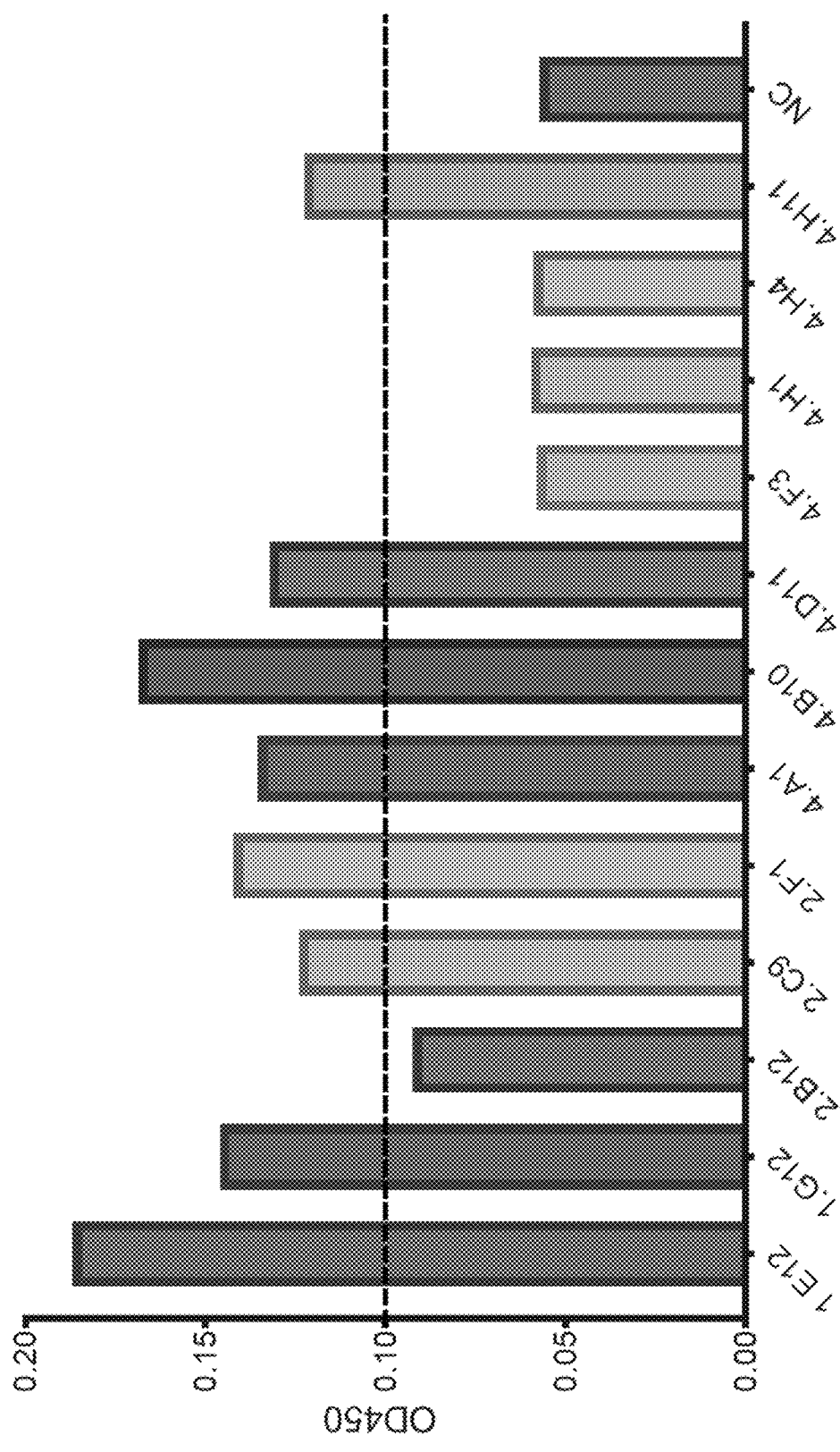

This Example describes the development and initial characterization of the anti-FAP monoclonal antibody B12 IgG.
Results
Selection and Characterization of Anti-FAP scFv Antibody Fragments A naïve murine scFv antibody phage display library with a diversity of $1.9 \times 10^9$ was used to identify antibodies specific for human FAP (hFAP; FIG. 8). Biopanning was performed using biotinylated hFAP attached to streptavidin coated magnetic beads to conserve native protein structure. After four rounds of biopanning, 384 clones were screened against biotinylated hFAP by enzyme-linked immunosorbent assay (ELISA). Of these clones, 35 demonstrated high ELISA signal (FIG. 8A), 21 clones were found to bind hFAP in a concentration-dependent manner (FIG. 8B), and twelve clones had unique sequences. The twelve unique clones were screened against biotinylated human dipeptidyl peptidase IV (hDPP-IV), a serine protease which shares 52% homology with hFAP. Of these clones, four showed no cross-reactivity with hDPP-IV (FIG. 8C). The FAP-specific clones were then expressed and purified for further testing.

Figure 1B:
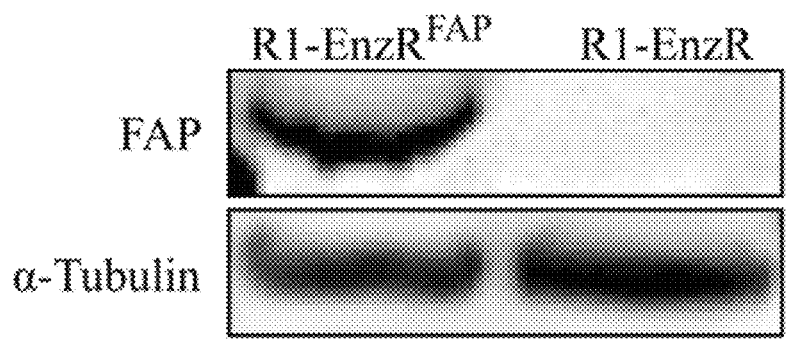
Figure 1C:
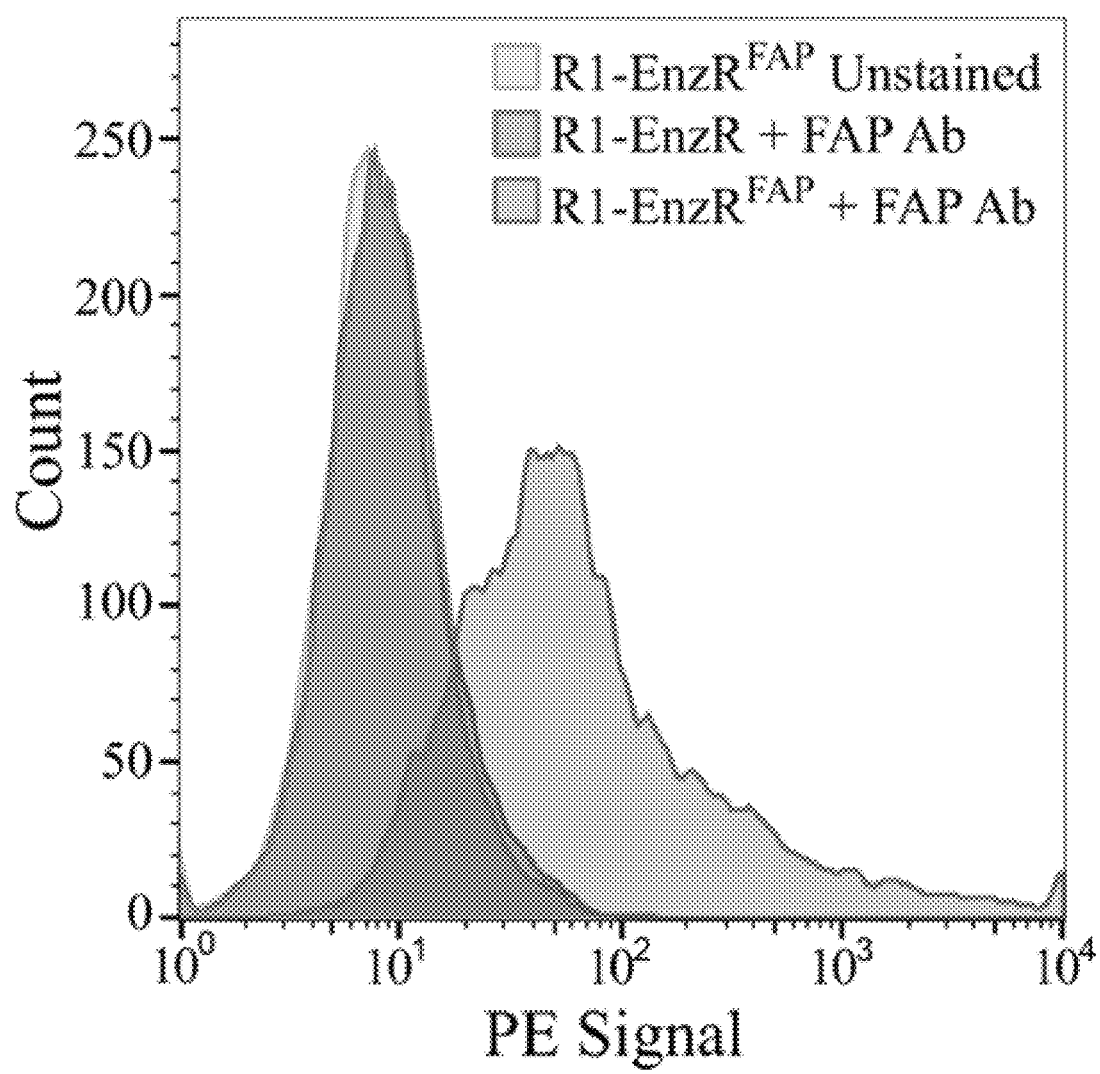

Since no in vitro cell line model for CAFs existed, a hFAP-expressing cell line was engineered to use for antibody characterization and validation (FIG. 1). The human prostate cancer cell line CWR-R1-Enzalutamide Resistant/luciferase$^+$ was lentiviral transduced to express hFAP (R1-EnzR$^{FAP}$). Expression of hFAP in the engineered cell line was confirmed by quantitative RT-PCR (FIG. 1A) and Western blot (FIG. 1B). Flow cytometry with a commercial antibody was used to confirm membrane expression of hFAP (FIG. 1C). No hFAP mRNA, protein, or membrane expression was observed in the parental R1-EnzR cells (FIG. 1).

Figure 2A:
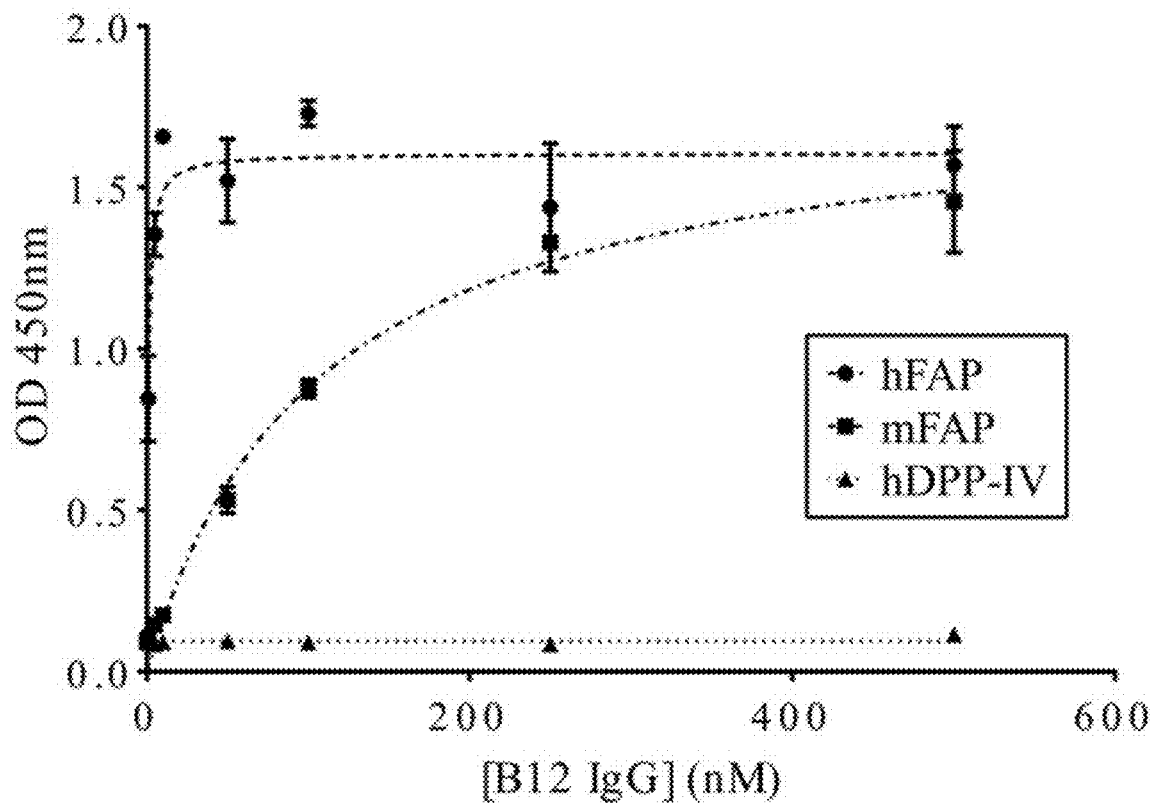
Figure 2B:
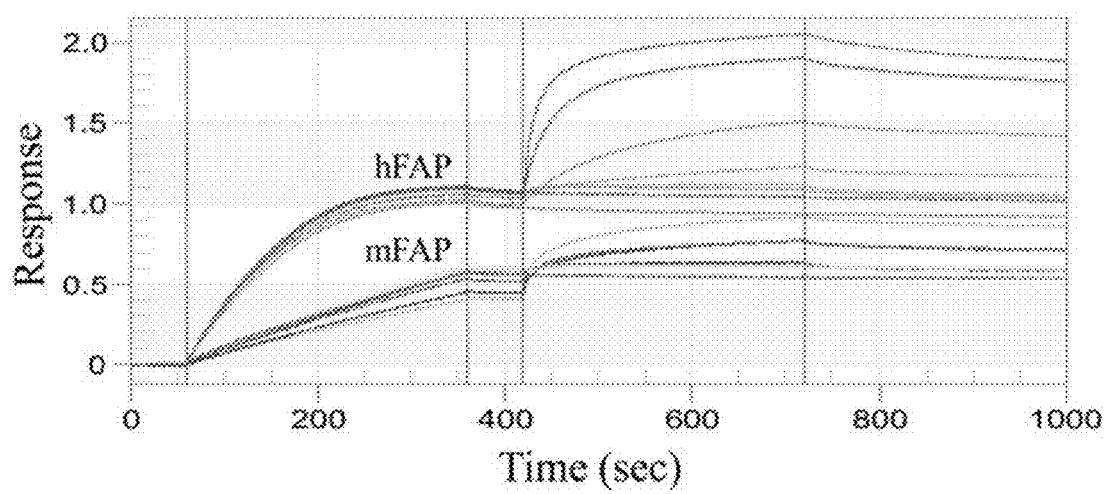
Figure 2C:
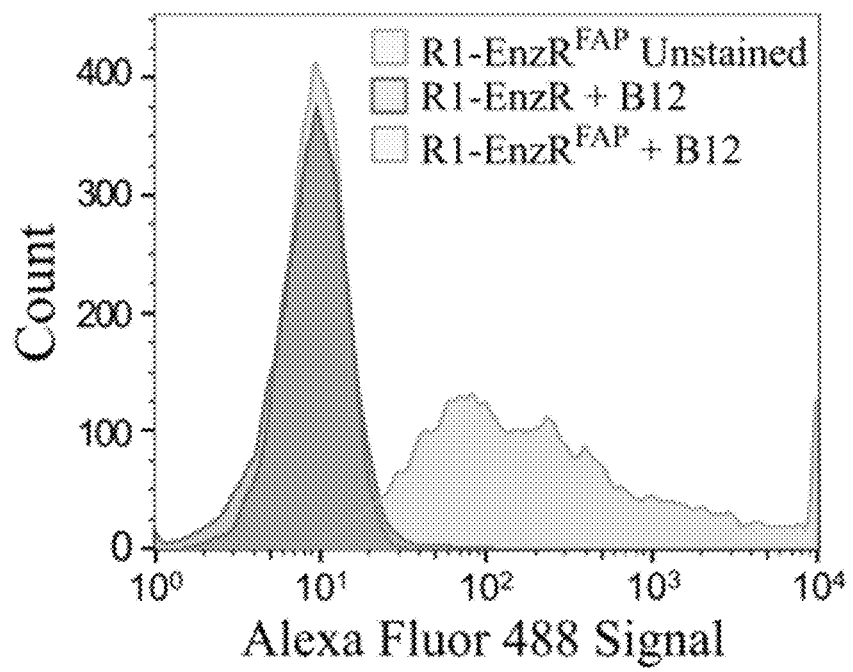
Figure 2D:
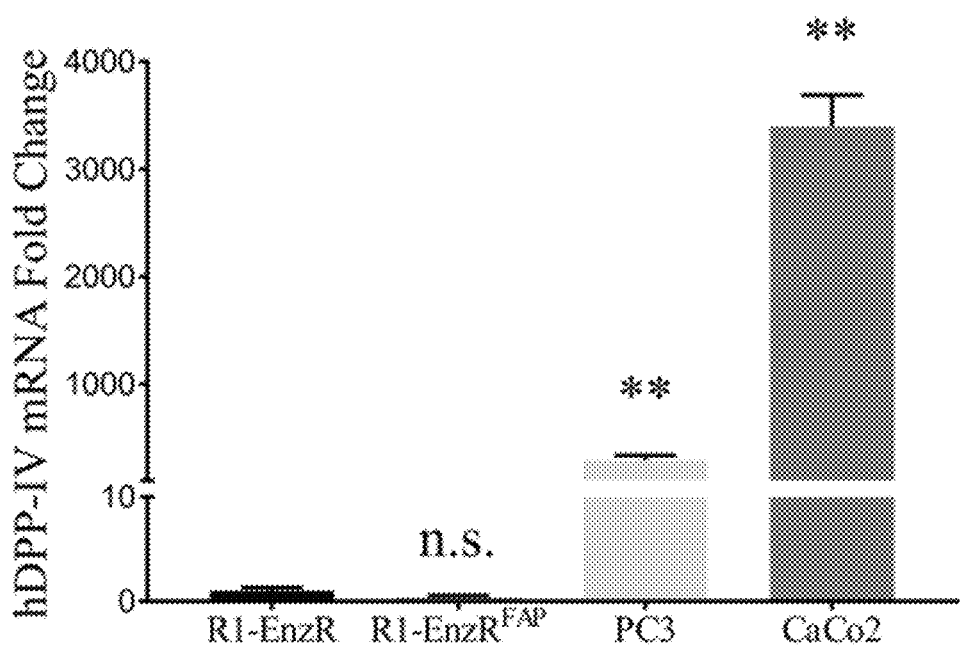
Figure 3A:
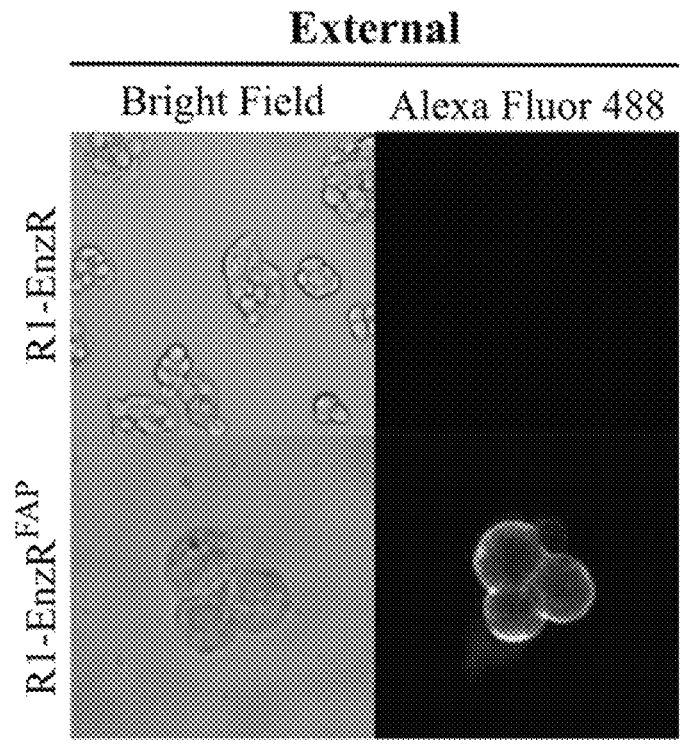
FIG. 3A-FIG. 3B show confocal microscopy analysis indicating B12 IgG can be used for external staining and can be imaged after being internalized.
Figure 3B:
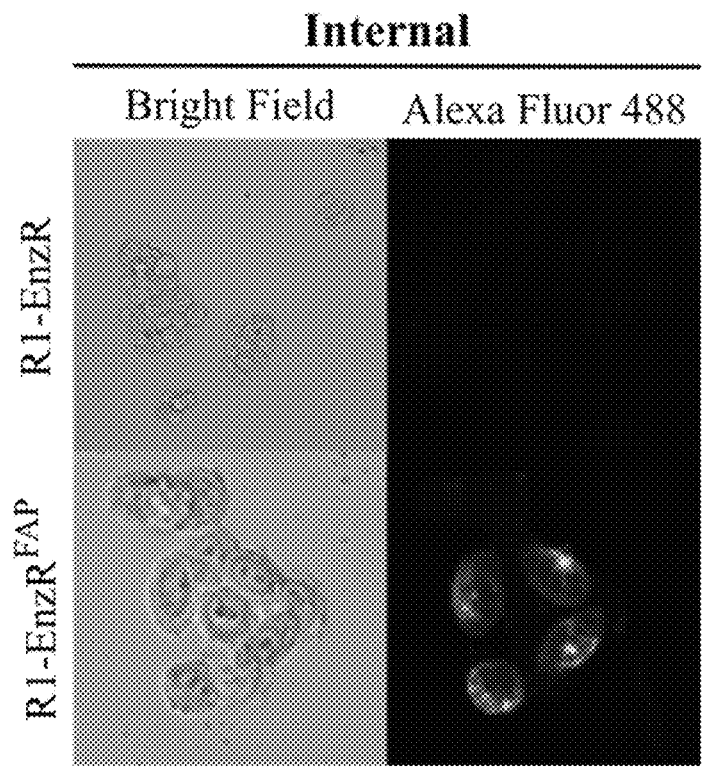
Figure 4A:
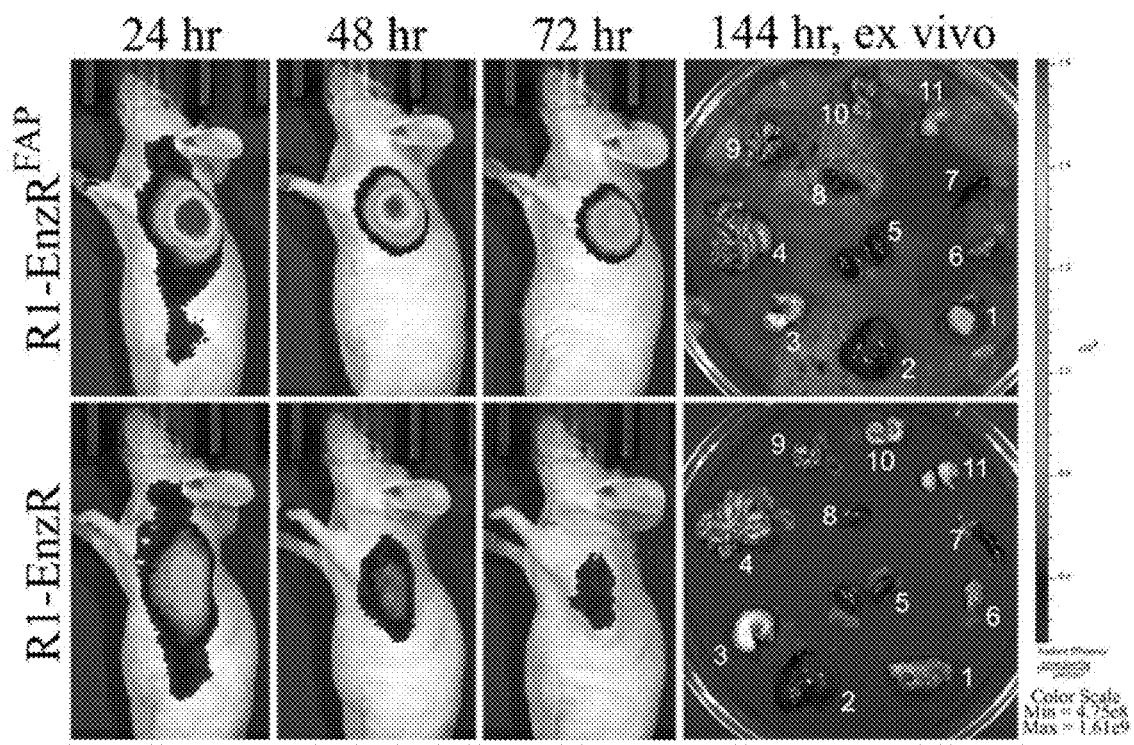
FIG. 4A-FIG. 4B shows validation of B12 IgG selectivity in a subcutaneous, localized model.
Figure 4B:
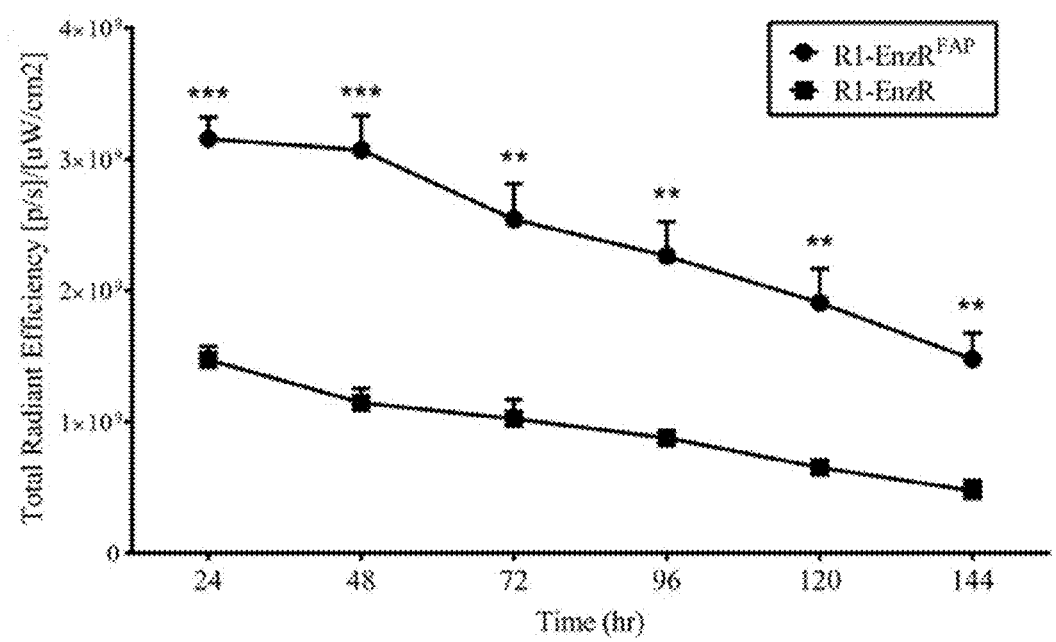
Figure 8D:
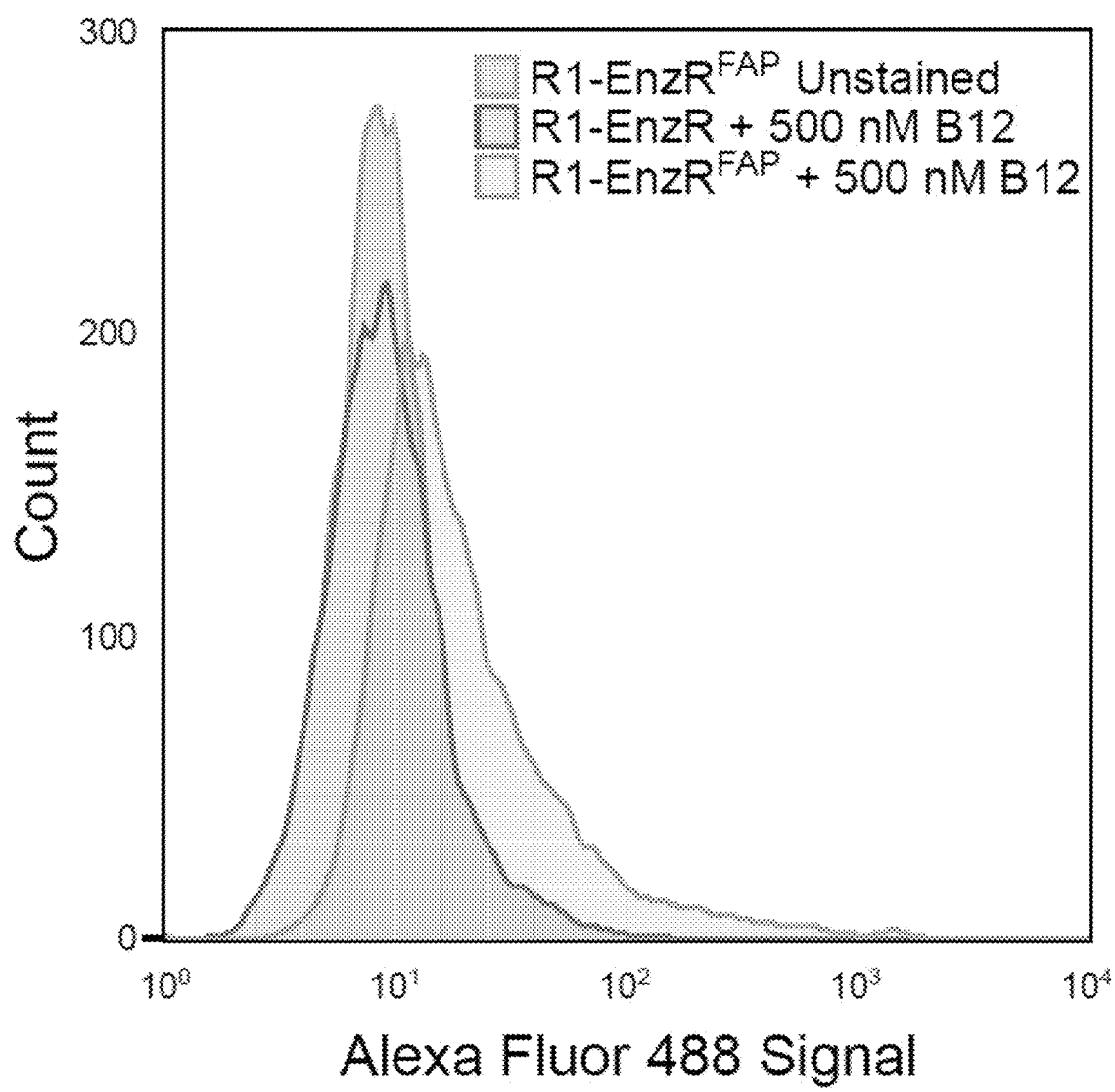

The four expressed scFv clones were next investigated for the ability to selectively bind hFAP-expressing cells. The scFv clones were conjugated to Alexa Fluor 488 and tested in parallel by flow cytometry. It was determined that only the scFv produced by clone B12 bound to the transduced R1-EnzR$^{FAP}$ but not to the parental R1-EnzR cells (FIG. 8D). Based on the cumulative data, clone B12 was selected as the lead scFv for development as a chimeric anti-FAP IgG antibody.
Generation and In Vitro Characterization of Anti-FAP IgG Antibody The heavy and light chains of the B12 scFv were cloned into full-length human immunoglobulin (IgG) vectors for expression in HEK293T cells. After purification, the selectivity and affinity of B12 IgG were determined in vitro (FIG. 2). By ELISA, B12 IgG was found to cross-react with both hFAP and murine FAP (mFAP)—An important characteristic for validating B12 IgG in endogenous FAP-expressing murine models (FIG. 2A). The concentration-dependent saturation of the ELISA suggests that B12 IgG bound to a single epitope on both hFAP and mFAP. In addition, no binding was observed with the homologous prolyl protease hDPP-IV (FIG. 2A). Surface plasmon resonance was next used to determine the bivalent affinity of B12 IgG for recombinant FAP protein. The $K_D$ of B12 IgG for hFAP and mFAP were calculated to be roughly similar, with values of 3.39 nM and 1.86 nM, respectively (FIG. 2B). Having characterized the ability of B12 IgG to bind to recombinant proteins, it was next investigated if B12 IgG could bind to native protein expressed on the surface of cancer cells using flow cytometry. As documented by the profound right shift, Alexa Fluor 488 labeled B12 IgG tightly bound to the transduced R1-EnzR$^{FAP}$ cells but did not bind to the parental FAP negative R1-EnzR cells (FIG. 2C). B12 IgG was also tested for cross-reactivity against hDPP-IV-expressing cells to confirm FAP selectivity by flow cytometry. Using quantitative RT-PCR, it was discovered that the transduced and parental R1-EnzR cells did not express hDPP-IV. Expression of hDPP-IV was observed in the prostate cancer cell line PC3, although expression was significantly higher in the colon cancer cell line CaCo2 (FIG. 2D). For flow cytometry, PC3 and CaCo2 were incubated with Alexa Fluor 488 labeled B12 IgG at a concentration of 100 nM. When evaluated, no binding was observed with the hDPP-IV-positive cells lines (FIG. 2E). Finally, B12 IgG internalization by FAP-expressing cells was assessed using confocal microscopy (FIG. 3). In addition to the ability of B12 IgG to stain the surface of fixed R1-EnzR$^{FAP}$ cells (FIG. 3A), B12 IgG was found to be internalized by R1-EnzR$^{FAP}$ cells when incubated at 37° C. for 60 minutes (FIG. 3B). No external staining or internalization occurred in the parental FAP negative R1-EnzR cells when incubated with B12 IgG under identical conditions (FIG. 3).
Anti-FAP IgG Antibody In Vivo Fluorescent Imaging The internalization and accumulation of B12 IgG in FAP-expressing cancer cells suggests potential utility for the antibody as an imaging probe. The ability of B12 IgG to detect FAP in localized in vivo models of prostate cancer using near-infrared (NIR) optical imaging was investigated (FIG. 4). For NIR optical imaging, B12 IgG was labeled with IRDye-800CW and injected into R1-EnzR$^{FAP}$ and parental R1-EnzR xenograft mice (FIG. 4A). High tumor uptake and retention of the NIR probe was observed as early as 24 hours post-injection in the R1-EnzR$^{FAP}$ xenograft mice. Lower tumor uptake was observed in the R1-EnzR xenograft, indicating that B12 IgG does detect mFAP expressed by murine origin stromal cells within the tumor xenograft. Graphing the fluorescence efficiency of the regions of interest for each of the mice imaged as a function of time highlighted the uptake kinetics of the probe (FIG. 4B). At the 144 hour endpoint, tumors and secondary organs were excised from the mice and imaged to detect fluorescence from the probe. In the R1-EnzR$^{FAP}$ and R1-EnzR mice, fluorescence was observed in the tumor tissue suggesting that the accumulation and retention of the probe there were greater than any other organ, including the liver, the main clearance organ for IgG antibodies (FIG. 4A).

Figure 5A:
FIG. 5A-FIG. 5B show a pilot study of B12 IgG selectivity in a metastatic model.
Figure 5B:
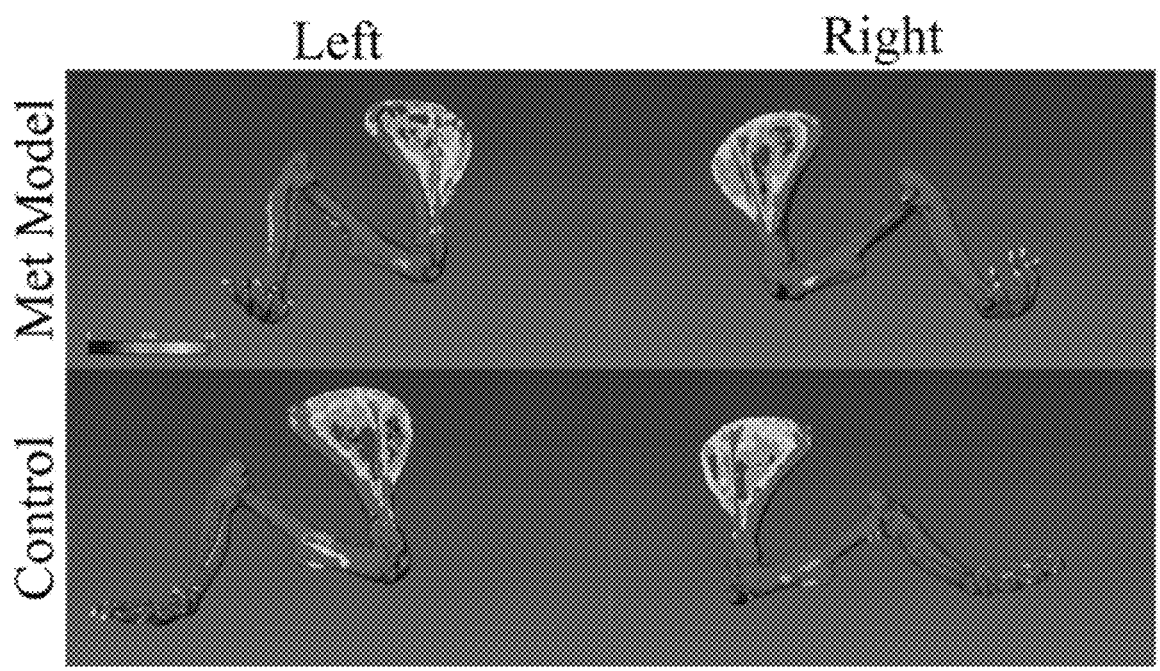
Figure 6A:
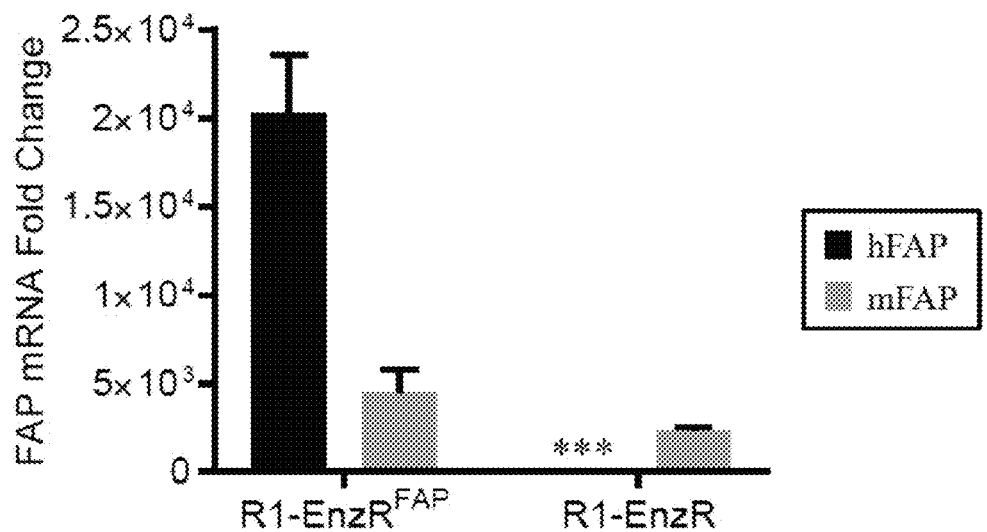
FIG. 6A-FIG. 6F show FAP expression and B12 IgG penetration ex vivo in R1-EnzR$^{FAP}$ and R1-EnzR xenograft tissues.
Figure 6B:
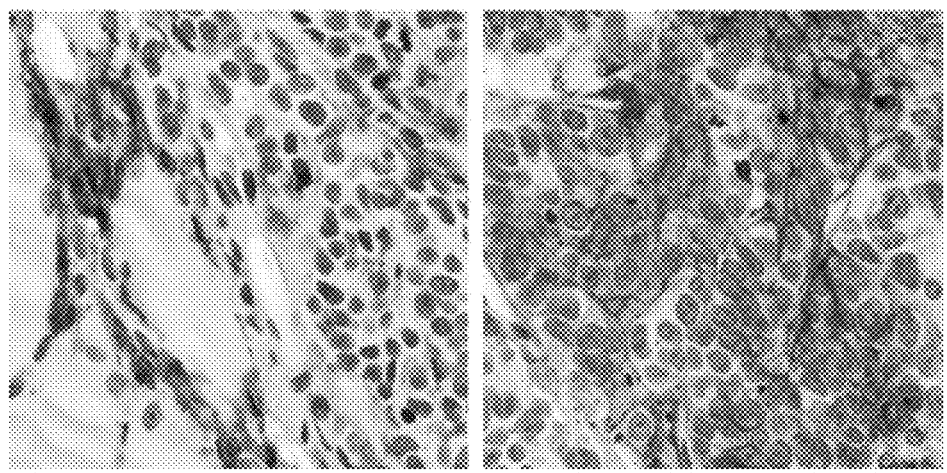
Figure 6C:
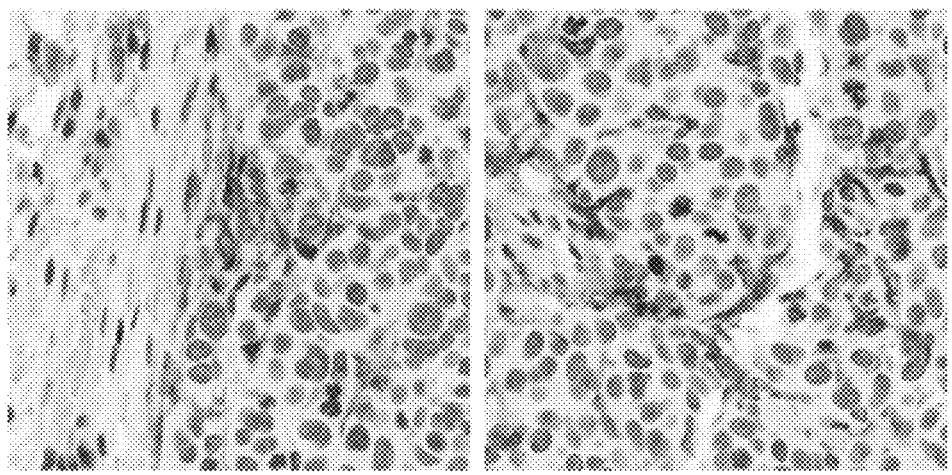
Figure 6D:
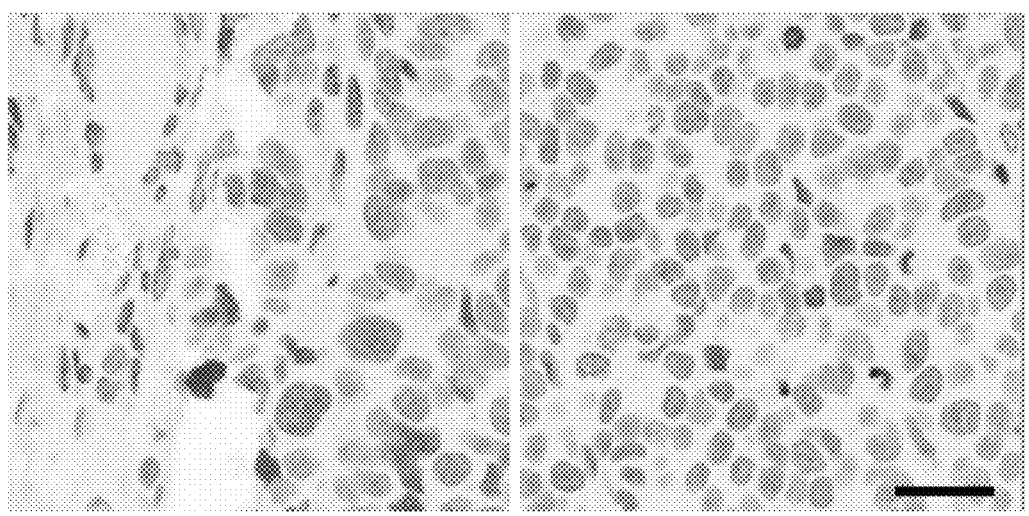
Figure 6E:
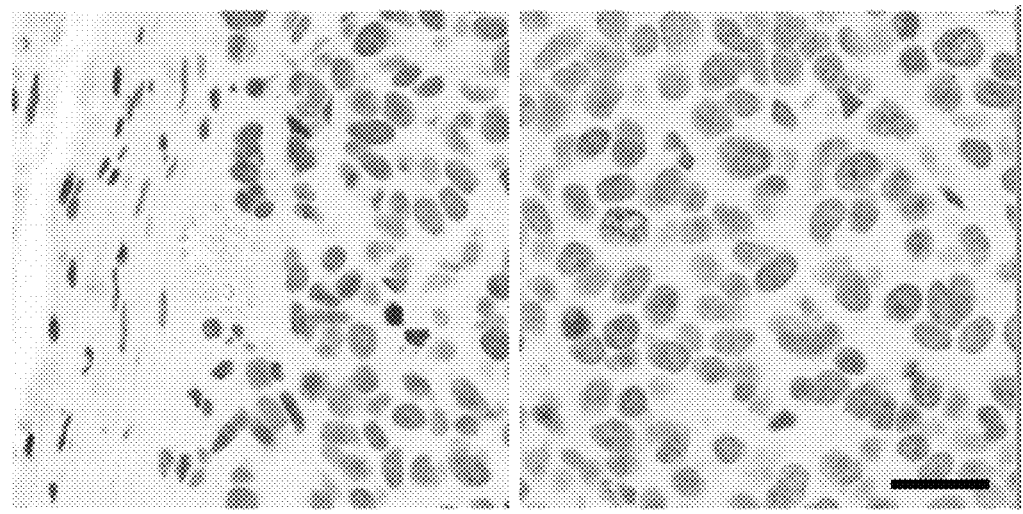
Figure 6F:
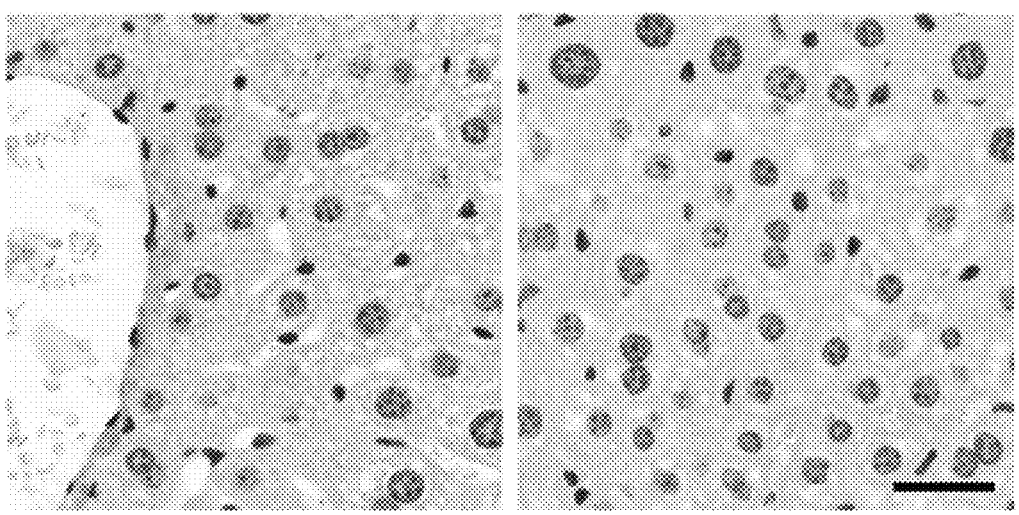
Figure 9:
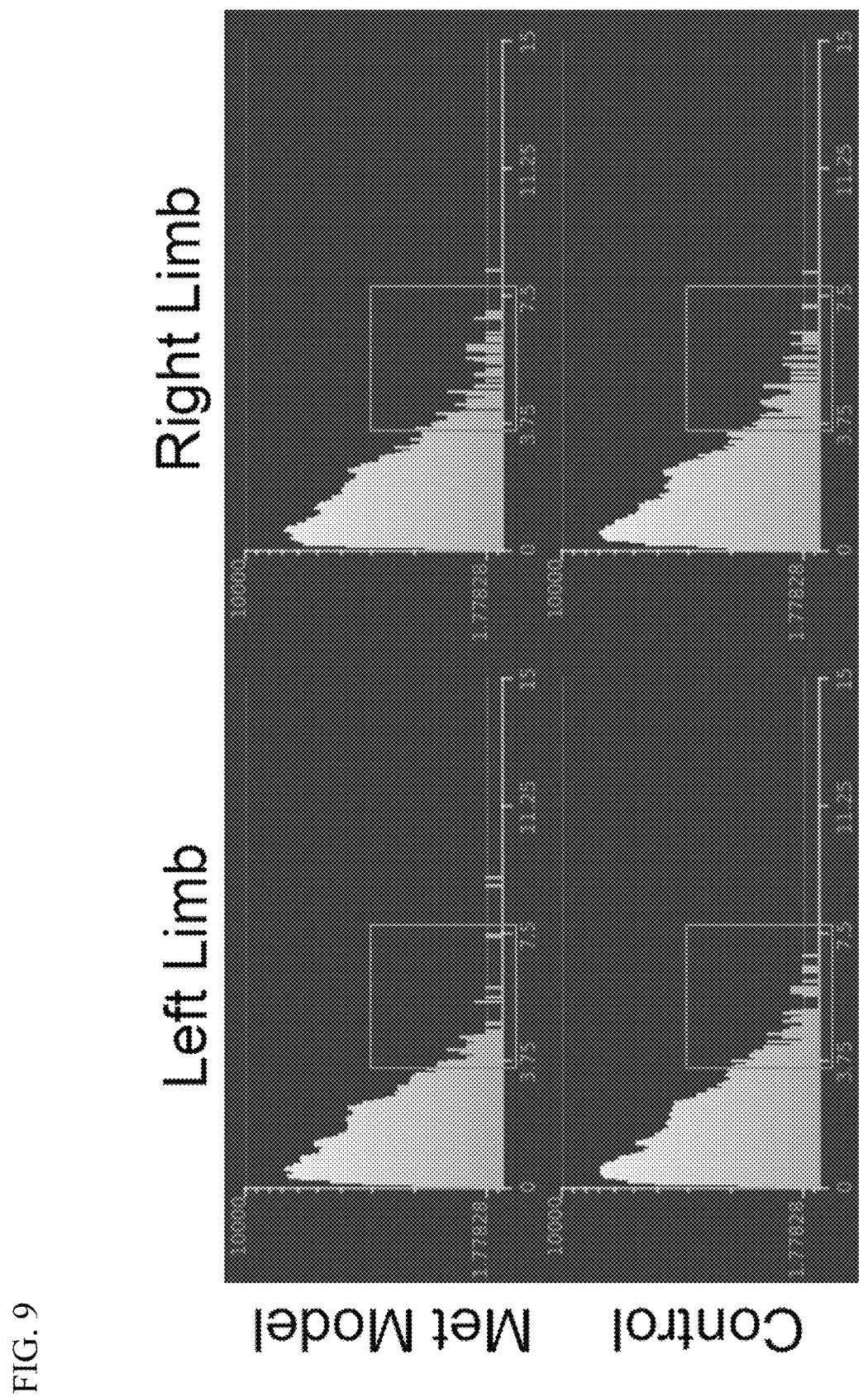
FIG. 9 shows representative surface thickness histograms of front limbs of mice. Micro computed tomography (μCT) was used to image an R1-EnzR$^{FAP}$ metastatic xenograft mouse (tumor) and a control mouse without metastases (control) 72 hours post-injection, as described in Example 1. Data was reconstructed and analyzed using AMIRA software. A reconstructed triangular surface model of the limbs was generated using AMIRA software to calculate surface thickness and identify topological anomalies. Data is represented as histograms of surface thickness (mm). Bone surface thickness (in mm) was calculated in the front limbs (left and right) of each animal. Decreased thickness was measured in the left limb of the metastatic model (red box) suggesting osteolytic events and presence of an osseous metastatic lesion.

B12 IgG was next tested for the ability to detect FAP in advanced in vivo models of prostate cancer using NIR optical imaging. IRDye-800CW labeled B12 IgG was used in a pilot study with metastatic R1-EnzR$^{FAP}$ xenograft mice (FIG. 5). Probe localization was achieved at 24 hours with the R1-EnzR$^{FAP}$ xenograft demonstrating metastatic lesion uptake and retention (FIG. 5A). At the 72 hour endpoint, mice were imaged using micro-computed tomography to calculate bone surface thickness. Decreased thickness in the left limb was observed, suggesting osteolytic events consistent with R1-EnzR bone metastases (FIG. 5B). The left limb was compared to its own right limb and a control murine without metastases. Surface thickness histograms used to quantify the data show that the composition of the left limb is thinner compared to the control limbs (FIG. 9).

To validate the model, FAP expression and B12 IgG penetration ex vivo in R1-EnzR$^{FAP}$ and R1-EnzR xenograft tissues was investigated (FIG. 6). The excised tumor tissues and secondary organs from the subcutaneous xenograft imaging study were immediately fixed in 10% formalin or frozen in buffer for storage at −80° C. FAP mRNA levels were analyzed from frozen transduced and parental cell xenografts using human and murine specific gene expression assay probes. Human FAP mRNA was only detected in the R1-EnzR$^{FAP}$ xenograft while mFAP was detected in both xenograft models because of its expression in the reactive stroma of the tumor xenograft (FIG. 6A). Having documented the expression of FAP at the mRNA level, whether the expression of FAP could be detected by IHC was investigated. For IHC, a secondary anti-human IgG monoclonal antibody was used to detect B12 IgG penetration in the tumor tissue. Strong staining on the tumor edge and in the internal tumor tissue was seen in the positive control R1-EnzR$^{FAP}$ sections (FIG. 6B). In the R1-EnzR xenograft sections, staining was only observed along the stroma-tumor interface and localized to capillaries within the tumor tissue (FIG. 6C). This staining pattern suggests that B12 IgG is localized to mFAP-expressing murine stromal cells. Staining was absent in murine liver tissue which served as a negative control (FIG. 6D).

Experimental Procedures

Cell Culture and R1-EnzR$^{FAP}$P Cell Line Generation

All cancer cell lines used in this study were purchased from American Type Culture Collection (ATCC) and were maintained in their respective recommended media, supplemented with 10% FBS (Gibco, ThermoFisher Scientific, Waltham, Mass.), 1% antibiotic-antimycotic (Gibco), and 1% glutaMAX (Gibco) at 37° C. and 5% CO$_2$. Additionally, enzalutamide resistant (EnzR) cell lines were supplemented with 10 μM enzalutamide (APExBIO) continuously. The cell lines were authenticated using short-tandem repeat profiling provided by the vendor and routinely monitored for *mycoplasma* contamination. The FAP-expressing CWR-R1-EnzR$^{FAP}$/luciferase$^+$ cell line (R1-EnzR$^{FAP}$) was generated using PROM1 Lentifect Purified Lentiviral Particles (LPP-Z7538-Lv242-100, GeneCopoeia, Inc., Rockville, Md.). CWR-R1-EnzR/luciferase$^+$ cells were seeded at 5×10$^4$ cells/well in a 24-well plate using heat-inactivated FBS. Once cells were 70-80% confluent, transduction was performed according to the manufacturer's protocol using 7 g/mL Polybrene (H9268-5G, Sigma-Aldrich, St. Louis, Mo.) and 10 μL of lentivirus for 24 hours. Following overnight incubation, transduced cells were reseeded into three wells of a six-well plate and incubated for 48 hours. Transduced clones were stably selected with 3 μg/mL puromycin continuously.

Western Blot

Cell lysates were prepared using 1× laemmli buffer. The concentrations of cell lysates were determined using an RCDC assay. 10 μg of total protein per sample was denatured with 5% 3-mercaptoethanol and separated on a 4% to 12% Bis-Tris Plus precast gel (NW04122, Invitrogen, Carlsbad, Calif.) with sodium dodecyl sulfate polyacrylamide gel electrophoresis and then transferred at 20 V onto a nitrocellulose transfer membrane (ThermoFisher Scientific, Waltham, Mass.) with an iBlot 2 Dry Blotting System (ThermoFisher Scientific, Waltham, Mass.) for 7 minutes. Membranes were blocked in 5% BSA in TBS, 1% Tween20 and probed with murine anti-FAP monoclonal antibody (1:1000, sc-100528, Santa Cruz Biotechnology, Dallas, Tex.) overnight at 4° C., washed, and then incubated in rabbit anti-murine monoclonal antibody conjugated to peroxidase (1:1000, sc-516102, Santa Cruz Biotechnology, Dallas, Tex.) for 1 hour at room temperature. Equal protein loading was confirmed using murine anti-α-tubulin (1:10000, sc-23948, Santa Cruz Biotechnology, Dallas, Tex.) and anti-murine conjugated to peroxidase (1:10,000). Binding was detected using the SuperSignal West Pico PLUS Chemiluminescent Substrate (ThermoFisher Scientific, Waltham, Mass.) and blots were imaged with a MyECL imager (ThermoFisher Scientific, Waltham, Mass.) and Image Studio 2.0 software (Li-Cor Biosciences, Lincoln, Nebr.).

Phage Display Biopanning

An in-house murine naïve single chain variable fragment (scFv) antibody phage display library was used to identify clones against recombinant human FAP. Recombinant human FAP (3715-SE-010, R&D Systems, Minneapolis, Minn.) was biotinylated using EZ-link NHS-PEG4-Biotin (ThermoFisher Scientific, Waltham, Mass.) according to manufacturer's instructions. The biotinylated recombinant human FAP was captured using Dynabeads M-270 Streptavidin (Invitrogen, Carlsbad, Calif.) in 100 ng/μL of 1% BSA in DPBS without Ca and Mg (Quality Biological, Gaithersburg, Md.). The biopanning protocol was carried out as previously described in Kim et al. 2011 Methods. 55, 303-309. The biopanning protocol was repeated four times to enrich for positive binders to recombinant human FAP.

Quantitative RT-PCR

RNA was prepared from each cell line (~2×10$^6$ cells) using an RNeasy kit (Qiagen, Hilden, Germany). RNA was synthesized to cDNA using the High Capacity RNA-to-cDNA kit (Applied Biosystems, Foster City, Calif.). For each gene, Taqman qRT-PCR was performed using the Taqman Universal PCR Master Mix (Applied Biosystems, Foster City, Calif.) and the following Taqman Gene Expression Assay Probes: human FAP Hs00990807_m1, murine FAP Mm01329177_m1, human DPP-IV Hs00897386_m1, 18s ribosomal 1 Hs03928985_g1, murine GAPDH Mm99999915_g1. 18s ribosomal 1 was used as a normalization control for the experimental human probes and GAPDH was used for the experimental murine probes. All qPCR was performed on a StepOnePlus Real-Time PCR system instrument (Applied Biosystems, Foster City, Calif.). Each sample had three technical replicates and each reaction was performed in three biological replicates. The data was analyzed using the comparative Ct method (fold change= $2^{-\Delta\Delta Ct}$) as previously described by Schmittgen et al. 2008 Nat. Protoc. 3, 1101-1108. All data are presented as mean±standard error of the mean (SEM)

ELISA

Positive scFv clone selection: ScFvs were produced from 384 individual clones using 5 mM IPTG induction in a microtiter plate format. The scFvs that leaked into the cell culture media were screened for binding to FAP by ELISA. MaxiSorp plates (Nunc Cell Culture, ThermoFisher Scientific, Waltham, Mass.) were coated with 50 μL of streptavidin (5 g/mL in PBS, Promega, Madison, Wis.) overnight at 4° C. Wells were washed two times with PBS and blocked with 370 μL of 2% BSA in PBS for 1 hour at room temperature. The wells were washed three times with PBS, 0.005% Tween20. 50 µL of biotinylated FAP (1 µg/mL in PBS, 1% BSA, 0.005% Tween20) was added to each well. Plates were shaken at room temperature for 1 hour. The wells were washed three times with PBS, 0.005% Tween20 and the supernatants of scFv induced cultures were added to each well and shaken at room temperature for 1 hour. The wells were washed three times with PBS, 0.005% Tween20. ScFv binding was detected with a 1:1000 dilution of anti-HA-tag monoclonal antibody conjugated to peroxidase (12-013-819-001, Sigma-Aldrich, St. Louis, Mo.) in PBS, 1% BSA and 50 µL Turbo™ B reagent (Pierce Protein Biology, ThermoFisher Scientific, Waltham, Mass.). Reactions were stopped with 10 µL of 2.5 M $H_2SO_4$ and the absorbance was measured at 450 nm using a microplate reader. Confirmed positive clones for FAP were sequenced to identify unique clones.

Dilution ELISA: A MaxiSorp plate was coated and blocked as described above. 50 µL of biotinylated human FAP, murine FAP, or human DPP-IV (1 g/mL in PBS, 1% BSA, 0.005% Tween20) was added to 8 sets of triplicate wells each. B12 IgG was serial-diluted from 500 nM to 0.1 nM in PBS, 1% BSA, 0.005% Tween20 and added to each well. Triplicate wells with biotinylated protein but no B12 IgG were used as a negative control. B12 IgG binding was detected with a 1:1000 dilution of anti-human IgG monoclonal antibody conjugated to peroxidase (sc-2769, Santa Cruz Biotechnology, Dallas, Tex.) in PBS, 1% BSA.

ScFv Expression and Purification

Unique clones were inserted into pET-22b(+) vectors (Novagen, Merck Millipore, Burlington, Mass.) according to the manufacturer's protocol. Expression of each clone was carried out in SHuffle T7 Competent *Escherichia coli* K12 cells (New England Biolabs, Ipswich, Mass.). A transformant of each scFv was selected and cultured overnight at 37° C. in 100 mL of 2×YT broth containing 100 µg/mL ampicillin, 2% glucose. The 100 mL overnight cultures were used to inoculate 4 L culture of 2×YT broth containing 100 µg/mL ampicillin, 0.1% glucose. Cells were cultured at 30° C. until the OD600 reached 0.6. Protein expression was induced by the addition of 1 mM IPTG and 0.4 M sucrose and cultured for an additional 17 hours at 25° C. Cells were harvested by centrifugation at 6000 g for 10 minutes and the periplasmic *E. coli* fraction was extracted via osmotic shock. Harvested cell pellets from each 4 L culture were resuspended in 20 mL of 1×TES (0.2 M Tris, pH 8, 0.5 mM EDTA, 0.5 M sucrose) and 20 mL of 1×EDTA-free protease inhibitor (Pierce) solution. Each cell suspension was incubated for 30 minutes on ice with agitation every 10 minutes. Cells were centrifuged and the supernatant was collected as periplasmic fraction 1. This protocol was repeated to the cell pellet to obtain periplasmic fraction 2. The two periplasmic prep fractions were combined and 1 M $MgCl_2$ (200 µL) and 5 M imidazole (600 µL) were added prior to purification. The periplasmic fractions were filtered through a 0.45 µm filter and purified by $Ni^{2+}$ affinity chromatography as follows. A 5 mL HisTrap HP column (GE Healthcare, Chicago, Ill.) was equilibrated with 20 mM $NaPO_4$, 0.5 M NaCl, 40 mM imidazole, pH 7.4. The clarified periplasmic fraction was loaded onto the column and washed with equilibration buffer for 10 column volumes and bound protein was eluted with 20 mM NaPO, 0.5 M NaCl, 500 mM imidazole, pH 7.4. Eluted scFvs were collected, concentrated using a 10 kDa centrifugal filter (Millipore, Burlington, Mass.), and buffer exchanged into DPBS using a Sephadex G-25 PD-10 desalting column (GE Healthcare, Chicago, Ill.). Each scFv was subject to analysis by reducing and non-reducing SDS-PAGE and protein concentrations were measured based on absorbance at 280 nm using a NanoDrop One UV-Vis Spectrophotometer (ThermoFisher Scientific, Waltham, Mass.).

IgG Production

The heavy chain and light chain variable domains of the B12 sequence were cloned separately into pFUSEss human IgG expression vectors (Invivogen, San Diego, Calif.) and co-transfected into HEK293T cells. The serum was collected after 72 hours, filtered through a 0.45 µm filter, and purified using a 1 mL HiTrap Protein A HP column (GE Healthcare, Chicago, Ill.). The column was equilibrated with 20 mM sodium phosphate, pH 7.4. The serum was loaded onto the column and washed with equilibration buffer for 10 column volumes and bound protein was eluted with 0.1 M citric acid, pH 3. Eluted IgG was collected, concentrated using a 50 kDA centrifugal filter (Millipore, Burlington, Mass.), buffer exchanged into DPBS, and analyzed as described above.

Surface Plasmon Resonance

Surface plasmon resonance measurements were obtained using a forteBIO OctetRED384 instrument. Biotinylated recombinant human FAP and murine FAP protein was captured on a SAX (high precision streptavidin) biosensor by streptavidin coupling. Dilutions of B12 IgG in PBS (3:1 serial dilutions from 1 µg/mL to 1.372 ng/mL) were injected over the biosensor for 300 sec followed by a 300 sec dissociation in PBS. Binding affinities were derived by analysis of the generated sensograms using the forteBIO evaluation software. The equilibrium RU observed for each injection was plotted against protein concentration and fit to a steady-state affinity model included in the evaluation software for determination of the equilibrium binding affinity ($K_D$).

Confocal Microscopy

External staining: Cancer cell lines (2,000 cells/well) were seeded in a 96-well plate in triplicate and incubated in cell culture media at 37° C., 5% $CO_2$ for 30 hours. After washing 2× with PBS, cells were fixed in 10% formalin for 10 minutes. Cells were washed 3× with PBS, 2% BSA and incubated in PBS with B12 IgG (20 µg/mL) for 1 hour at 37° C. with gentle shaking. After washing twice with PBS, cells were probed with an Alexa Fluor 488 conjugated anti-human IgG monoclonal antibody (10 µg/mL) for 1 hour at RT. After washing twice with PBS, cells were imaged by confocal microscopy (FluoView FV1000, Olympus, Tokyo, Japan).

Internalization: Cancer cell lines (2,000 cells/well) were seeded in a 96-well plate in triplicate and incubated in cell culture media at 37° C., 5% $CO_2$ for 30 hours. After washing 2× with PBS, cells were incubated in PBS with B12 IgG (20 µg/mL) for 1 hour. Cells were washed 2× with PBS, 2% BSA followed by washing 2× with 0.2 M glycine, pH 2.4 solution to remove antibody bound externally. Cells were fixed in 10% formalin for 10 minutes and permeabilized in 0.25% Triton X-100 for 10 minutes. Cells were washed twice with PBS and an Alexa Fluor 488 conjugated anti-human IgG monoclonal antibody (10 µg/mL) was used to probe the cells for 1 hour. After washing twice with PBS, cells were imaged by confocal microscopy (FluView FV1000, Olympus, Tokyo, Japan).

IgG Labeling for Flow Cytometry

A total of 1 mg of B12 IgG was labeled with three times Alexa Fluor 488-NHS ester (Life Technologies, Carlsbad, Calif.) dissolved in DMSO under alkaline conditions (pH 9.0) using 1 M sodium bicarbonate. The conjugation reaction was performed for 90 minutes at room temperature with gentle rocking. Unbound Alexa Fluor 488 was removed by performing a buffer exchange into DPBS using a Sephadex G-25 PD-10 desalting column (GE Healthcare, Chicago, Ill.). Labeled B12 IgG was concentrated using a 50 kDa centrifugal filter (Millipore, Burlington, Mass.) and the protein concentration and the degree of labeling was calculated as follows:

$$\text{Protein concentration (M)}: \frac{A_{280} - 0.11(A_{494}) \times \text{Dilution Factor}}{\varepsilon_{protein}}$$

$$\text{Degree of labeling (moles dye/mole protein)}: \frac{A_{494} \times \text{Dilution Factor}}{\varepsilon_{dye} \times \text{protein conc. (M)}}$$

Flow Cytometry

Cells were harvested by incubation with TrypLE for 5 minutes at 37° C. and 5% $CO_2$. $1 \times 10^6$ cells were stained with 100 nM or 500 nM Alexa Fluor 488 conjugated B12 IgG for 1 hour at 4° C. Cells were washed three times and resuspended in flow cytometry staining buffer (eBioscience, ThermoFisher Scientific, Waltham, Mass.). Cell samples were analyzed on a FACSCalibur flow cytometer (Becton Dickinson, Franklin Lakes, N.J.) and at least 10,000 viable cells were gated and analyzed with FlowJo software (FlowJo, LLC, Ashland, Oreg.).

IgG Labeling for Near-Infrared Fluorescent Imaging

A total of 3 mg B12 IgG was labeled with 0.3 mg IRDye 800 CW-Ester NHS/mg protein dissolved in DMSO under alkaline conditions (pH 8.5) using 1 M sodium bicarbonate. The conjugation reaction was performed for 2 hours at room temperature with gentle rocking. Unbound dye was removed and the degree of labeling was calculated as described above.

Animal Models

The animal work was in accordance with a UMN Institutional Animal Care and Use Committee protocol. Four- to six-week-old athymic nude mice were purchased from Envigo (Huntingdon, United Kingdom). Nude mouse xenografts (n=4/xenograft cell line) were generated by subcutaneous injection of each cell line ($5 \times 10^6$ cells/mL; 100 µL per site/mouse). Animals for imaging studies had tumor volumes between 100-350 $mm^3$. The intracardiac dissemination model was generated using the previously described method (Park et al. 2010 Curr. Protoc. Pharmacol. 51:14.15-14.15.27). Nude mouse metastases were generated by intracardiac injection of R1-EnzR$^{FAP}$ cells ($1 \times 10^6$ cells/mL; 100 L per mouse). Animals were imaged weekly starting at three weeks post-injection using bioluminescent imaging (BLI) to detect metastatic colony formation.

In Vivo Near-Infrared Fluorescent Imaging

One nmol IRD-800CW conjugated B12 IgG was injected per mouse via tail vein. Images were collected in fluorescence mode on an IVIS Spectrum (PerkinElmer, Inc., Waltham, Mass.) using Living Image 2.50.2 software at 24 hour intervals. Region of interest measurements were made by placing a 0.5 cm circle in the center of the tumor Signal intensity of the tumor xenografts is expressed as total signal with the background signal subtracted. Data are represented as mean±SEM. For bioluminescent imaging (BLI), the mice were injected intraperitoneally with D-luciferin (150 mg/kg body weight). Images were acquired 10 minutes after the injection of D-luciferin.

Micro-Computed Tomography and Bone Surface Thickness Analysis

Mice were imaged by micro-computed tomography using an Inveon µPET/CT system (Siemens, Munich, Germany) with standard conditions. Data were reconstructed and analyzed with AMIRA software. Images were cropped to contain both anterior limbs of the animals. Thickness threshold was set at t=300 to remove non-osseous anatomy. Surface thickness was calculated by creating surface mesh of the labeled limbs. Surface with measured thickness was color coded and thickness saturation was set at >0.5 mm.

Immunohistochemistry

Whole sections (4 µm) were cut from formalin-fixed, paraffin-embedded blocks. Tissues were mounted on glass slides, deparaffinized in xylene, and rehydrated in decreasing concentrations of ethanol using standard methods. For antigen retrieval, slides were incubated in pH 6.0 buffer (Reveal Decloaking reagent, Biocare Medical) in a steamer for 30 min at 95-98° C., followed by a 20 minute cool down period. Endogenous peroxidase activity was quenched by slide immersion in 3% hydrogen peroxide solution (Sniper, Biocare Medical) for 10 minutes followed by TBST rinse. A serum-free blocking solution (Peroxidase, Biocare Medical) was placed on sections for 30 minutes. Blocking solution was removed and slides were incubated in secondary biotinylated goat anti-human IgG monoclonal antibody (10 µL/mL; Vector, BA-3000) diluted in 10% blocking solution/ 90% TBST. Detection of the antibody complexes was done by the avidin-biotin immunoperoxidase method. As a negative control, the section was only treated with biotinylated serum antibodies followed by the colorimetric reaction.

Statistical Analysis

Data were analyzed using Prism (GraphPad Software, San Diego, Calif.). Student's t-test or one-way ANOVA with multiple comparisons were used to determine statistical significance among groups. All assays were performed with three biological replicates; data are represented as mean±SEM. A p-value below 0.05 was considered statistically significant.

Example 2

This Example describes the use of an NK-92 cell line that was engineered to express IL-2 and stably express CD64 (NK92MI$^{CD64}$) to test the efficacy of the anti-FAP mAb.

Natural killer (NK) cells are cytotoxic lymphocytes that detect and kill virally infected or malignant cells. Human NK cells express an array of activating receptors, however, antibody dependent cell cytotoxicity (ADCC) is mediated exclusively through the IgG Fc receptor CD16A (FcγIIIA) (Alderson et al. J Biomed Biotechnol 2011; 2011:379123; Wang et al. Front Immunol. 2015; 6:368). Activation of CD16A on the cell surface leads to rapid downregulation, specifically through cleavage by a disintegrin and metalloproteinase-17 (ADAM17) (Lajoie et al. J Immunol. 2014 192:741-51; Lai et al. Clin Cancer Res. 1996; 2:161-73. Targeting NK cells to solid tumors can be improved by engineering NK cells to express CD64 (FcγR1), a high affinity receptor for human immunoglobulin G (IgG) Fc expressed by myeloid cells, in combination with therapeutic monoclonal antibodies (mAbs) (Nimmerjahn et al. Nat Rev Immunol. 2008; 8:34-47; Kiyoshi et al. Nat Commun. 2015; 6:6866; Bruhns et al. Blood 2009; 113:3716-25.) Previous studies have stably expressed CD64 (FcγRI) in NK92 cells (NK92MI$^{CD64}$) and shown that CD64 can capture soluble mAbs with two to three orders of magnitude higher affinity than CD16A. (Snyder et al. Front Immunol. 2018; 9:2873.) CD64 also lacks the ADAM17 cleavage site which prevents receptor downregulation. Engineered NK92MI$^{CD64}$ cells mediate tumor cell killing when anti-tumor mAb is bound before treatment, and therefore, can function as a "ready-made CAR." This docking platform allows for switchable targeting elements and development of combination mAb-NK cell therapies without needing to design multiple CAR constructs (see FIG. 11B.).

Results

Figure 12A:
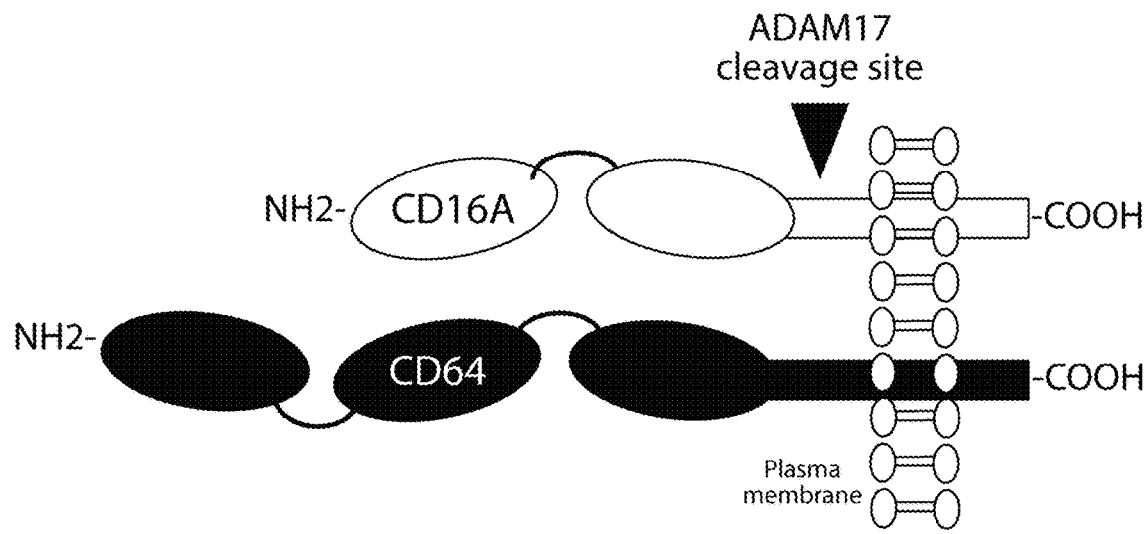
FIG. 12A shows a schematic representation of the cell membrane forms of CD16A and CD64.
Figure 12B:
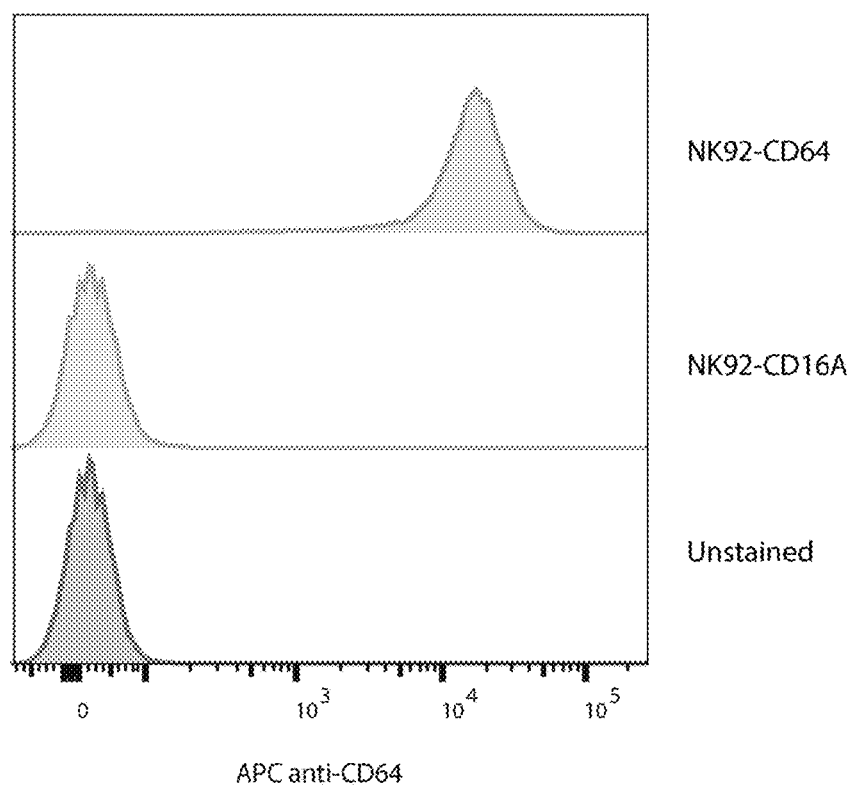
FIG. 12B. NK92MI stably expressing CD64 (NK92MI$^{CD64}$) and NK92MI stably expressing CD16A (NK92MI$^{CD16A}$) were stained with an APC conjugated anti human CD64 monoclonal antibody (mAb) and analyzed by flow cytometry for CD64 expression.

As shown in FIG. 12, human CD64 is stably expressed by NK92MI$^{CD64}$ cells, as analyzed by flow cytometry. CD64 can capture soluble mAbs with two to three orders of magnitude higher affinity than CD16A (Snyder et al. *Front Immunol.* 2018; 9:2873). CD64 also lacks the ADAM17 cleavage site which prevents receptor downregulation and enhances the cytotoxic effect from ADCC and therapeutic mAb-directed killing.

Figure 13A:
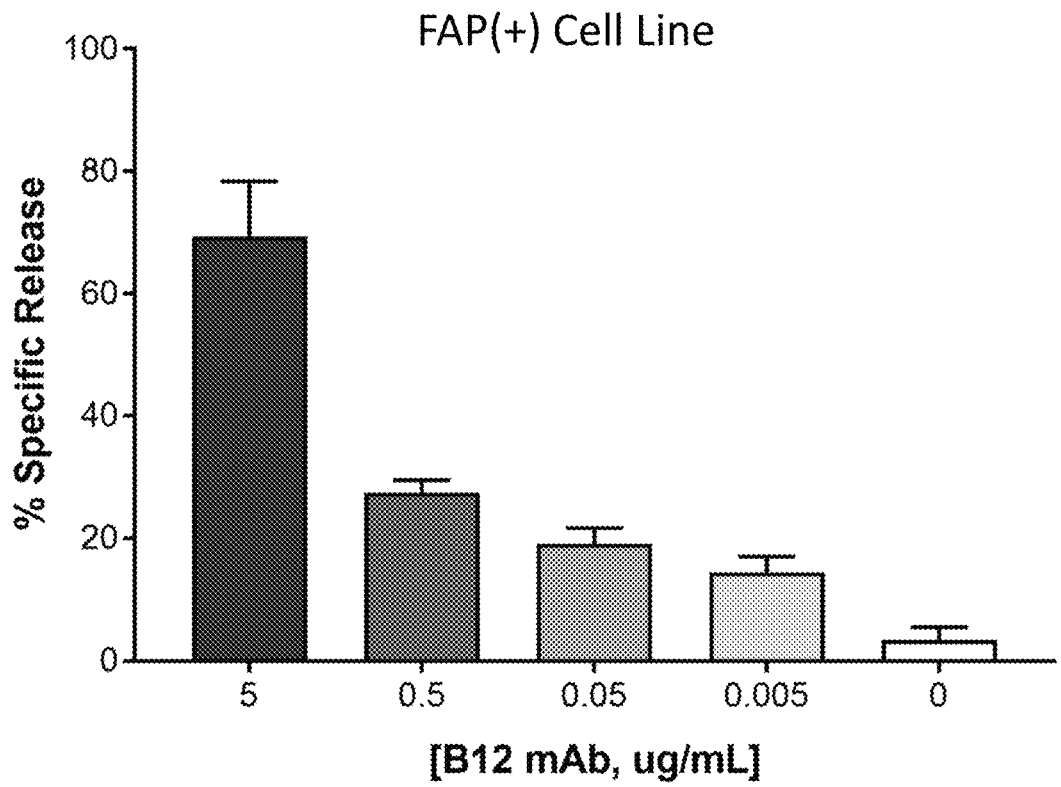
FIG. 13A-FIG. 13B show anti-FAP mAb (B12 IgG) mediates NK92MI$^{CD64}$ cell antibody dependent cell cytotoxicity (ADCC).
Figure 13B:
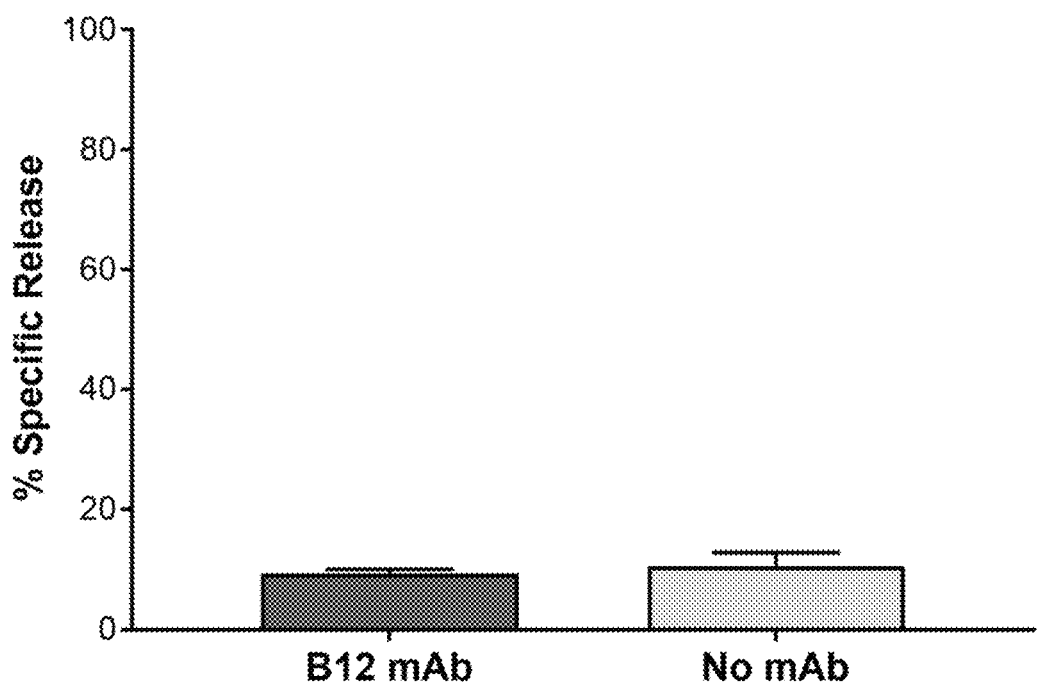

The ability of anti-FAP mAb B12 IgG to mediate ADCC in the NK92MI$^{CD64}$ cells was evaluated. For all in vitro cytotoxicity experiments an immortalized human prostate cancer stromal cell line (hPrCSC-44), characterized as a cancer-associated fibroblast that highly expresses FAP, was used. Potent cell killing at the highest concentration of mAb used was observed and a concentration dependent effect suggested that the anti-FAP mAb mediates the NK92MI$^{CD64}$ cell ADCC (FIG. 13A). All cell killing was measured using the fluorescence based DELFIA EuTDA cytotoxicity assay (PerkinElmer, Inc., Waltham, Mass.) as described in Snyder et al. *Front Immunol.* 2018; 9:2873. The assay was repeated using the highest concentration of anti-FAP mAb and a FAP negative cell line (DU145). When cell killing was measured, there was no significant difference between the antibody and no antibody conditions, suggesting that the therapeutic mAb must be selective for the target cells for NK92MI$^{CD64}$ cell ADCC to occur (FIG. 13B). The baseline levels of killing can be accounted for the fact that NK cells have multiple mechanisms of identifying and killing malignant cells (for example, activating receptors, expression of death ligands). The cell line used in the second experiment is a prostate cancer cell line that does not express FAP.

To test if the NK92MI$^{CD64}$ cells were able to capture soluble anti-FAP mAb, anti-FAP mAb capture was detected using an APC conjugated anti-human IgG1 secondary mAb. Capture of an antibody by NK92MI$^{CD64}$ cells is also referred to herein as "docking" or "binding" anti-FAP mAb; the antibody binds to the receptor (CD64) and is not released.

Figure 14:
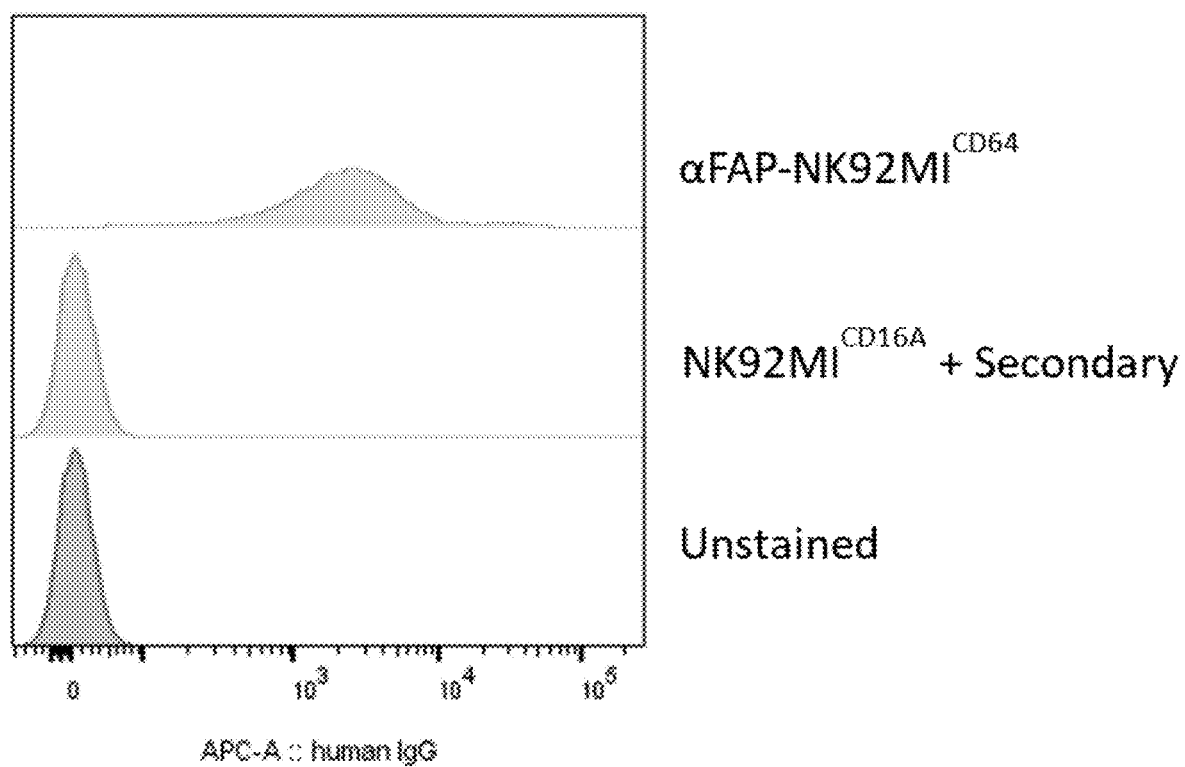
FIG. 14 shows CD64 captures soluble anti-FAP mAb (B12 IgG). NK92MI$^{CD64}$ cells were incubated with or without anti-FAP mAb (5 μg/mL) in serum free media at 37° C. for 2 hours. Effector cells were washed once, stained with an APC conjugated anti-human IgG secondary mAb for 30 minutes, and analyzed by flow cytometry. Samples were compared to an unstained control. Data is representative of three independent experiments.

To capture anti-FAP mAb, NK92MI$^{CD64}$ cells (1×10$^6$ cells/mL) were incubated with anti-FAP mAb (B12 IgG) (5 µg/mL) in serum free media at 37° C. for 2 hours. Effector cells were washed once, stained with an APC conjugated anti-human IgG secondary mAb (1:200 dilution) for 30 minutes on ice, and analyzed by flow cytometry. Over 98% of the cells incubated with the anti-FAP mAb were positively stained when analyzed by flow cytometry. (FIG. 14) These results indicate that the NK92MI$^{CD64}$ cells tightly bind to B12 IgG and could be used for directed cell killing of cancer associated fibroblasts.

Figure 15A:
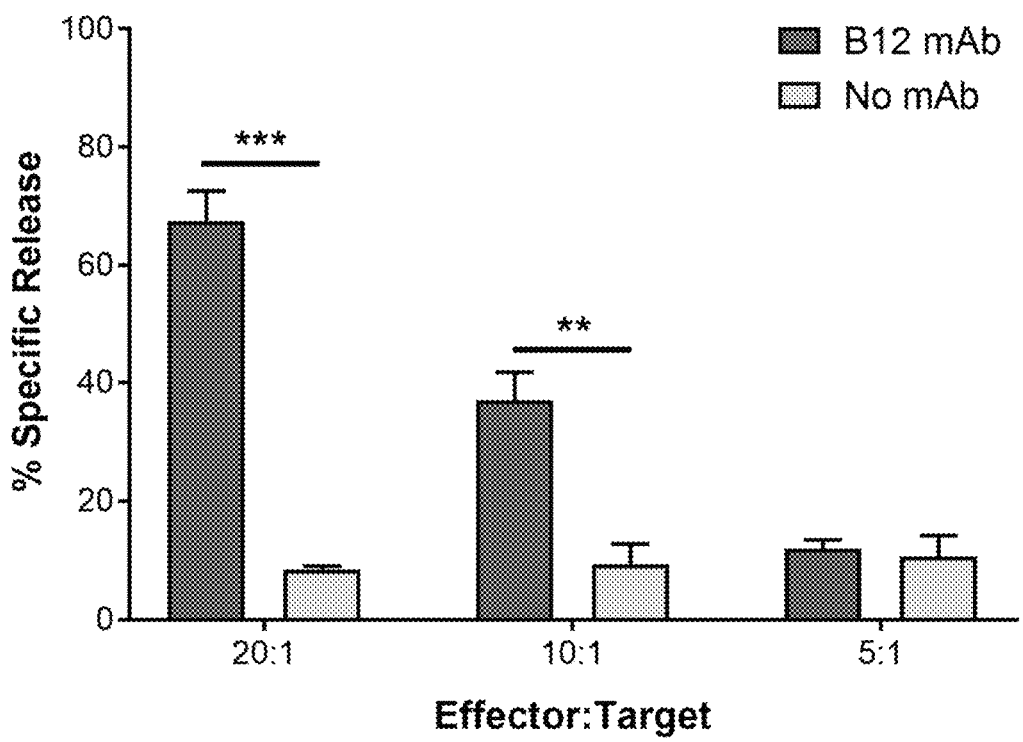
FIG. 15A-FIG. 15B shows that NK92MI cells that stably express CD64 with docked anti-FAP mAb (αFAP-NK92MIC$^{D64}$) cells demonstrate selective anti-tumor activity.
Figure 15B:
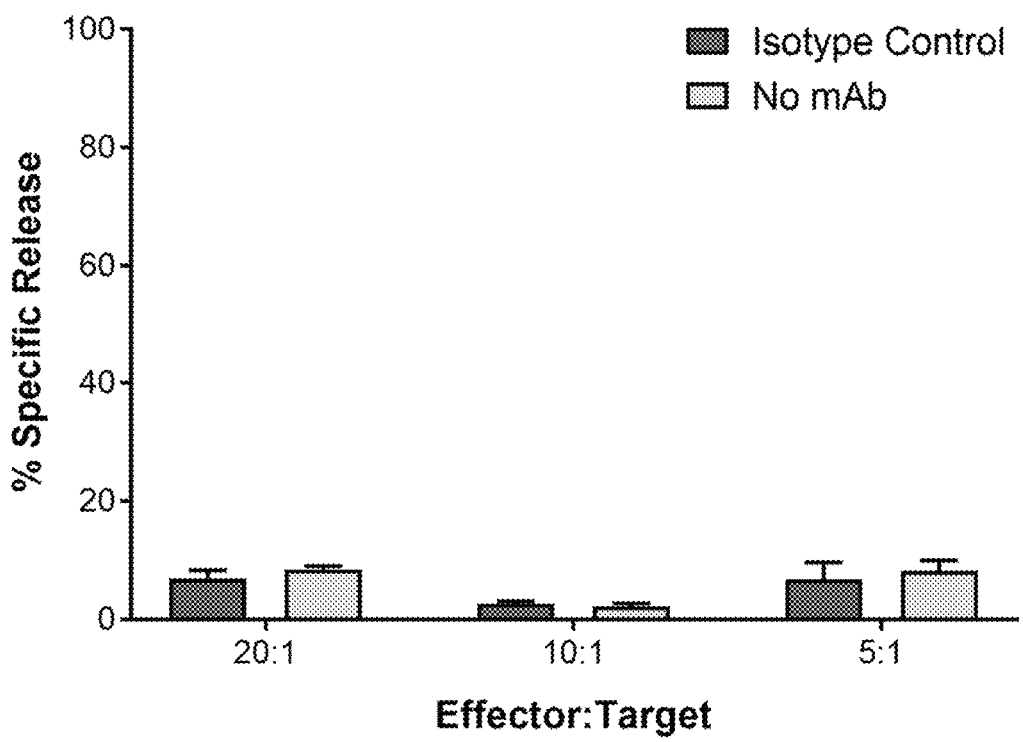
Figure 16A:
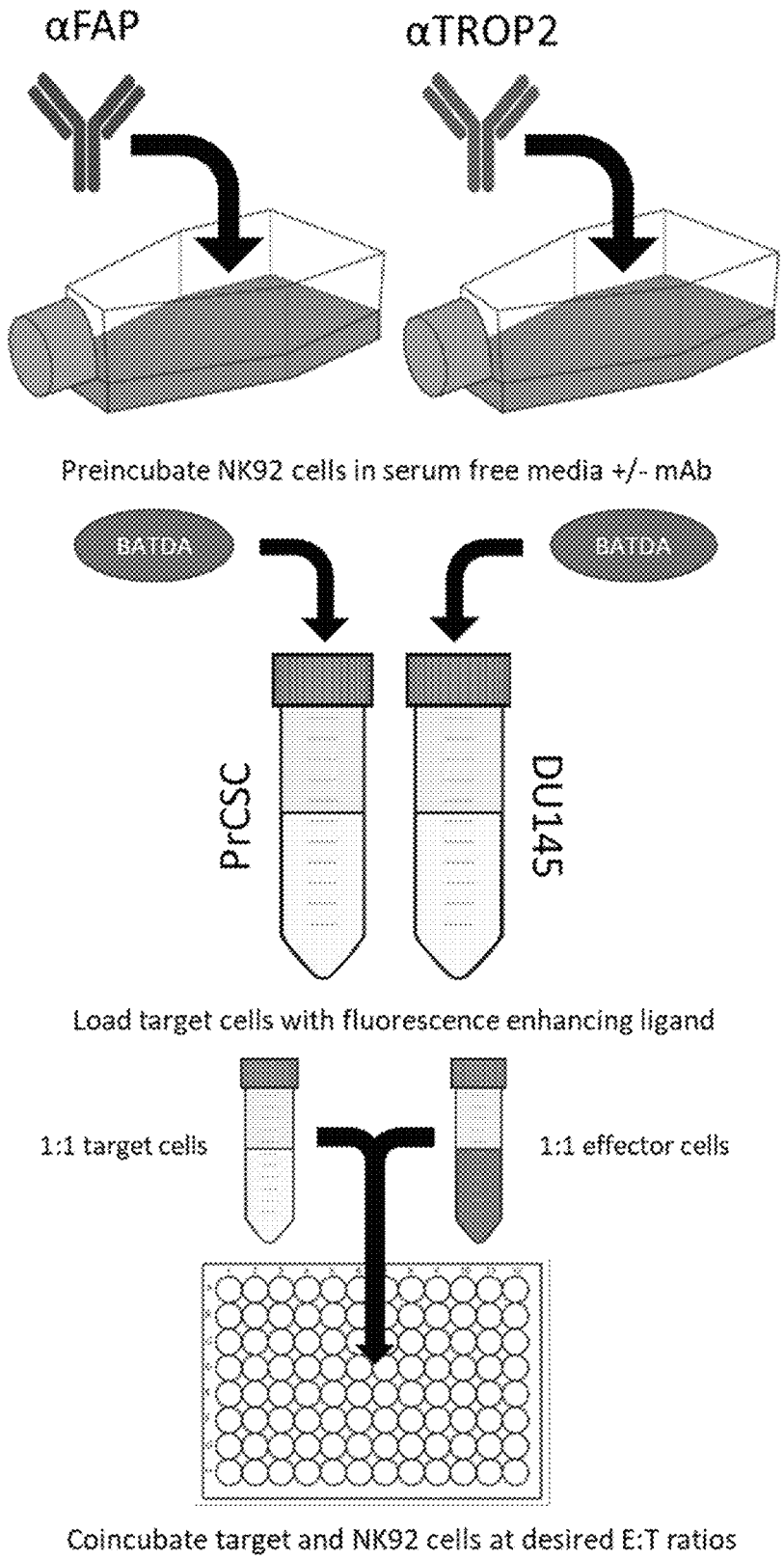
FIG. 16A shows a schematic of the method used to produce the results shown in FIG. 16B. NK92MI$^{CD64}$ cells were preincubated with or without anti-FAP or anti-TROP2 mAbs (5 ug/mL) in serum free media for 2 hours at 37° C. Effector cells were incubated with hPrCSC-44 (FAP+) and DU145 (TROP2+) target cells, loaded with BATDA ligand, at an E:T ratio of 20:1 ($1.6 \times 10^5$ cells: $8 \times 10^3$ cells (1:1 ratio of target cells) at 37° C. for 2 hours. After co-incubation, cytotoxicity was determined by the DELFIA EuTDA cell cytotoxicity assay (PerkinElmer, Inc., Waltham, Mass.). Results are shown in FIG. 16B. Data are represented as % specific release and the mean±SEM of three independent experiments is shown. Statistical significance is indicated as ** p<0.01.

NK92MI cells that stably express CD64 (NK92MI$^{CD64}$) with docked anti-FAP mAb (αFAP-NK92MI$^{CD64}$) were tested against the human prostate cancer stromal cell line hPrCSC-44 to test the killing efficacy. To capture the antibody, NK92MI$^{CD64}$ cells were incubated in serum free media at a density of 1×10$^6$ cells/mL with or without 5 µg/mL mAb (B12 IgG) for 2 hours at 37° C. After incubation, cells were centrifuged and washed once with serum free media. After washing, cells were resuspended in serum free media and counted. Cell were then aliquoted at appropriate density for each E:T ratio. NK92MI$^{CD64}$ cells with or without pre-docked anti-FAP mAb were co-incubated with target cells at the indicated Effector:Target ratios. Potent cell killing by the αFAP-NK92MI$^{CD64}$ cells was observed at the highest Effector:Target (E:T) ratio and the % specific release was significantly higher than the NK92MI$^{CD64}$ cells alone (FIG. 15A). This trend was also seen at the lower 10:1 E:T ratio. This data suggests that the anti-FAP mAb can effectively direct the NK92MI$^{CD64}$ cells to the target cells which causes activation that results in potent cell killing. Next, we switched the targeting therapeutic mAb to a human IgG1 isotype control and repeated the experiment with hPrCSC-44 target cells from a human prostate cancer stroma cell line that highly expresses FAP (FIG. 15B). Cell killing was measured, and no significant difference between the isotype-NK92MI$^{CD64}$ and NK92MI$^{CD64}$ cells was observed; killing was at baseline levels. These data suggests that the NK92MI$^{CD64}$ cells kill target cells in a target-selective mechanism. Even with a mAb bound, the cells will not become activated and kill the target cells unless the mAb interacts with its target protein. The baseline levels of killing can be accounted for the fact that NK cells have multiple mechanisms of identifying and killing malignant cells (for example, activating receptors, expression of death ligands).

Due to the success of the αFAP-NK92MI$^{CD64}$ monotherapy described above, the efficacy of a combination cell therapy including both NK92MI cells that stably express CD64 with docked anti-FAP mAb (αFAP-NK92MI$^{CD64}$) and NK92MI cells that stably express CD64 with docked anti-TROP2 mAb (αTROP2-NK92MI$^{CD64}$) was tested. Solid tumors adopt a complex microenvironment to evade immune detection and augment progression of the disease. Previous studies have seen a synergistic effect of combination therapies that target both the tumor stroma and malignant cells (Brunker et al. *Mol Cancer Ther.* 2016; 15:946-57; Gottschalk et al. *PLoS One* 2013; 8:e82658; Fang et al. *Mol Ther Oncolytics* 2016; 3:16007; Chan et al. *Oncogene* 2018; 37:160-173). hPrCSC-44 cells that highly express FAP and DU145 cells that highly express TROP2 (an epithelial glycoprotein that is overexpressed in prostate cancer and has been used as a biomarker of advanced prostate cancer) were used as target cells. The anti-FAP mAb B12 IgG and an anti-TROP2 mAb were used to direct the NK92MI$^{CD64}$ cells to the target cells and activate cell killing.

Figure 16B:
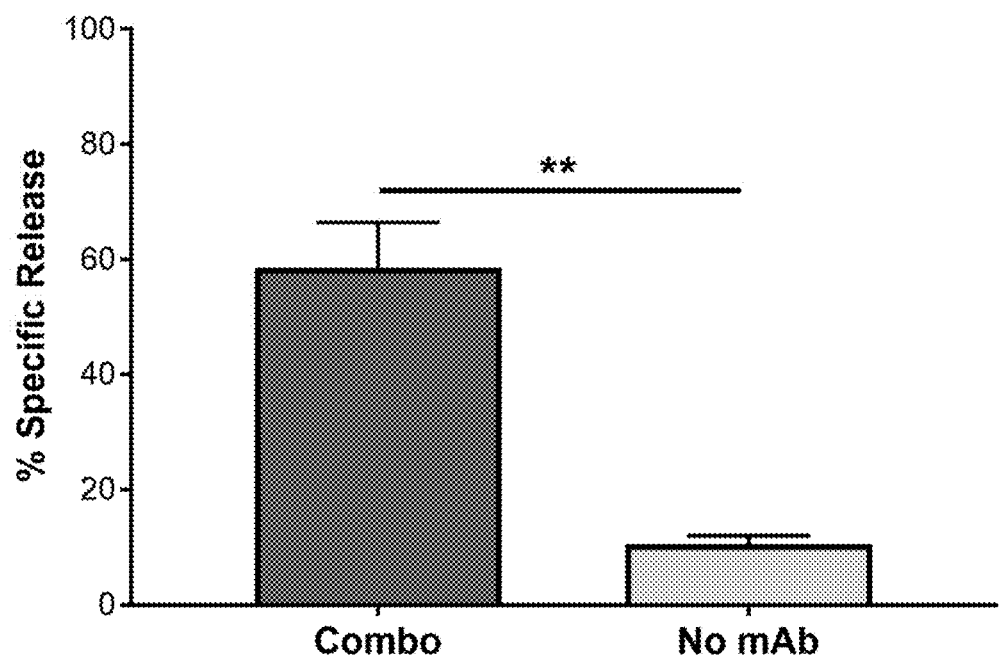

NK92MI$^{CD64}$ cells were preincubated with either anti-FAP or anti-TROP2 mAb to dock the therapeutic antibody. Control NK92MI$^{CD64}$ cells were also preincubated without any mAb. A 1:1 ratio of target cells (8×10$^3$ cells total) and 1:1 ratio of αFAP-NK92MI$^{CD64}$ were added to αTROP2-NK92MI$^{CD64}$ cells (1.6×10$^5$ cells total) at an E:T ratio of 20:1 FIG. 16A). Potent cell killing by the αFAP-NK92MI$^{CD64}$ and αTROP2-NK92MI$^{CD64}$ combination therapy was observed and percent (%) specific release was significantly higher than the NK92MI$^{CD64}$ cells alone (FIG. 16B). The baseline levels of killing are likely the rest of NK cells' multiple mechanisms of identifying and killing malignant cells (for example, activating receptors, expression of death ligands). These data suggest that the combination cell therapy is effective at killing both target cells. Theoretically, either monotherapy alone would only be able to kill, at most, 50% of the target cells in the co-culture since previous data shows selective killing of target-expressing cells.

The results described above suggested the utility of B12 IgG as an imaging probe. To further test the mAb in a more translational model, positron emission tomography/computed tomography (PET/CT), a nuclear imaging modality used in clinics to detect malignancies using a range of radioactive isotopes in combination with non-selective and selective probes, was used. Successful demonstration of the mAb's utility in PET/CT imaging is further proof-of-concept that this mAb could be translated for use in humans to detect activated stroma in the tumor microenvironment. The anti-FAP mAb was tested in mice bearing FAP positive intra-tibial xenografts. Intra-tibial xenografts serve as a model for metastatic prostate cancer since 90% of prostate cancer metastatic lesions are found in the bone. Before PET/CT imaging, tumors were confirmed by bioluminescence imaging (BLI) (FIG. 17, left panels). Mice were treated via tail vein with either anti-FAP mAb (B12 IgG, FIG. 17, top panels) or a human IgG1 isotype control (FIG. 7, bottom panels) conjugated with Zirconium-89. Mice were imaged at 24 hours, 48 hours, and 72 hours. Data was reconstructed using Amira software and diseased limbs were compared to healthy limbs in both the anti-FAP mAb and isotype control treated mice. Tumor specific localization of the anti-FAP mAb in the diseased limb was observed, as indicated by the intensity of the PET signal. In contrast, the anti-FAP mAb did not localize to the healthy limb and the isotype control did not localize to either the diseased or healthy limb, as indicated by the background level of PET signal. These data suggest that the anti-FAP mAb can selectively detect FAP-positive metastatic prostate cancer tumors by PET/CT imaging after systemic treatment with the mAb.

Finally, to test the ability of the anti-FAP mAb to detect stroma cells in a human prostate cancer xenograft, hPrCSC-44 cells that highly express FAP and DU145 prostate cancer cells were subcutaneously implanted in mice with a 2:1 ratio of CAF:DU145 cells. Tumor bearing mice were treated via tail vein with IRDye-800CW conjugated anti-FAP mAb and imaged at 24 hours, 48 hours, and 72 hours. Tumor selective localization of the anti-FAP mAb was observed, as indicated by the intensity of the near infrared signal (FIG. 18). At the imaging endpoint (72 hours), tumors were excised and imaged ex vivo. Fluorescence was observed in the tumor tissue suggesting the accumulation and retention of the anti-FAP mAb in the tumor tissue. These data suggest that the anti-FAP mAb (B12 IgG) can detect and localize to FAP positive tissue within tumors by fluorescence imaging after systemic treatment with the mAb.

Experimental Procedures

Generation of Human CD64/CD16A Expression Constructs

Engineered NK92 cells expressing CD64 or CD16A were produced as described in Snyder et al. *Front Immunol.* 2018; 9:2873.

Stable Expression of CD64/CD16A in NK Cells

NK92MI cells, a human NK cell line that is deficient for endogenous FcγR expression, were stably transduced with pBMN-IRES-EGFP retrovirus expression constructs containing CD64/16A or wildtype CD16A cDNA using retrovirus infection procedures described previously (Jing et al. *PLoS One* 2015; 10:e0121788; Mishra et al. *Cancer Immunol Immunother.* 2018; 67:1407-1416). eGFP fluorescence and surface expression of CD64, CD16, and various NK cell phenotypic markers were determine using flow cytometry analysis.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A composition comprising a compound that binds to fibroblast activation protein alpha (FAP), wherein the compound comprises
an amino acid sequence comprising SEQ ID NO:3, SEQ ID NO:4, and SEQ ID NO:5; and
an amino acid sequence comprising SEQ ID NO:6, SEQ ID NO:7, and SEQ ID NO:8.

2. The composition of claim 1, wherein the compound comprises an amino acid sequence comprising SEQ ID NO:1 and an amino acid sequence comprising SEQ ID NO:2.

3. The composition of claim 1, wherein the compound comprises a monoclonal antibody.

4. The composition of claim 1, wherein the compound comprises a humanized monoclonal antibody.

5. The composition of claim 1, wherein the compound comprises a single-chain variable fragment (scFv).

6. The composition of claim 1, wherein the compound comprises a label.

7. A monoclonal antibody comprising
an amino acid sequence comprising a light chain variable region, wherein the light chain variable region CDR1 sequence comprises SEQ ID NO:3, wherein the light chain variable region CDR2 sequence comprises SEQ ID NO:4, and wherein the light chain variable region CDR3 sequence comprises SEQ ID NO:5; and
an amino acid sequence comprising a heavy chain variable region, wherein the heavy chain variable region CDR1 sequence comprises SEQ ID NO:6, wherein the heavy chain variable region CDR2 sequence comprises SEQ ID NO:7, and wherein the heavy chain variable region CDR3 sequence comprises SEQ ID NO:8.

8. The monoclonal antibody of claim 7, wherein the monoclonal antibody comprises
a light chain variable region comprising the amino acid sequence of SEQ ID NO:1; or
a heavy chain variable region comprising the amino acid sequence of SEQ ID NO:2; or
both.

9. The monoclonal antibody of claim 7, wherein the monoclonal antibody comprises B12 IgG.

* * * * *

SEQUENCE LISTING

```
<160> NUMBER OF SEQ ID NOS: 8

<210> SEQ ID NO 1
<211> LENGTH: 107
<212> TYPE: PRT
<213> ORGANISM: Artificial
<220> FEATURE:
<223> OTHER INFORMATION: VL domain of B12 IgG

<400> SEQUENCE: 1

Asp Ile Val Ile Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Leu Ile Tyr
        35                  40                  45

Ala Ala Ser Thr Leu Asp Ser Gly Val Pro Lys Arg Phe Ser Gly Ser
    50                  55                  60

Arg Ser Gly Ser Asp Tyr Ser Leu Thr Ile Ser Ser Leu Glu Ser Glu
65                  70                  75                  80

Asp Phe Ala Asp Tyr Tyr Cys Leu Gln Tyr Ala Ser Tyr Pro Trp Thr
                85                  90                  95

Phe Gly Gly Gly Thr Lys Leu Glu Ile Lys Arg
            100                 105
```

```
<210> SEQ ID NO 2
<211> LENGTH: 114
<212> TYPE: PRT
<213> ORGANISM: Artificial
<220> FEATURE:
<223> OTHER INFORMATION: VH domain of B12 IgG

<400> SEQUENCE: 2

Glu Val Met Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Leu Val
        35                  40                  45

Ala Thr Ile Asn Ser Asn Gly Gly Ser Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Asp Tyr Phe Asp Tyr Trp Gly Gln Gly Thr Thr Leu Thr Val
            100                 105                 110

Ser Ser

<210> SEQ ID NO 3
<211> LENGTH: 11
<212> TYPE: PRT
<213> ORGANISM: Artificial
<220> FEATURE:
<223> OTHER INFORMATION: B12 IgG light chain CDR1

<400> SEQUENCE: 3

Arg Ala Ser Gln Glu Ile Ser Gly Tyr Leu Ser
1               5                   10

<210> SEQ ID NO 4
<211> LENGTH: 7
<212> TYPE: PRT
<213> ORGANISM: Artificial
<220> FEATURE:
<223> OTHER INFORMATION: B12 IgG light chain CDR2

<400> SEQUENCE: 4

Ala Ala Ser Thr Leu Asp Ser
1               5

<210> SEQ ID NO 5
<211> LENGTH: 9
<212> TYPE: PRT
<213> ORGANISM: Artificial
<220> FEATURE:
<223> OTHER INFORMATION: B12 IgG light chain CDR3

<400> SEQUENCE: 5

Leu Gln Tyr Ala Ser Tyr Pro Trp Thr
1               5

<210> SEQ ID NO 6
<211> LENGTH: 10
<212> TYPE: PRT
<213> ORGANISM: Artificial
<220> FEATURE:
<223> OTHER INFORMATION: B12 IgG heavy chain CDR1
```

```
<400> SEQUENCE: 6

Gly Phe Thr Phe Ser Ser Tyr Gly Met Ser
1               5                   10

<210> SEQ ID NO 7
<211> LENGTH: 17
<212> TYPE: PRT
<213> ORGANISM: Artificial
<220> FEATURE:
<223> OTHER INFORMATION: B12 IgG heavy chain CDR2

<400> SEQUENCE: 7

Thr Ile Asn Ser Asn Gly Gly Ser Thr Tyr Tyr Pro Asp Ser Val Lys
1               5                   10                  15

Gly

<210> SEQ ID NO 8
<211> LENGTH: 5
<212> TYPE: PRT
<213> ORGANISM: Artificial
<220> FEATURE:
<223> OTHER INFORMATION: B12 IgG heavy chain CDR3

<400> SEQUENCE: 8

Asp Tyr Phe Asp Tyr
1               5
```